US008299066B2

(12) United States Patent
Sakagami et al.

(10) Patent No.: US 8,299,066 B2
(45) Date of Patent: Oct. 30, 2012

(54) COMPOUNDS HAVING NPY Y5 RECEPTOR ANTAGONISTIC ACTIVITY

(75) Inventors: Masahiro Sakagami, Hokkaido (JP); Hiroshi Hashizume, Osaka (JP); Satoru Tanaka, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 13/354,881

(22) Filed: Jan. 20, 2012

(65) Prior Publication Data

US 2012/0130070 A1    May 24, 2012

Related U.S. Application Data

(62) Division of application No. 12/936,693, filed as application No. PCT/JP2009/057856 on Apr. 20, 2009, now Pat. No. 8,129,372.

(30) Foreign Application Priority Data

Apr. 21, 2008 (JP) ................... 2008-109778

(51) Int. Cl.
| A61K 31/536 | (2006.01) |
| A61K 31/4439 | (2006.01) |
| A61K 31/40 | (2006.01) |
| A61K 31/4174 | (2006.01) |
| A61K 31/415 | (2006.01) |
| A61K 31/4196 | (2006.01) |
| A61K 31/404 | (2006.01) |
| A61K 31/506 | (2006.01) |
| A61K 31/497 | (2006.01) |
| A61K 31/427 | (2006.01) |
| A61K 31/422 | (2006.01) |
| A61K 31/5377 | (2006.01) |
| A61K 31/437 | (2006.01) |
| A61K 31/519 | (2006.01) |
| A61K 31/4985 | (2006.01) |
| A61K 31/444 | (2006.01) |

(52) U.S. Cl. .............. 514/230.5; 514/235.2; 514/249; 514/255.05; 514/256; 514/265.1; 514/300; 514/333; 514/339; 514/365; 514/374; 514/383; 514/400; 514/406; 514/415; 514/427; 544/105; 544/143; 544/280; 544/333; 544/405; 546/121; 546/256; 546/277.4; 548/205; 548/235; 548/269.4; 548/343.5; 548/377.1; 548/440; 548/560

(58) Field of Classification Search .................. None
See application file for complete search history.

(56) References Cited

U.S. PATENT DOCUMENTS

| 6,699,891 B1 | 3/2004 | Kawanishi et al. |
| 7,265,130 B2 | 9/2007 | Kawanishi et al. |
| 7,534,892 B2 | 5/2009 | Nakatani |
| 7,781,461 B2 | 8/2010 | Kawanishi et al. |
| 2009/0203712 A1 | 8/2009 | Yano |
| 2010/0004295 A1 | 1/2010 | Kouyama |
| 2010/0063027 A1 | 3/2010 | Okuno et al. |
| 2010/0267945 A1 | 10/2010 | Okuno et al. |
| 2010/0273841 A1 | 10/2010 | Okuno et al. |
| 2010/0273842 A1 | 10/2010 | Okuno et al. |

FOREIGN PATENT DOCUMENTS

| EP | 0 978 516 A1 | 2/2000 |
| EP | 1 054 005 A1 | 11/2000 |
| EP | 1 249 233 A1 | 10/2002 |
| EP | 1 719 765 A1 | 11/2006 |
| EP | 1 760 073 A1 | 3/2007 |
| EP | 2 014 285 A1 | 1/2009 |
| EP | 2 017 261 A1 | 1/2009 |
| EP | 2 058 305 A1 | 5/2009 |
| EP | 2 062 878 A1 | 5/2009 |
| EP | 2 221 051 A1 | 8/2010 |
| JP | 98/52940 A1 | 11/1998 |
| JP | 2002-508754 | 3/2002 |
| JP | 2005-527590 | 9/2005 |
| JP | 2006-508117 | 3/2006 |
| WO | 97/20823 A2 | 6/1997 |
| WO | 97/20823 A3 | 6/1997 |
| WO | 99/38867 A1 | 8/1999 |

(Continued)

OTHER PUBLICATIONS

Lars Grundemar, et al., "Neuropeptide Y Effector Systems: Perspectives for Drug Development", Trends in Pharmacological Sciences (TiPS), vol. 15, May 1994, pp. 153-159.

(Continued)

*Primary Examiner* — Sun Jae Loewe
(74) *Attorney, Agent, or Firm* — Oblon, Spivak, McClelland, Maier & Neustadt, L.L.P.

(57) ABSTRACT

This invention provides a compound of the formula (I):

$$\underset{O_2}{\overset{R^1}{\underset{\|}{S}}} \underset{R^2}{\overset{(R)_p}{N}} \underbrace{\phantom{XX}}_{} \underbrace{\text{Ring A}}_{} \underset{(R^4)_n}{\overset{(R^3)_m}{\phantom{X}}} \quad (I)$$

a pharmaceutically acceptable salt or solvate thereof, wherein
$R^1$ is substituted or unsubstituted alkyl or the like,
$R^2$ is hydrogen or substituted or unsubstituted alkyl,
Ring A is monocyclic or bicyclic aromatic heterocycle,
$R^3$ is substituted or unsubstituted aryl, substituted or unsubstituted heteroaryl or substituted or unsubstituted heterocycle,
$R^4$ is halogen, cyano, substituted or unsubstituted alkyl, substituted or unsubstituted cycloalkyl or the like,
m is an integer between 0 and 2,
n is an integer between 0 and 5,
R is halogen, oxo, cyano, nitro, substituted or unsubstituted alkyl or the like, and
p is an integer between 0 and 2
as novel compounds having NPY Y5 antagonistic activity.

7 Claims, No Drawings

FOREIGN PATENT DOCUMENTS

| | | | |
|---|---|---|---|
| WO | 99/40075 | A1 | 8/1999 |
| WO | 00/31063 | A1 | 6/2000 |
| WO | 01/37826 | A1 | 5/2001 |
| WO | 01/44201 | A1 | 6/2001 |
| WO | 01/54507 | A1 | 8/2001 |
| WO | 01/62737 | A2 | 8/2001 |
| WO | 01/62737 | A3 | 8/2001 |
| WO | WO 02/22602 | A2 | 3/2002 |
| WO | WO 02/22607 | A1 | 3/2002 |
| WO | 03/087304 | A2 | 10/2003 |
| WO | 03/087304 | A3 | 10/2003 |
| WO | 03/104255 | A2 | 12/2003 |
| WO | 03/104255 | A3 | 12/2003 |
| WO | 2004/043962 | A1 | 5/2004 |
| WO | 2004/072033 | A2 | 8/2004 |
| WO | 2005/080348 | A1 | 9/2005 |
| WO | 2006/001318 | A1 | 1/2006 |
| WO | 2006/044509 | A2 | 4/2006 |
| WO | 2006044509 | A3 | 4/2006 |
| WO | 2006/076595 | A1 | 7/2006 |
| WO | 2007/004958 | A1 | 1/2007 |
| WO | 2007/079164 | A2 | 7/2007 |
| WO | 2007/079164 | A3 | 7/2007 |
| WO | 2007/125952 | A1 | 11/2007 |
| WO | 2008/026563 | A1 | 3/2008 |
| WO | 2008/026564 | A1 | 3/2008 |
| WO | 2009/054434 | A1 | 4/2009 |

OTHER PUBLICATIONS

Catalina Betancur, et al., "Nonpeptide Antagonists of Neuropeptide Receptors: Tools for Research and Therapy", Trends in Pharmacological Sciences (TiPS), vol. 18, 1997, pp. 372-386.

Ambik Aipakan, et al., "Neuropeptide Y Family of Hormones: Receptor Subtypes and Antagonists", Peptides, vol. 18, No. 3, 1997, pp. 445-457.

Hideo Yukioka, et al., "A Potent and Selective Neuropeptide Y Y5 Receptor Antagonist, S-2367, Attenuates the Development of Diet-Induced Obesity in Mice", Obesity, vol. 14, No. 9, 2006 pp. A235.

Atsuyuki Shimazaki, et al., "Role of Energy Expenditure in the Antiobesity Effect of Neuropeptide Y Y5 Receptor Antagonist S-2367 in Diet-Induced Obese Mice", Obesity, vol. 15. No. 9, 2007, A57.

International Search Report issued Aug. 26, 2010 in PCT/JP2009/057856 filed Apr. 20, 2009.

Chawla et al., "Challenges in Polymorphism of Pharmaceuticals", CRIPS vol. 5, No. 1, Jan.-Mar. 2004.

Newman et al., "Solid-state analysis of the active pharmaceutical ingredient in drug products", DDT vol. 8, No. 19, Oct. 2003, pp. 898-905.

Alzheimer's Disease Treatment Phases, http://www.alzheimerstreatmentorg/treatment/disease-treatment.htm 2010.

Alzheimer's Drugs, Consumer Reports Best Buy Drugs (p. 1-5) 2010.

Ling et al., caplus an 2006:386432.

Kipping, caplus an 1907:6503 (1907).

Supplementary European Search Report issued Mar. 13, 2012, in European Patent Application No. 09 73 3802.

COMPOUNDS HAVING NPY Y5 RECEPTOR ANTAGONISTIC ACTIVITY

CROSS-REFERENCE TO RELATED APPLICATIONS

The present application is a divisional of and claims the benefits of priority to U.S. application Ser. No. 12/936,693, filed Oct. 7, 2010. The entire contents of this application are incorporated herein by reference. U.S. application Ser. No. 12/936,693 is a national stage of PCT/JP2009/057856, filed Apr. 20, 2009, which is based on and claims the benefits of priority to Japanese Application No. 2008-109778, filed Apr. 21, 2008.

FIELD OF THE INVENTION

This invention relates to a novel compound having NPY Y5 receptor antagonistic activity. The compound is useful as a pharmaceutical composition, especially as an anti-obesity drug.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulatory action on food intake, an anti-seizure activity, a learning-enhancing action, an anti-anxiety activity, an anti-stress activity, etc. in the central nervous system, and it may be pivotally involved in central nervous system diseases such as depression, Alzheimer's disease and Parkinson's disease. NPY is thought to be involved in cardiovascular diseases, since it induces a contraction of smooth muscles such as blood vessels or cardiac muscles in peripheral tissues. Furthermore, NPY is also known to be involved in metabolic diseases such as obesity, diabetes and hormone abnormalities (Non-patent Document 1). Therefore, a pharmaceutical composition having NPY Y5 receptor antagonistic activity is expected as medicine for preventing or treating the above-mentioned various diseases associated with the NPY receptor.

Six subtypes of NPY receptors have now been identified: Y1, Y2, Y3, Y4, Y5 and Y6 (Non-patent Document 2). It has been suggested that the Y5 receptor is at least involved in the feeding behavior and its antagonist is expected as an anti-obesity drug (Non-patent Documents 3 to 5).

Benzimidazole and imidazopyridine derivatives having sulfonyl group and having NPY Y5 receptor antagonistic activity are disclosed in Patent Document 1. Amine derivatives having sulfonyl group and having NPY Y5 receptor antagonistic activity are disclosed in Patent Document 2 and the like. Amide derivatives having sulfonyl group and having NPY Y5 receptor antagonistic activity are disclosed in Patent Documents 3 to 5 and the like. The structures of these compounds are different from those of the compounds of this invention.

Compounds having different structures from the compounds of this invention and having NPY Y5 receptor antagonistic activity are disclosed in Patent Document 6 and the like.

Furthermore, although compounds having similar structures to compounds of this invention are disclosed in Patent Documents 7 to 14, the activities of their compounds are quite different from those of the compounds of this invention and these documents do not suggest this invention.

PRIOR ART DOCUMENTS

Patent Documents
Patent Document 1: WO2005/080348
Patent Document 2: WO2007/125952
Patent Document 3: WO01/037826
Patent Document 4: WO2006/001318
Patent Document 5: WO2003/104255
Patent Document 6: WO97/20823
Patent Document 7: WO99/40075
Patent Document 8: WO2000/31063
Patent Document 9: WO2001/054507
Patent Document 10: WO2003/087304
Patent Document 11: WO2004/072033
Patent Document 12: WO2004/043962
Patent Document 13: WO2006/076595
Patent Document 14: WO2004/079164
Non-patent Documents
Non-patent Document 1: Trends in Pharmacological Sciences, Vol. 15, 153 (1994)
Non-patent Document 2: Trends in Pharmacological Sciences, Vol. 18, 372 (1997)
Non-patent Document 3: Peptides, Vol. 18, 445 (1997)
Non-patent Document 4: Obesity, Vol. 14, No. 9, A235 (2006)
Non-patent Document 5: Obesity, Vol. 15, No. 9, A57 (2007)

DISCLOSURE OF INVENTION

Problems to be Solved by the Invention

The object of this invention is to provide novel compounds having strong NPY Y5 receptor antagonistic activity.

Means for Solving the Problem

The present inventors have achieved to synthesize the novel compounds having high NPY Y5 receptor antagonistic activity through their intensive studies. Moreover, they have found that the compounds showed significant suppressive effects on body weight. Patent Document 1 has disclosed compounds wherein Ring A of the following formula (I) were imidazopyridine or benzimidazole as a compound exhibited NPY Y5 receptor antagonistic activity. However, the present inventors have detected that a compound wherein Ring A of the formula (I) is benzimidazole did not show good brain penetration. By pharmacokinetic analysis they have also discovered that the compound with Ring A of the formula (I) being benzimidazole showed a high drug clearance and a short half-life causing a rapid disappearance from the rat body when the compound was injected intravenously. Furthermore, they found that compounds wherein imidazopyridine or benzimidazole in Ring A of the formula (I) was substituted with monocyclic or bicyclic aromatic heterocycle except for imidazopyridine or benzimidazole, showed better brain penetration compared to the compound with Ring A of the formula (I) being benzimidazole. Especially, compounds with Ring A of the formula (I) being indole, pyrazole or pyrrole are preferable. They also detected that compounds with Ring A of the formula (I) being indole, imidazole, pyrazole or triazole had more preferable profiles in pharmacokinetic aspects than that being benzimidazole. In addition, the compounds for this invention showed a weak inhibition against drug metabolizing enzyme, great metabolic stability and high water solubility. Furthermore, compounds of this invention were less toxic, therefore it is thought to be safe enough for pharmaceutical use.

This invention includes the followings.

(1) A compound of the formula (I):

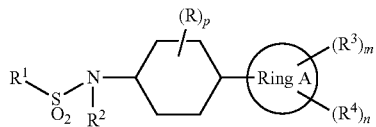

a pharmaceutically acceptable salt or solvate thereof, wherein $R^1$ is substituted or unsubstituted alkyl, substituted or unsubstituted alkenyl, or substituted or unsubstituted alkynyl, $R^2$ is hydrogen or substituted or unsubstituted alkyl, Ring A is monocyclic or bicyclic aromatic heterocycle, $R^3$ is substituted or unsubstituted aryl, substituted or unsubstituted heteroaryl, or substituted or unsubstituted heterocyclyl, $R^4$ is halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl, hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heteroaryloxy, substituted or unsubstituted heterocyclyloxy, mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclylthio, carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heteroaryloxycarbonyl, substituted or unsubstituted heterocyclyloxycarbonyl, substituted or unsubstituted carbamoyl, formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclylsulfonyl, substituted or unsubstituted sulfamoyl, or substituted or unsubstituted amino, m is an integer between 0 and 2, provided that m is 1 when Ring A is imidazole, pyrazole or pyridine, n is an integer between 0 and 5, R is halogen, oxo, cyano, nitro, substituted or unsubstituted alkyl, substituted or unsubstituted alkenyl, or substituted or unsubstituted alkynyl, p is an integer between 0 and 2, and provided that compounds wherein a group of the formula:

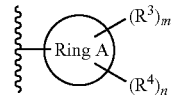

is purinyl optionally having $R^3$ and/or $R^4$, imidazopyridyl optionally having $R^3$ and/or $R^4$, benzimidazolyl optionally having $R^3$ and/or $R^4$,

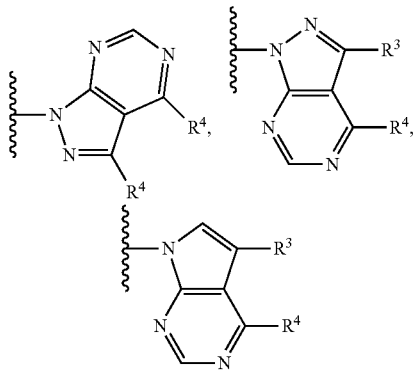

and compounds wherein a group of the formula:

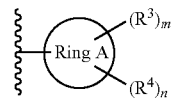

is oxadiazolyl optionally having $R^3$ and/or $R^4$, and $R^1$ is methyl substituted with substituted or unsubstituted phenyl, are excluded.

(2) The compound, pharmaceutically acceptable salt or solvate thereof of (1), wherein Ring A is indole, pyrrolopyridine, pyrrolopyrimidine, pyrrolopyrazine, imidazole, pyrazole, pyrrole, triazole or pyridine.

(3) The compound, pharmaceutically acceptable salt or solvate thereof of (2), wherein Ring A is indole, pyrrolopyridine, pyrrolopyrimidine, pyrrolopyrazine, pyrazole or pyrrole.

(4) The compound, pharmaceutically acceptable salt or solvate thereof of (1), wherein m is 1.

(5) The compound, pharmaceutically acceptable salt or solvate thereof of (1), wherein $R^1$ is alkyl.

(6) The compound, pharmaceutically acceptable salt or solvate thereof of (1), wherein $R^3$ is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted morpholinyl, substituted or unsubstituted morpholino, substituted or unsubstituted pyrrolidinyl, substituted or unsubstituted piperidyl, substituted or unsubstituted piperidino, substituted or unsubstituted benzodioxolyl, substituted or unsubstituted dihydrobenzoxazinyl, or substituted or unsubstituted indazolyl.

(7) The compound, pharmaceutically acceptable salt or solvate thereof of (1), wherein $R^4$ is halogen, cyano, oxo, substituted or unsubstituted alkyl, substituted or unsubstituted cycloalkyl, substituted or unsubstituted alkoxy, or substituted or unsubstituted aryloxy.

(8) The compound, pharmaceutically acceptable salt or solvate thereof of (1), wherein n is 1.

(9) The compound, pharmaceutically acceptable salt or solvate thereof of (1), wherein $R^1$ is substituted or unsubstituted alkyl, $R^2$ is hydrogen, Ring A is indole, pyrrolopyridine, pyrrolopyrazine, pyrrole, triazole or pyridine, $R^3$ is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted morpholinyl, substituted or unsubstituted pyrrolidinyl, or substituted or unsubstituted piperidyl, and $R^4$ is halogen, cyano, substituted or unsubstituted alkyl, substituted or unsubstituted alkoxy or, substituted or unsubstituted aryloxy.

(10) A compound of the formula (I-2):

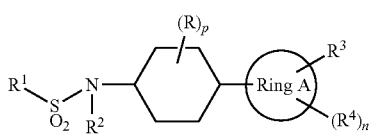

a pharmaceutically acceptable salt or solvate thereof, wherein $R^1$ is substituted or unsubstituted alkyl, substituted or unsubstituted alkenyl, or substituted or unsubstituted alkynyl, $R^2$ is hydrogen or substituted or unsubstituted alkyl, Ring A is imidazole, $R^3$ is substituted or unsubstituted aryl, substituted or unsubstituted heteroaryl, or substituted or unsubstituted heterocyclyl, $R^4$ is halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl, hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heteroaryloxy, substituted or unsubstituted heterocyclyloxy, mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclylthio, carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heteroaryloxycarbonyl, substituted or unsubstituted heterocyclyloxycarbonyl, substituted or unsubstituted carbamoyl, formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclylsulfonyl, substituted or unsubstituted sulfamoyl, or substituted or unsubstituted amino, n is an integer between 0 and 2, R is halogen, oxo, cyano, nitro, substituted or unsubstituted alkyl, substituted or unsubstituted alkenyl, or substituted or unsubstituted alkynyl, and p is an integer between 0 and 2.

(11) A compound of the formula (I-2):

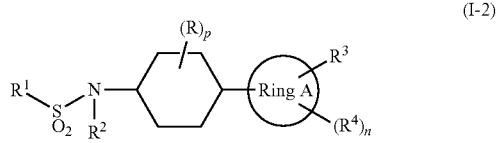

a pharmaceutically acceptable salt or solvate thereof, wherein $R^1$ is substituted or unsubstituted alkyl, substituted or unsubstituted alkenyl, or substituted or unsubstituted alkynyl, $R^2$ is hydrogen or substituted or unsubstituted alkyl, Ring A is pyrazole, $R^3$ is substituted or unsubstituted aryl, substituted or unsubstituted heteroaryl, or substituted or unsubstituted heterocyclyl, $R^4$ is halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl, hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heteroaryloxy, substituted or unsubstituted heterocyclyloxy, mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclylthio, carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heteroaryloxycarbonyl, substituted or unsubstituted heterocyclyloxycarbonyl, substituted or unsubstituted carbamoyl, formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclylsulfonyl, substituted or unsubstituted sulfamoyl, or substituted or unsubstituted amino, n is an integer between 0 and 2, R is halogen, oxo, cyano, nitro, substituted or unsubstituted alkyl, substituted or unsubstituted alkenyl, or substituted or unsubstituted alkynyl, and p is an integer between 0 and 2.

(12) A pharmaceutical composition comprising the compound, pharmaceutically acceptable salt or solvate thereof of any one of (1) to (11) as an active ingredient.

(13) The pharmaceutical composition of (12) having NPY Y5 receptor antagonistic activity.

(14) A method for treatment or prevention of a disease associated with NPY Y5 characterized by administering the compound, pharmaceutically acceptable salt or solvate thereof of any one of (1) to (11).

(15) Use of the compound, pharmaceutically acceptable salt or solvate thereof of any one of (1) to (11) for manufacture of a therapeutic or preventive agent for a disease associated with NPY Y5.

(16) The compound, pharmaceutically acceptable salt or solvate thereof of any one of (1) to (11) for treatment or prevention of a disease associated with NPY Y5.

(17) A compound of the formula:

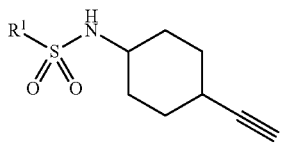

or solvate thereof, wherein $R^1$ is substituted or unsubstituted alkyl.

(18) The compound or solvate thereof of (17), wherein $R^1$ is ethyl, isopropyl or tert-butyl.

Effect of the Invention

A compound of this invention exhibits NPY Y5 receptor antagonistic activity and is very useful as a medicine especially for preventing or treating a disease associated with NPY Y5, e.g. feeding disorder, obesity, hyperorexia, sexual disorder, impaired fertility, depression, epileptic seizure, hypertension, cerebral hemorrhage, congestive heart failure or sleep disorders. Moreover, the antagonist is effective for preventing or treating the diseases in which obesity acts as a risk factor, for example, diabetes, hypertension, hyperlipemia, atherosclerosis and acute coronary syndrome.

MODE FOR CARRYING OUT THE INVENTION

Terms used in the present description are explained below. Each term has the same meaning alone or together with other terms in this description.

"Halogen" includes fluorine, chlorine, bromine and iodine. Especially preferred is fluorine or chlorine.

"Alkyl" includes C1 to C10 straight or branched alkyl group. It includes C1 to C6 alkyl, C1 to C4 alkyl, C1 to C3 alkyl and the like. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

"Alkyl" of $R^1$ is preferably C2 to C10, more preferably C2 to C6 and most preferably ethyl, isopropyl or tert-butyl.

"Alkyl" in other cases is preferably C1 to C6 and more preferably C1 to C4.

"Alkenyl" includes C2 to C10 straight or branched alkenyl having one or more double bond(s) at any possible position(s). It includes C2 to C8 alkenyl, C3 to C6 alkenyl and the like. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

"Alkynyl" includes C2 to C10 straight or branched alkynyl. It includes C2 to C6 alkynyl, C2 to C4 alkynyl and the like. Examples include ethynyl, propynyl, butynyl, pentynyl, hexynyl, heptynyl, octynyl, nonynyl, decynyl and the like. Alkynyl have one or more triple bond(s) at any possible position(s) and can have double bond(s).

"Cycloalkyl" means C3 to C8 cyclic saturated hydrocarbon group. It includes C3 to C6 cycloalkyl, C5 or C6 cycloalkyl and the like. Examples include cyclopropyl, cyclobutyl, cyclopentyl, cyclohexyl, cycloheptyl, cyclooctyl and the like.

"Cycloalkenyl" means C3 to C7 cyclic unsaturated aliphatic hydrocarbon group. Examples are cyclopropenyl, cyclobutenyl, cyclopentenyl, cyclohexenyl, cycloheptenyl, cyclohexadienyl and the like. Cycloalkenyl also includes those bridged cyclic hydrocarbon group and spiro-hydrocarbon group which have an unsaturated bond in the ring.

"Aryl" includes monocyclic of polycyclic aromatic carbocyclyl. Examples are phenyl, naphthyl, anthryl, phenanthryl and the like. It includes the aromatic carbocyclyl fused with cycloalkane (a ring derived from the above "cycloalkyl"). Examples are indanyl, indenyl, biphenylyl, acenaphthyl, tetrahydronaphthyl, fluorenyl and the like.

"Monocyclic aromatic heterocycle" means 4- to 8-membered monocyclic aromatic heterocycle containing one or more heteroatom(s) arbitrarily selected from O, S and N on the ring. Examples are pyrrole, imidazole, pyrazole, pyridine, pyridazine, pyrimidine, pyrazine, triazole, triazine, tetrazole, isoxazole, oxazole, oxadiazole, isothiazole, thiazole, thiadiazole, furan, thiophene and the like. 5- or 6-membered monocyclic aromatic heterocycle is especially preferable.

"Bicyclic aromatic heterocycle" means fused aromatic heterocycle that aromatic heterocycle (aromatic carbocycle derived from the above "aryl") or aromatic heterocycle (4- to 8-membered aromatic heterocycle containing one or more heteroatom(s) arbitrarily selected from O, S and N on the ring) is fused with the above "monocyclic aromatic heterocycle". Examples are indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyradinopyridazine, oxazoropyridine, thiazoropyridine and the like.

"Heteroaryl" means monocyclic or polycyclic aromatic heterocyclyl containing one or more heteroatom(s) arbitrarily selected from O, S and N on the ring. For example, the groups derived from the above "monocyclic aromatic heterocycle", the groups derived from the above "bicyclic aromatic heterocycle" and polycyclic heteroaryl having 3 or more rings are included. Examples of the groups derived from "monocyclic aromatic heterocyclyl" are pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like.

Examples of the groups derived from the above "bicyclic aromatic heterocyclyl" are indolyl, isoindolyl, indazolyl, indolizinyl, quinolyl, isoquinolyl, cinnolinyl, phthalazinyl, quinazolinyl, naphthyridinyl, quinoxalinyl, purinyl, pteridinyl, benzimidazolyl, benzisoxazolyl, benzoxazolyl, benbzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, oxazolopyridyl, thiazolopyridyl and the like. Examples of polycyclic heteroaryl having 3 or more rings are carbazolyl, acridinyl, xanthenyl, phenothiazinyl, phenoxathiinyl, phenoxazinyl, dibenzofuryl and the like. When "heteroaryl" means "polycyclic heteroaryl", the bond(s) can be attached to any of the rings.

"Heterocycle" means 4- to 8-membered monocyclic nonaromatic heterocycle containing one or more heteroatom(s) arbitrarily selected from O, S and N on the ring, or fused heterocycle that aromatic carbocyle (a ring derived from the above "aryl"), aromatic heterocycle (a ring derived from the above "heteroaryl"), monocyclic nonaromatic heterocycle (a ring derived from "monocyclic nonaromatic heterocyclyl") or cycloalkane (a ring derived from the above "cycloalkyl") is fused with "monocyclic nonaromatic heterocycle". Examples of monocyclic heterocycle are dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperazino, morpholinyl, morpholino, oxadiazinyl, dihydropyridyl, thiomorpholinyl, thiomorpholino, tetrahydrofuryl, tetrahydropyranyl, tetrahydrothiazolyl, tetrahydroisothiazolyl and the like. Examples of fused heterocycle are indolinyl, isoindolinyl, chromanyl, isochromanyl and the like.

"Alkoxy" means a group that the above "alkyl" is bonded to an oxygen atom. Examples are methoxy, ethoxy, n-propoxy, isopropoxy, n-butoxy, isobutoxy, sec-butoxy, tert-butoxy, n-pentoxy, pentoxy, neopentoxy, hexyoxy, isohexyoxy, n-heptoxy, isoheptoxy, n-oxtoxy, isooxtoxy and the like.

"Haloalkyl" and "haloalkoxy" means a group that the above "halogen" is bonded to the above "alkyl" and "alkoxy".

"Aryloxy" means a group that the above "aryl" is bonded to an oxygen atom. Examples are phenoxy, naphtoxy, anthryloxy, phenanthryloxy, indanyloxy, indenyloxy, biphenyloxy, acenaphthyloxy, tetrahydronaphthyloxy, fluorenyloxy and the like.

"Alkenyloxy", "cycloalkyloxy", "cycloalkenyloxy", "heteroaryloxy" or "heterocycleoxy" means a group that the above "alkenyl", "cycloalkyl", "cycloalkenyl", "heteroaryloxy" or "heterocycleoxy" is bonded to an oxygen atom.

"Alkylthio", "alkenylthio", "cycloalkylthio", "cycloalkenylthio", "arylthio", "heteroarylthio" or "heterocyclethio" means a group that the above "alkyl", "alkenyl", "cycloalkyl", "cycloalkenyl", "aryl", "heteroaryl" or "heterocycle" is bonded to a sulfur atom.

"Alkoxycarbonyl", "alkenyloxycarbonyl", "cycloalkyloxycarbonyl", "cycloalkenyloxycarbonyl", "aryloxycarbonyl", "heteroaryloxycarbonyl" or "heterocycleoxycarbonyl" means a group that an oxygen atom of the above "alkoxy", "alkenyloxy", "cycloalkyloxy", "cycloalkenyloxy", "aryloxy", "heteroaryloxy" or "heterocycleoxy" is bonded to carbonyl.

"Alkylcarbonyl", "alkenylcarbonyl", "cycloalkylcarbonyl", "cycloalkenylcarbonyl", "arylcarbonyl", "heteroarylcarbonyl" or "heterocyclecarbonyl" means a group that the above "alkyl", "alkenyl", "cycloalkyl", "cycloalkenyl", "aryl", "heteroaryl" or "heterocycle" is bonded to carbonyl.

"Alkylsulfonyl", "alkenylsulfonyl", "cycloalkylsulfonyl", "cycloalkenylsulfonyl", "arylsulfonyl", "heteroarylsulfonyl" or "heterocyclesulfonyl" means a group that the above "alkyl", "alkenyl", "cycloalkyl", "cycloalkenyl", "aryl", "heteroaryl" or "heterocycle" is bonded to sulfonyl.

Examples of the substituent of "substituted or unsubstituted alkyl", "substituted or unsubstituted alkenyl", "substituted or unsubstituted alkynyl", "substituted or unsubstituted alkoxy", "substituted or unsubstituted alkenyloxy", "substituted or unsubstituted alkylthio", "substituted or unsubstituted alkenylthio", "substituted or unsubstituted alkoxycarbonyl", "substituted or unsubstituted alkenyloxycarbonyl", "substituted or unsubstituted alkylcarbonyl", "substituted or unsubstituted alkenylcarbonyl", "substituted or unsubstituted alkylsulfonyl" or "substituted or unsubstituted alkenylsulfonyl" are halogen, cyano, nitro, nitroso, azide, acyl, acyloxy, imino, hydroxy, alkoxy, haloalkoxy, alkynyloxy, cycloalkyl, cycloalkyloxy, cycloalkenyl, cycloalkenyloxy, aryl, aryloxy, heteroaryl, heteroaryloxy, heterocyclyl, heterocyclyloxy, mercapto, alkylthio, alkenylthio, cycloalkylthio, cycloalkenylthio, arylthio, heteroarylthio, heterocyclethio, carboxy, alkoxycarbonyl, alkenyloxycarbonyl, cycloalkyloxycarbonyl, cycloalkenyloxycarbonyl, aryloxycarbonyl, heteroaryloxycarbonyl, heterocycleoxycarbonyl, carbamoyl, formyl, alkylcarbonyl, alkenylcarbonyl, cycloalkylcarbonyl, cycloalkenylcarbonyl, arylcarbonyl, heteroarylcarbonyl, heterocyclecarbonyl, sulfino, sulfo, alkylsulfonyl, alkenylsulfonyl, cycloalkylsulfonyl, cycloalkenylsulfonyl, arylsulfonyl, heteroarylsulfonyl, heterocyclesulfonyl, sulfamoyl, amino, oxo and the like. They can be substituted at arbitrary position(s) with one or more group(s) selected from the above.

Examples of the substituent of "substituted or unsubstituted cycloalkyl", "substituted or unsubstituted cycloalkenyl", "substituted or unsubstituted aryl", "substituted or unsubstituted heteroaryl", "substituted or unsubstituted heterocycleoxy", "substituted or unsubstituted cycloalkyloxy", "substituted or unsubstituted cycloalkenyloxy", "substituted or unsubstituted aryloxy", "substituted or unsubstituted heteroaryloxy", "substituted or unsubstituted heterocycleoxy", "substituted or unsubstituted cycloalkylthio", "substituted or unsubstituted cycloalkenylthio", "substituted or unsubstituted arylthio", "substituted or unsubstituted heteroarylthio", "substituted or unsubstituted heterocyclethio", "substituted or unsubstituted cycloalkyloxycarbonyl", "substituted or unsubstituted cycloalkenyloxycarbonyl", "substituted or unsubstituted aryloxycarbonyl", "substituted or unsubstituted heteroaryloxycarbonyl", "substituted or unsubstituted heterocycleoxycarbonyl", "substituted or unsubstituted carbamoyl", "substituted or unsubstituted cycloalkylcarbonyl", "substituted or unsubstituted cycloalkenylcarbonyl", "substituted or unsubstituted arylcarbonyl", "substituted or unsubstituted heteroarylcarbonyl", "substituted or unsubstituted heterocyclecarbonyl", "substituted or unsubstituted cycloalkylsulfonyl", "substituted or unsubstituted cycloalkenylsulfonyl", "substituted or unsubstituted arylsulfonyl", "substituted or unsubstituted heteroarylsulfonyl", "substituted or unsubstituted heterocyclesulfonyl", "substituted or unsubstituted sulfamoyl" or "substituted or unsubstituted amino" are alkyl, haloalkyl, alkenyl, alkynyl, halogen, cyano, nitro, nitroso, azide, acyl, acyloxy, imino, hydroxy, alkoxy, haloalkoxy, alkynyloxy, cycloalkyl, cycloalkyloxy, cycloalkenyl, cycloalkenyloxy, aryl, aryloxy, heteroaryl, heteroaryloxy, heterocycle, heterocycleoxy, mercapto, alkylthio, alkenylthio, cycloalkylthio, cycloalkenylthio, arylthio, heteroarylthio, heterocyclethio, carboxy, alkoxycarbonyl, alkenyloxycarbonyl, cycloalkyloxycarbonyl, cycloalkenyloxycarbonyl, aryloxycarbonyl, heteroaryloxycarbonyl, heterocycleoxycarbonyl, carbamoyl, formyl, alkylcarbonyl, alkenylcarbonyl, cycloalkylcarbonyl, cycloalkenylcarbonyl, arylcarbonyl, heteroarylcarbonyl, heterocyclecarbonyl, sulfino, sulfo, alkylsulfonyl, alkenylsulfonyl, cycloalkylsulfonyl, cycloalkenylsulfonyl, arylsulfonyl, heteroarylsulfonyl, heterocyclesulfonyl, sulfamoyl, amino, oxo, alkylene, alkylenedioxy, a group of the formula: —N(R$^6$)-(alkylene)-O—, a group of the formula: —N(R$^6$)-(alkylene)-N(R$^6$)- (wherein R$^6$ are each independently hydrogen or alkyl) and the like. When they are substituted with a bivalent group, the bonds of the bivalent group can be attached to the same atom or different atoms. The bonds of the bivalent group can be attached not only to the neighboring atoms but also to the atom(s) to form a bicyclo or spiro ring. They can be substituted at arbitrary position(s) with one or more group(s) selected from the above.

For example, when a substituent of "substituted or unsubstituted cycloalkyl (e.g, cyclohexyl)" is alkylene (e.g., —CH$_2$—CH$_2$—), the cycloalkyl can be one of the followings.

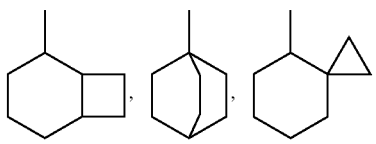

For example, when a substituent of "substituted or unsubstituted aryl" is alkylenedioxy, the aryl can be one of the followings.

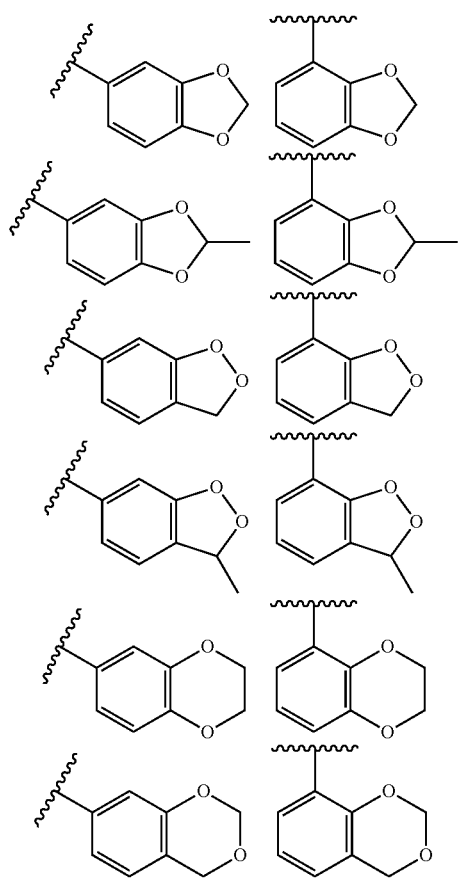

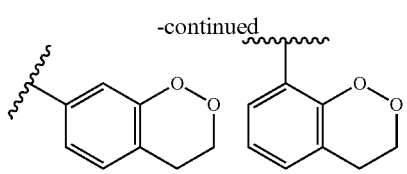

For example, when a substituent of "substituted or unsubstituted aryl" is a group of the formula: —N(R$^6$)-(alkylene)-O—, the aryl can be one of the followings.

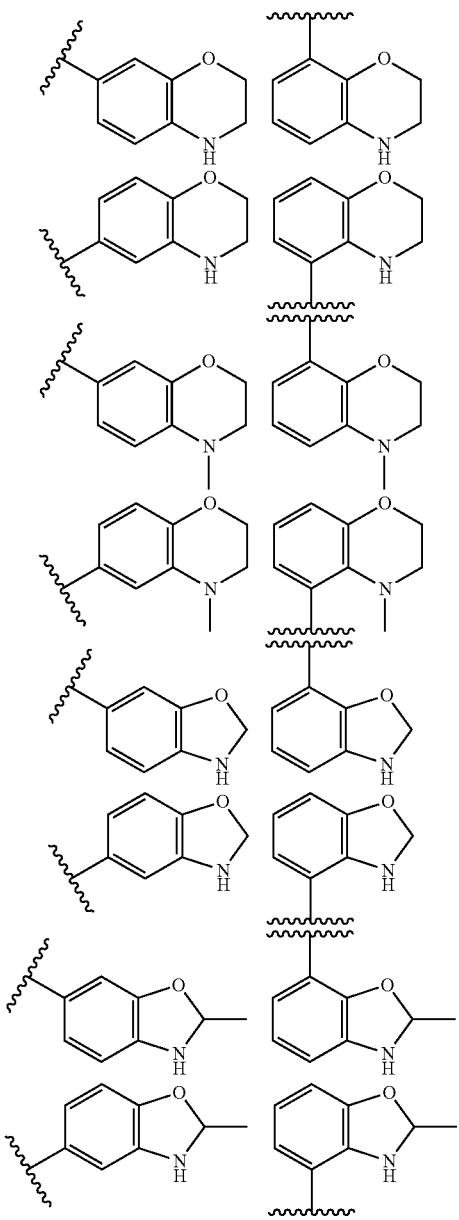

When a substituent is one of the other bivalent groups, it can be substituted as the above.

"Acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like.

"Acyloxy" means a group that the above "acyl" is bonded to an oxygen atom.

The following compounds are preferable as a compound of the formula (I).

$R^1$ is substituted or unsubstituted alkyl, substituted or unsubstituted alkenyl or substituted or unsubstituted alkynyl. Preferred is substituted or unsubstituted alkyl. More preferred is C1 to C10 unsubstituted alkyl. Preferable examples are ethyl isopropyl or t-butyl. Especially preferable examples are isopropyl or t-butyl.

$R^2$ is hydrogen or substituted or unsubstituted alkyl. Preferred is C1 to C3 alkyl or hydrogen. Especially preferred is hydrogen.

R is halogen, oxo, cyano, nitro, substituted or unsubstituted alkyl, substituted or unsubstituted alkenyl or substituted or unsubstituted alkynyl.

p is an integer between 0 and 2.

Ring A is monocyclic or bicyclic aromatic heteroaryl. Preferred is indole, pyrrolopyridine, pyrrolopyrimidine, pyrrolopyrazine, imidazole, pyrazole, pyrrole, triazole or pyridine. Especially preferred is indole, pyrrolopyridine, pyrrolopyrimidine, pyrrolopyrazine, pyrazole or pyrrole.

Examples of Ring A are a group selected from the followings.

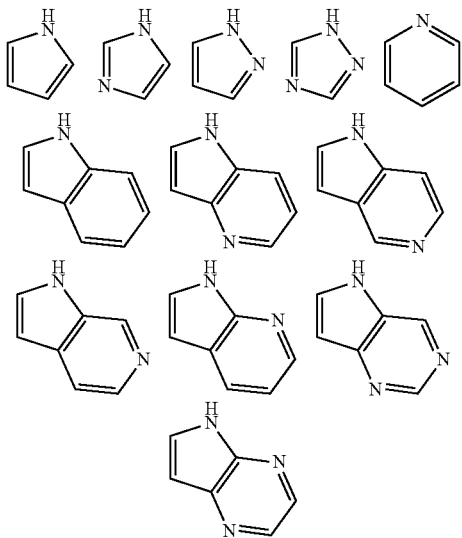

In the above scheme, the bonds from cyclohexane, $(R^3)m$ and $(R^4)n$ can be attached to any atom(s) on the above each ring.

Monocyclic or bicyclic aromatic heterocycle wherein one of the atoms next to the atom bonded to cyclohexyl is NH, is also preferable as Ring A.

This means that a group of the formula:

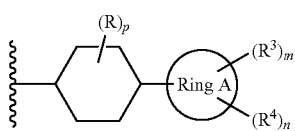

is preferably a group of the formula:

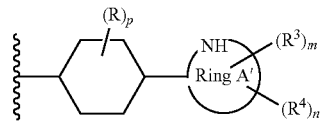

wherein Ring A' is monocyclic or bicyclic aromatic heterocycle.

$R^3$ is substituted or unsubstituted aryl, substituted or unsubstituted heteroaryl or substituted or unsubstituted heterocyclyl. Especially preferred is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted inorpholinyl, substituted or unsubstituted morpholino, substituted or unsubstituted pyrrolidinyl, substituted or unsubstituted piperidyl, substituted or unsubstituted piperidino, substituted or unsubstituted benzodioxolyl, substituted or unsubstituted dihydrobenzoxazinyl or substituted or unsubstituted indazolyl.

When $R^3$ has a substituent(s), the preferable substituent(s) is 1, 2 or more group(s) selected from halogen, cyano, nitro, nitroso, azide, oxo, alkyl, haloalkyl, alkenyl, alkynyl, hydroxy, alkoxy, haloalkoxy, alkenyloxy, mercapto, alkylthio, alkenylthio, carboxy, alkoxycarbonyl, alkenyloxycarbonyl, carbamoyl, formyl, alkylcarbonyl, alkenylcarbonyl, sulfino, sulfo, alkylsulfonyl, alkenylsulfonyl, sulfamoyl, aminoalkylenedioxy, morpholino or a group of the formula: —N($R^6$)-(alkylene)-O—.

$R^4$ is halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl, hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heteroaryloxy, substituted or unsubstituted heterocyclyloxy, mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclylthio, carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heteroaryloxycarbonyl, substituted or unsubstituted heterocyclyloxycarbonyl, substituted or unsubstituted carbamoyl, formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclylsulfonyl, substituted or unsubstituted sulfamoyl, or substituted or unsubstituted amino.

Especially preferred is halogen, cyano, oxo, substituted or unsubstituted alkyl, substituted or unsubstituted cycloalkyl, substituted or unsubstituted alkoxy, or substituted or unsubstituted aryloxy.

When $R^4$ has a substituent(s), a preferable substituent(s) is 1, 2 or more group(s) selected from halogen, cyano, nitro, nitroso, azide, oxo, alkyl, haloalkyl, alkenyl, alkynyl, hydroxy, alkoxy, haloalkoxy, alkenyloxy, mercapto, alkylthio, alkenylthio, carboxy, alkoxycarbonyl, alkenyloxycarbonyl, carbamoyl, formyl, alkylcarbonyl, alkenylcarbonyl, sulfino, sulfo, alkylsulfonyl, alkenylsulfonyl, sulfamoyl or amino.

m is an integer between 0 and 2. Especially preferred is 1.
n is an integer between 0 and 5. Especially preferred is 0 or 1.

When Ring A is indole, pyrrolopyridine, pyrrolopyrimidine, pyrrolopyrazine, pyrrole, triazole or pyridine, $R^3$, $R^4$, m and n are preferably as below.

$R^3$ is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted morpholinyl, substituted or unsubstituted morpholino, substituted or unsubstituted pyrrolidinyl, substituted or unsubstituted piperidyl, or substituted or unsubstituted piperidino. A preferred substituent(s) is 1, 2 or more group(s) selected from halogen, cyano, nitro, azide, oxo, alkyl, haloalkyl, alkenyl, alkynyl, hydroxy, alkoxy or haloalkoxy.

Especially preferable $R^3$ is substituted or unsubstituted phenyl (wherein the substituent is halogen and/or cyano), substituted or unsubstituted pyridyl (wherein the substituent is halogen), pyrimidinyl, pyrazinyl, thiazolyl, oxazolyl, substituted or unsubstituted morpholinyl (wherein the substituent is alkyl), substituted or unsubstituted morpholino (wherein the substituent is alkyl), pyrrolidinyl, piperidyl or piperidino.

$R^4$ is halogen, cyano, oxo, substituted or unsubstituted alkyl, substituted or unsubstituted alkoxy, or substituted or unsubstituted aryloxy. A preferable substituent(s) is 1, 2 or more group(s) selected from halogen, cyano, nitro, azide, oxo, alkyl, haloalkyl, alkenyl, alkynyl, hydroxy, alkoxy or haloalkoxy.

Especially preferable $R^4$ is halogen, cyano, alkyl, haloalkyl, alkoxy, haloalkoxy or aryloxy.

m is an integer between 0 and 2. Especially preferred is 1.
n is an integer between 0 and 5. Especially preferred is 0 or 1.

When Ring A is imidazole, especially preferred is as below.
A compound of the formula (I-2):

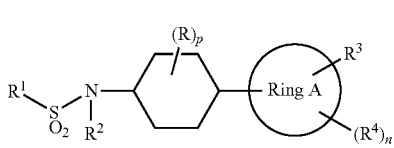

(I-2)

wherein Ring A is imidazole, and each of the other symbols has the same meaning as that of a compound of the formula (I).

A compound of the formula (II-1):

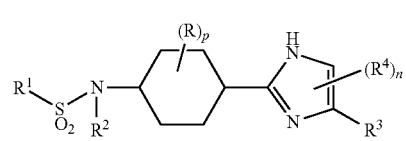

(II-1)

wherein each symbol has the same meaning as that of a compound of the formula (I). $R^4$ can be attached to NH of imidazole.

In the above formula (I-2), $R^3$, $R^4$ and n are especially preferable as below.

$R^3$ is substituted or unsubstituted phenyl, substituted or unsubstituted pyridyl, substituted or unsubstituted morpholinyl, substituted or unsubstituted benzodioxolyl, substituted or unsubstituted dihydrobenzoxazinyl, or substituted or unsubstituted indazolyl. A preferable substituent(s) is 1, 2 or more group(s) selected from halogen, cyano, nitro, azide, oxo, alkyl, haloalkyl, alkenyl, alkynyl, hydroxy, alkoxy, haloalkoxy, alkylenedioxy, morpholino or a group of the formula: —N($R^6$)-(alkylene)-O—.

Especially preferable $R^3$ is substituted or unsubstituted phenyl (wherein the substituent(s) is 1, 2 or more the group(s) selected from halogen, cyano, alkyl, haloalkyl, alkoxy, haloalkoxy, alkylenedioxy, morpholino or a group of the formula: —N($R^6$)-(alkylene)-O—), substituted or unsubstituted pyridyl (wherein the substituent is halogen), morpholinyl, benzodioxolyl, substituted or unsubstituted dihydrobenzoxazinyl (wherein the substituent is alkyl) or substituted or unsubstituted indazolyl (wherein the substituent is alkyl).

$R^4$ is halogen, substituted or unsubstituted alkyl or substituted or unsubstituted cycloalkyl. A preferable substituent(s) is 1, 2 or more group(s) selected from halogen, cyano, nitro, azide, oxo, alkyl, haloalkyl, alkenyl, alkynyl, hydroxy, alkoxy or haloalkoxy.

Especially preferable $R^4$ is halogen, substituted or unsubstituted alkyl (wherein the substituent(s) is hydroxyl and/or halogen) or cycloalkyl.

n is an integer between 0 and 2. Especially preferred is 1.
When Ring A is pyrazole, especially preferred is as below.
A compound of the formula (I-2):

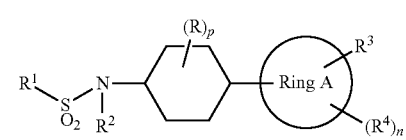

(I-2)

wherein Ring A is pyrazole, and each of the other symbols has the same meaning as that of a compound of the formula (I).

A compound of the formula (II-2):

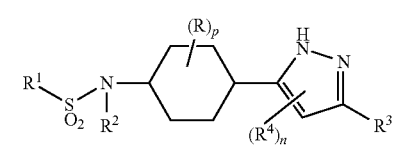

(II-2)

wherein each symbol has the same meaning as that of a compound of the formula (I). $R^4$ can be attached to NH of imidazole.

In the above formula (I-2), $R^3$, $R^4$ and n are especially preferable as below.

$R^3$ is substituted or unsubstituted phenyl or substituted or unsubstituted pyridyl. A preferable substituent(s) is 1, 2 or more group(s) selected from halogen, cyano, nitro, azide, oxo, alkyl, haloalkyl, alkenyl, alkynyl, hydroxy, alkoxy or haloalkoxy.

Especially preferable $R^3$ is substituted or unsubstituted phenyl (wherein the substituent(s) is 1, 2 or more group(s) selected from halogen, cyano or alkoxy) or pyridyl.

$R^4$ is halogen, cyano or substituted or unsubstituted alkyl. A preferable substituent(s) is 1, 2 or more group(s) selected from halogen, cyano, nitro, azide, oxo, alkyl, haloalkyl, alkenyl, alkynyl, hydroxy, alkoxy or haloalkoxy.

Especially preferable $R^4$ is halogen, cyano or alkyl.

n is an integer between 0 and 2. Especially preferred is 1.

A compound of the formula (I) is a group of the formula:

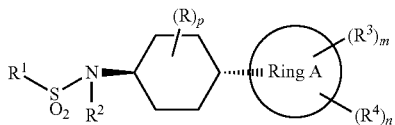

wherein each symbol has the same meaning as that of a compound of the formula (I),
or a compound of the formula:

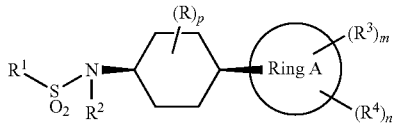

wherein each symbol has the same meaning as that of a compound of the formula (I). Especially preferred is a compound of the formula:

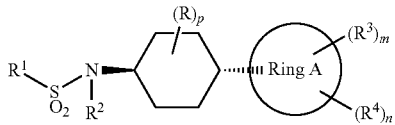

wherein each symbol has the same meaning as that of a compound of the formula (I).

The above compound can be shown as below.

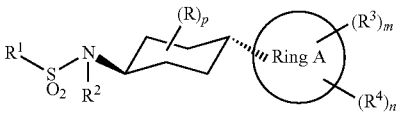

In the above scheme, each symbol has the same meaning as that of a compound of the formula (I).

The compounds of this invention include any pharmaceutically acceptable salts thereof which can be produced. Examples of "the pharmaceutically acceptable salt" are salts with inorganic acid such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of this invention include any solvates thereof. Preferred is hydrate and any number of water molecules may be coordinated with the compound of this invention.

When a compound of this invention has an asymmetric carbon atom, racemates, all of enantiomers and all of stereoisomers such as diastereomer, epimer and enantiomer thereof are within the scope of this invention. When a compound of this invention having one or more double bonds forms an E isomer or Z isomer, both isomers are within the scope of this invention.

This invention includes within its scope prodrugs of the compounds in pharmaceutical compositions of this invention. In general, such prodrugs will be functional derivatives of the compounds which are readily convertible in vivo into the required compound. Thus, "a compound" of this invention shall encompass compounds specifically disclosed or compounds which may not be specifically disclosed, but which convert to the specified compounds in vivo after administration to the patient with a disease associated with NPY Y5. Conventional procedures for the selection and preparation of suitable prodrug derivatives are described, for example, in Design of Prodrugs (ed. H. Bundgaard, Elsevier, 1985).

For example, compounds of the formula (I) of this invention can be prepared by the following methods.

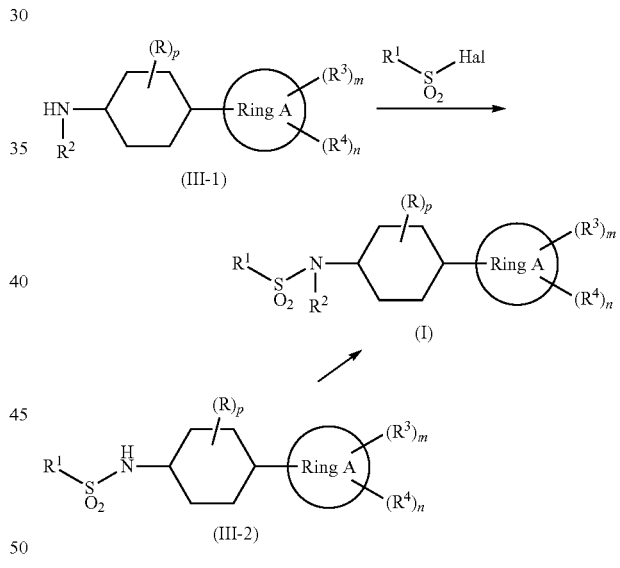

Compound of the formula: $R^1SO_2Hal$ wherein $R^1$ is the same as that of a compound of the formula (I) and Hal is halogen, is reacted with Compound of the formula (III-1) to give Compound of the formula (I). Alternatively, Compound of the formula: $R^2Hal$ wherein $R^2$ is the same as that of a compound of the formula (I) and Hal is halogen, is reacted with Compound of the formula (III-2) to give Compound of the formula (I).

The above reaction can be carried with base. Examples of the base are pyridine, triethylamine, N-methylmorpholine, dimethylaniline, barium hydroxide, sodium hydroxide, potassium hydroxide, sodium hydride and the like.

The above reaction may be carried out within the range of 0° C. to 50° C. for several minutes to several hours. Examples of the reaction solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixtures thereof and the like.

The above reaction can be carried out after protecting $R^3$ or $R^4$ on Ring A, and then the deprotection can be carried out after the reaction.

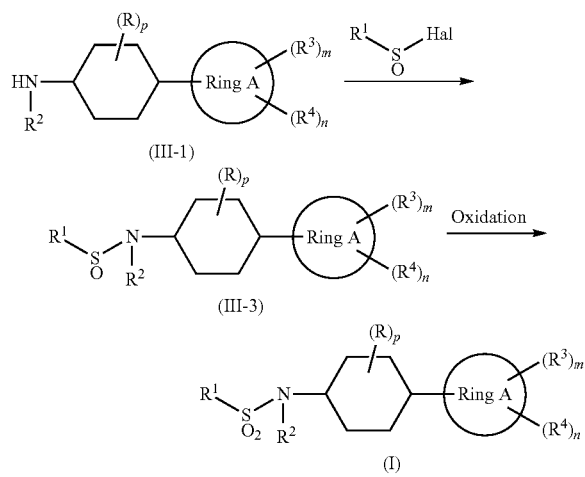

Compound of the formula: $R^1SOHal$ wherein $R^1$ is the same as that of a compound of the formula (I) and Hal is halogen, is reacted with Compound of the formula (III-1) to give Compound of the formula (III-3). The obtained Compound of the formula (III-3) is oxidized to give Compound of the formula (I).

The step with Compound of the formula: $R^1SOHal$ can be carried out under the presence of the base. Examples of the base are pyridine, triethylamine, N-methylmorpholine, dimethylaniline, barium hydroxide, sodium hydroxide, potassium hydroxide and the like.

The above reaction may be carried out within the range of 0° C. to 50° C. for several minutes to several hours. Examples of the reaction solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixtures thereof and the like.

The oxidation step can be carried out with an oxidant. Examples of the oxidant are m-chloroperbenzoic acid, acetyl hydroperoxide, hydrogen peroxide, trifluoroperacetic acid, sodium periodate, sodium hypochlorite, potassium permanganate, sodium tungstate and the like.

The above reaction can be carried out after protecting $R^3$ or $R^4$ on Ring A, and then the deprotection can be carried out after the reaction.

The following synthesis method can be used to give a compound of the formula (I) when Ring A of the compound is suitable to the method.

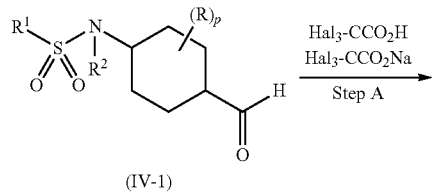

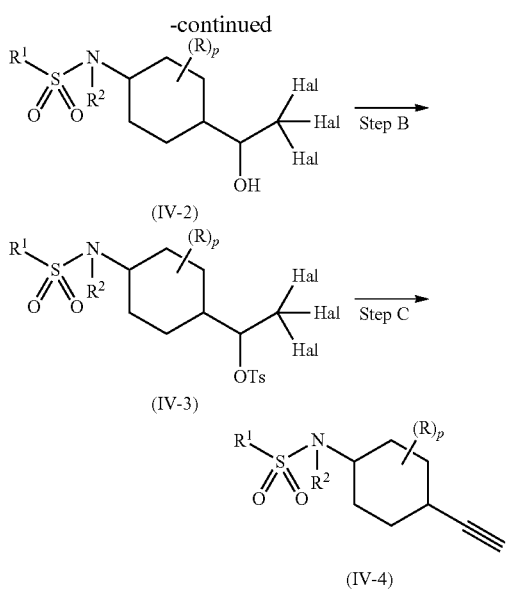

In the above scheme, Hal is halogen and each symbol has the same meaning as that of a compound of the formula (I).

Step A

Compound of the formula (IV-1) having the desired substituent $R^1$ and $R^2$ which can be synthesized by the method disclosed in WO2007/125952 is reacted with trihaloacetic acid and its sodium salt in an appropriate solvent within the range of 0° C. to 50° C. for several minutes to several hours to give Compound of the formula (IV-2).

Examples of the reaction solvent are tetrahydrofuran, dimethylformamide, dimethylacetamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water and mixtures thereof and the like. Preferred is dimethylformamide.

Step B

Compound of the formula (IV-2) is reacted with sulfonyl halide in an appropriate solvent under the presence of the base to give Compound of the formula (IV-3). The reaction can be carried out within the range of 0° C. to 100° C. for several minutes to several hours.

Examples of the sulfonyl halide are p-toluenesulfonyl chloride, benzenesulfonyl chloride, methansulfonyl chloride, trifluoromethansulfonyl chloride and the like.

Examples of the base are triethylamine, pyridine, N-methylmorpholine, dimethylaniline, barium hydroxide, sodium hydroxide, potassium hydroxide and the like. Preferred is triethylamine. The amount of the base is preferably 1 to 5 equivalent(s) to Compound of the formula (IV-2).

Examples of the reaction solvent are methylene chloride, tetrahydrofuran, dimethylformamide, dimethylacetamide, N-methylpyrrolidone, diethyl ether, 1,2-dichloroethane, toluene, benzene, xylene, cyclohexane, hexane, chloroform, ethyl acetate, butyl acetate, pentane, heptane, dioxane, acetone, acetonitrile, mixtures thereof and the like. Preferred is methylene chloride.

Examples of the catalyst are DABCO (1,4-Diazabicyclo[2,2,2]octane), HCl, $H_2SO_4$, acetic acid, $CF_3COOH$, toluenesulfonic acid, p-toluenesulfonic acid and the like. Preferred is DABCO.

Step C

Compound of the formula (IV-3) is treated with the base in an appropriate solvent to give Compound of the formula (IV-4). The reaction can be carried out within the range of −50° C. to 50° C. for several minutes to several hours.

Examples of the base are n-butyllithium, sec-butyllithium, ter-butyllithium, methyllithium, hydrazine, the lithium salt of propanethiol and the like. Preferred is the strong base, for example, n-butyllithium and the like.

Examples of the reaction solvent are methylene chloride, tetrahydrofuran, diethyl ether, toluene, benzene, xylene, cyclohexane, hexane, pentane, heptane, dioxane, acetone and the like. Preferred are tetrahydrofuran and/or hexane.

When Ring A is indole, compounds of this invention can be synthesized as below.

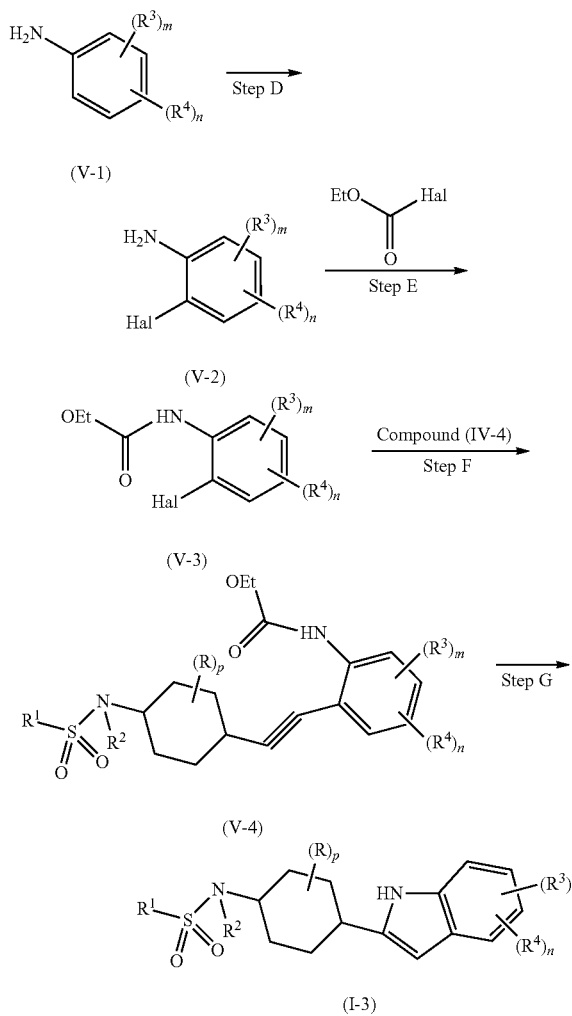

In the above scheme, Hal is halogen and each of the other symbols has the same meaning as that of a compound of the formula (I).

Step D

To Compound of the formula (V-1), is added N-bromosuccinimide in an appropriate solvent to give Compound of the formula (V-2). The reaction can be carried out within the range of −50° C. to room temperature for several minutes to several hours.

Examples of the reaction solvent are tetrahydrofuran, dimethylformamide, dichloromethane, toluene, benzene, xylene, cyclohexane, chloroform, ethyl acetate, butyl acetate, pentane, heptane, dioxane, aceton, methanol, ethanol, acetonitrile, water, mixtures thereof and the like. Preferred are dichloromethane and/or methanol.

Step E

To Compound of the formula (V-2), is added halogeno ethyl carbonate in an appropriate solvent to give Compound of the formula (V-3). The reaction can be carried out within the range of 0° C. to 100° C. for several minutes to several hours.

Examples of the reaction solvent are tetrahydrofuran, dimethylformamide, dimethylacetamide, N-methylpyrrolidone, diethyl ether, dichloromethane, toluene, benzene, pyridine, xylene, cyclohexane, hexane, chloroform, ethyl acetate, butyl acetate, pentane, heptane, dioxane, aceton, methanol, ethanol, acetonitrile, water, mixtures thereof and the like. The reaction can be carried out without the solvent. Preferred are tetrahydrofuran and/or pyridine.

The reaction can be carried out under the presence of the base. Examples of the base are pyridine, N-methylmorpholine, dimethylaniline and the like.

Step F

Compound of the formula (V-3) and Compound of the formula (IV-4) are reacted in an appropriate solvent under the presence of the base to give Compound of the formula (V-4). The reaction can be carried out within the range of 0° C. to 100° C. for several minutes to several hours.

Examples of the base are triethylamine, DBU, sodium carbonate, potassium carbonate barium hydroxide, sodium hydroxide, potassium hydroxide and the like. Preferred is triethylamine, potassium carbonate or the like.

Examples of the reaction solvent are tetrahydrofuran, dimethylformamide, dimethylacetamide, diethyl ether, dichloromethane, toluene, benzene, xylene, cyclohexane, hexane, chloroform, ethyl acetate, butyl acetate, pentane, heptane, dioxane, aceton, methanol, ethanol, propanol, acetonitrile, water, mixtures thereof and the like. Preferred is dimethylformamide.

Examples of the catalyst are Pd(PPh3)4 (tetrakistriphenyl phosphine palladium), PdCl2(PPh3)2 (dichlorobis triphenyl phosphinepalladium), Pd(DBA) (bis dibenzylidineacetonpalladium), copper iodide, DABCO and the like. Preferred are dichlorobis triphenyl phosphinepalladium and/or copper iodide.

Step G

Compound of the formula (V-4) is treated with the base in an appropriate solvent to give Compound of the formula (I-3). The reaction is carried out within the range of 0° C. to 100° C. for several minutes to several hours.

Examples of the base are tetrabutylammonium fluoride, triethylamine, pyridine, N-methylmorpholine, dimethylaniline, barium hydroxide, sodium hydroxide, potassium hydroxide, potassium carbonate sodium carbonate, hydrazine, the lithium salt of propanethiol and the like. Preferred is tetrabutylammonium fluoride.

Examples of the reaction solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is tetrahydrofuran.

When Ring A is pyrrolopyrimidine, compounds of this invention can be synthesized as below.

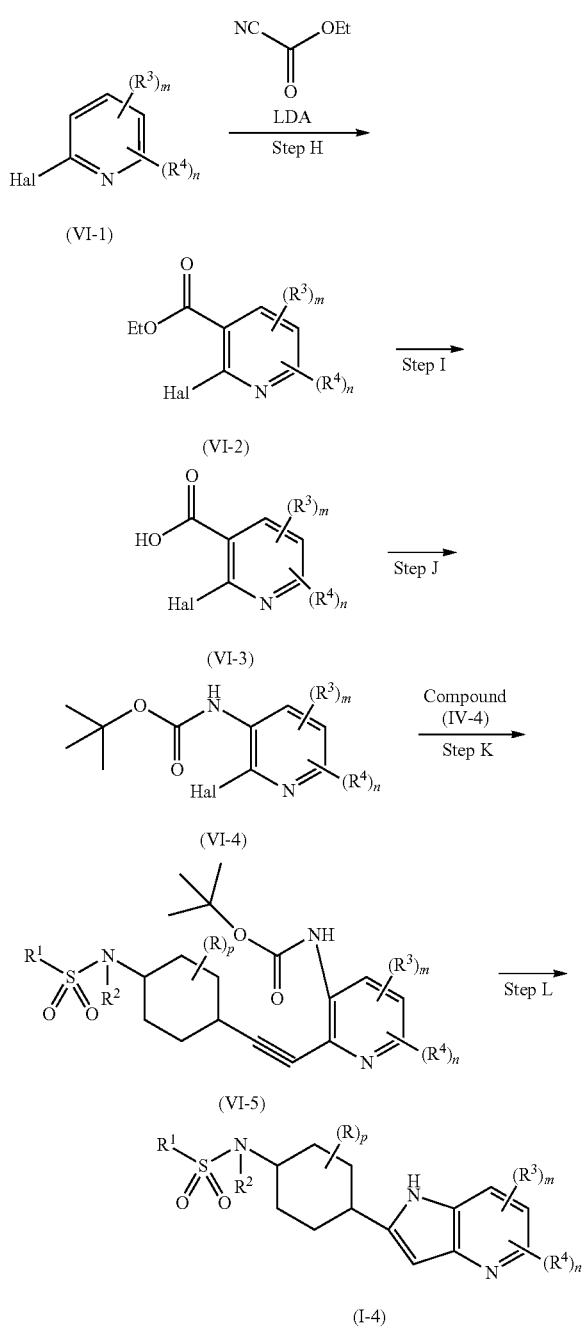

In the above scheme, Hal is halogen and each of the other symbols has the same meaning as that of a compound of the formula (I).

Step H

Compound of the formula (VI-1) and cyano ethyl formate are reacted in an appropriate solvent under the presence of the base to give Compound of the formula (VI-2). The reaction can be carried out within the range of −100° C. to 0° C. for several minutes to several hours.

Examples of the base are lithium diisopropylamine, lithium tetramethylpiperidide, n-butyllithium, sec-butyllithium, ter-butyllithium, methyllithium, methyllithium and the like. Preferred is lithium diisopropylamine.

Examples of the reaction solvent are tetrahydrofuran, diethyl ether, toluene, benzene, xylene, cyclohexane, hexane, pentane, heptane, dioxane, mixtures thereof and the like. Preferred is tetrahydrofuran.

Step I

Compound of the formula (VI-2) is treated with the base in an appropriate solvent to give Compound of the formula (VI-3). The reaction can be carried out within the range of 0° C. to 50° C. for several minutes to several hours.

Examples of the base are barium hydroxide, sodium hydroxide, potassium hydroxide, lithium hydroxide and the like. Preferred is sodium hydroxide.

Examples of the reaction solvent are tetrahydrofuran, dimethylformamide, diethyl ether, dichloromethane, toluene, benzene, xylene, cyclohexane, hexane, chloroform, pentane, heptane, dioxane, aceton, methanol, ethanol, acetonitrile, water, mixtures thereof and the like. Preferred is ethanol.

Step J

Compound of the formula (VI-3) is treated with the base in an appropriate solvent and then reacted with diphenyl phosphate azide to give Compound of the formula (VI-4). The reaction can be carried out within the range of 0° C. to 100° C. for several minutes to several hours.

Examples of the base are diisopropylamine, triethylamine, dimethylamino pyridine and the like. Preferred is triethylamine.

Examples of the reaction solvent are tetrahydrofuran, dimethylformamide, diethyl ether, dichloromethane, toluene, benzene, xylene, chloroform, dioxane, aceton, acetonitrile, buthanol, mixtures thereof and the like. Preferred is t-buthanol.

Step K

Compound of the formula (VI-4) and Compound of the formula (IV-4) are reacted in an appropriate solvent under the presence of the base to give Compound of the formula (VI-5). The reaction can be carried out within the range of 0° C. to 100° C. for several minutes to several hours. The reaction condition is the same as Step F.

Step L

Compound of the formula (VI-5) is treated with the base in an appropriate solvent to give Compound of the formula (I-4). The reaction can be carried out within the range of 0° C. to 100° C. for several minutes to several hours.

Examples of the base are 1,8-diazabicyclo[5,4,0]-7-undecene, tetrabutylammonium fluoride, triethylamine, pyridine, N-methylmorpholine, dimethylaniline, metalalkoxide and the like. Preferred is 1,8-diazabicyclo[5,4,0]-7-undecene.

Examples of the reaction solvent are tetrahydrofuran, dimethylformamide, diethyl ether, dichloromethane, toluene, benzene, xylene, cyclohexane, hexane, chloroform, heptane, dioxane, aceton, methanol, ethanol, acetonitrile, water, mixtures thereof and the like. Preferred are methanol and/or water.

Compounds of the formula (I) having various bicyclic aromatic heterocycle in Ring A can be synthesized by using compounds having the nitrogen atom(s) whose position and/or number are different from those of the Compounds of the formula (VI-1), (VI-2), (VI-3), (VI-4) and (VI-5) in the above Step H to L.

When Ring A is pyrrole, compounds of this invention can be synthesized as below.

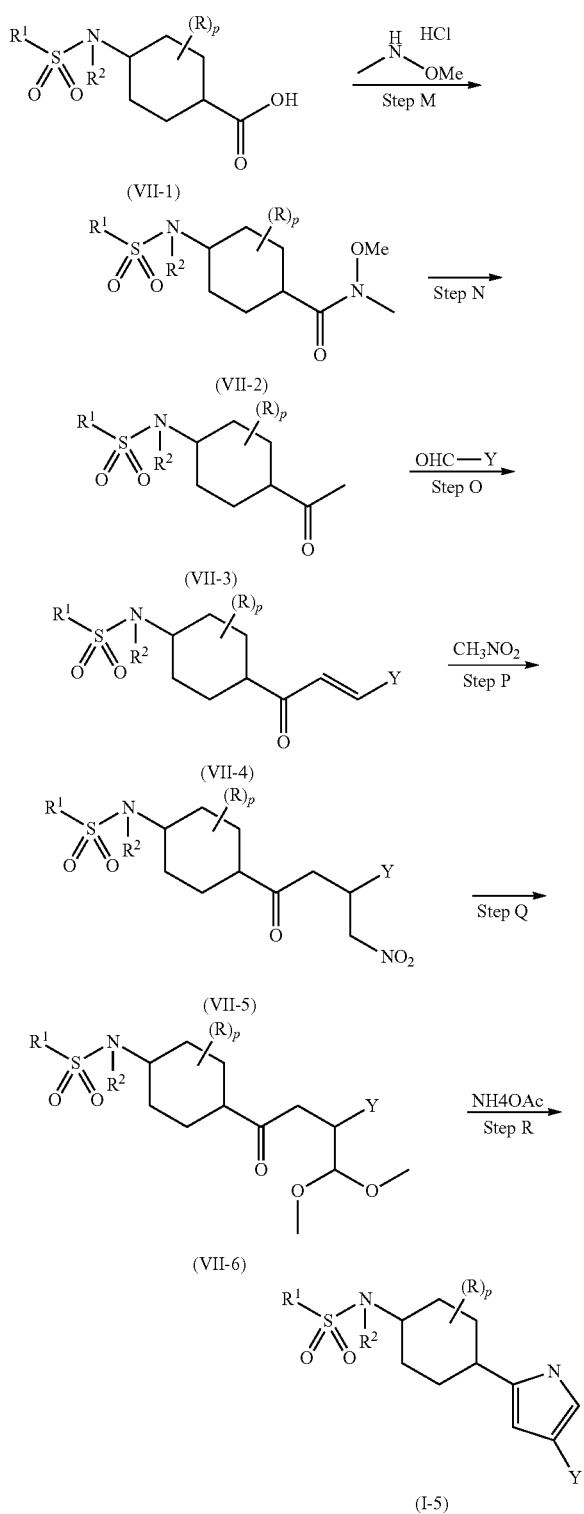

0° C. to 50° C. for several minutes to several hours to form acid halide. N,O-dimethylhydroxyamine hydrochloride is added to the solution and reacted in an appropriate solvent under the presence of the base at 0° C. to 50° C. for several minutes to several hours to give Compound of the formula (VII-2).

Examples of the dehydrating agent are oxalyl chloride, thionylchloride, phosphorus pentachloride, phosphorus oxychloride, acetic anhydride, methansulfonyl chloride, ethyl chlorocarbonate and the like. Preferred is oxalyl chloride. The amount of the dehydrating agent is preferably 1 to 5 equivalent(s) to Compound of the formula (VII-1). As a catalyst, dimethylformamide can be added.

Examples of the base are triethylamine, pyridine, N-methylmorpholine, dimethylaniline, potassium carbonate sodium carbonate, barium hydroxide, sodium hydroxide, potassium hydroxide and the like. Preferred is triethylamine.

Examples of the reaction solvent are methylene chloride, tetrahydrofuran, dimethylformamide, dimethylacetamide, N-methylpyrrolidone, diethyl ether, 1,2-dichloroethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is methylene chloride and/or dimethylformamide.

Step N

Compound of the formula (VII-2) is treated with a methylating agent in an appropriate solvent to give Compound of the formula (VII-3). The reaction can be carried out within the range of –80° C. to 100° C. for several minutes to several hours.

Examples of the methylating agent are methylmagnesium bromide, methylmagnesium chloride, methylmagnesium iodide and methyllithium. Preferred is methylmagnesium bromide or methylmagnesium chloride. The amount of Grignard reagent is preferably 1 to 5 equivalent(s) to Compound of the formula (VII-2).

Examples of the reaction solvent are tetrahydrofuran, diethyl ether, toluene, benzene, xylene, cyclohexane, hexane, pentane, heptane, dioxane, mixtures thereof and the like. Preferred are tetrahydrofuran and/or diethyl ether.

Step O

Compound of the formula (VII-3) and aldehyde having the desired substituent $R^3$ are treated with the base in an appropriate solvent to give Compound of the formula (VII-4). The reaction can be carried out within the range of 0° C. to 100° C. for several minutes to several hours.

Examples of the base are triethylamine, pyridine, dimethylaniline, barium hydroxide, sodium hydroxide, potassium hydroxide, butyllithium, LDA, sodium methoxide and the like. Preferred is sodium hydroxide.

Examples of the reaction solvent are methylene chloride, tetrahydrofuran, dimethylformamide, dimethylacetamide, N-methylpyrrolidone, diethyl ether, 1,2-dichloroethane, toluene, benzene, xylene, cyclohexane, hexane, pentane, heptane, dioxane, methanol, ethanol, acetonitrile, water, mixtures thereof and the like. Preferred is methanol.

Step P

Compound of the formula (VII-4) and nitro methane are treated with the base in an appropriate solvent to give Compound of the formula (VII-5). The reaction can be carried out within the range of 0° C. to 100° C. for several minutes to several hours.

Examples of the base are tetrabutylammonium fluoride, potassium fluoride, cesium fluoride, diethylamine, triethy- In the above scheme, Y is $R^3$ or $R^4$ of Compound of the formula (I) or hydrogen. Each of the other symbols has the same meaning as that of a compound of the formula (I).

Step M

Compound of the formula (VII-1) having the desired substituent $R^1$ and $R^2$ which can be synthesized by a method disclosed in WO2001/037826 is treated with a dehydrating agent in an appropriate solvent and reacted within the range of lamine, pyridine, dimethylaniline, barium hydroxide, sodium hydroxide, potassium hydroxide and the like. Preferred is diethylamine.

Examples of the reaction solvent are methylene chloride, tetrahydrofuran, dimethylformamide, diethyl ether, dichloromethane, toluene, benzene, xylene, cyclohexane, hexane, ethyl acetate, butyl acetate, pentane, heptane, dioxane, aceton, methanol, ethanol, acetonitrile, water, mixtures thereof and the like. Preferred is methanol.

Step Q

Compound of the formula (VII-5) is treated with the base in an appropriate solvent within the range of 0° C. to 100° C. for several minutes to several hours, treated with methanol within the range of 0° C. to 65° C. for several minutes to several hours and then treated with the acid to give Compound of the formula (VII-6).

Examples of the base are diethylamine, triethylamine, pyridine, N-methylmorpholine, dimethylaniline, barium hydroxide, sodium hydroxide, potassium hydroxide and the like. Preferred is potassium hydroxide.

Examples of the acid are concentrated hydrochloric acid, concentrated sulphuric acid, concentrated nitric acid and the like. Preferred is concentrated sulphuric acid.

Examples of the reaction solvent are methylene chloride, tetrahydrofuran, dimethylformamide, diethyl ether, 1,2-dichloroethane, toluene, benzene, xylene, cyclohexane, hexane, chloroform, ethyl acetate, butyl acetate, pentane, heptane, dioxane, aceton, methanol, ethanol, propanol, acetonitrile, water, mixtures thereof and the like. Preferred are methanol and/or tetrahydrofuran.

Step R

Compound of the formula (VII-6) is reacted with ammonium acetate in an appropriate solvent to give Compound of the formula (I-5). The reaction can be carried out within the range of room temperature to 150° C. for several minutes to several hours.

Examples of the reaction solvent are acetic acid, methylene chloride, tetrahydrofuran, dimethylformamide, dimethylacetamide, N-methylpyrrolidone, diethyl ether, diisopropyl ether, 1,2-dichloroethane, toluene, benzene, xylene, cyclohexane, hexane, chloroform, ethyl acetate, butyl acetate, pentane, heptane, dioxane, aceton, methanol, ethanol, propanol, acetonitrile, water, mixtures thereof and the like. Preferred is acetic acid.

When Ring A is imidazole, compounds of this invention can be synthesized as below.

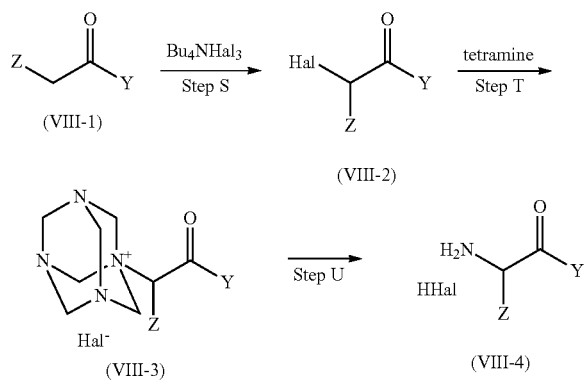

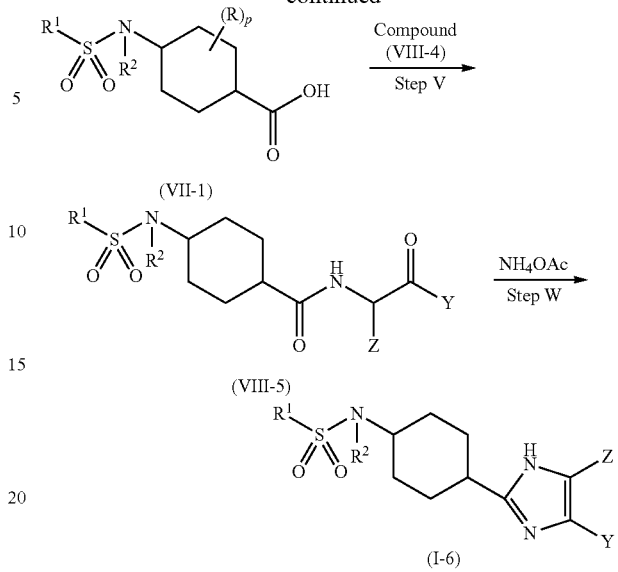

In the above scheme, Hal is halogen, Y and Z is $R^3$ or $R^4$ of a compound of the formula (I) or hydrogen. Either Y or Z is $R^3$. Each of the other symbols has the same meaning as that of a compound of the formula (I).

Step S

Compound of the formula (VIII-1) having the desired substituent $R^3$ and tetrabutyl ammonium halide are reacted in an appropriate solvent within the range of 100° C. to 200° C. (if necessary, by a microwave reactor) for several minutes to several hours to give Compound of the formula (VIII-2).

Examples of the reaction solvent are acetic acid, methylene chloride, tetrahydrofuran, diethyl ether, dichloromethane, toluene, benzene, xylene, cyclohexane, hexane, chloroform, ethyl acetate, butyl acetate, pentane, heptane, dioxane, methanol, ethanol, acetonitrile, mixtures thereof and the like. Preferred is acetonitrile.

Step T

Compound of the formula (VIII-2) is reacted with hexamethylenetetramine in an appropriate solvent to give Compound of the formula (VIII-3). The reaction can be carried out within the range of room temperature to 100° C. for several minutes to several hours.

Examples of the reaction solvent are acetic acid, methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, mixtures thereof and the like. Preferred is chloroform.

Step U

Compound of the formula (VIII-3) is reacted with the acid in an appropriate solvent to give Compound of the formula (VIII-4). The reaction can be carried out within the range of room temperature to 100° C. for several minutes to several hours.

Examples of the acid are concentrated hydrochloric acid, concentrated sulphuric acid, concentrated nitric acid and the like. Preferred is concentrated hydrochloric acid.

Examples of the reaction solvent are acetic acid, methylene chloride, diethyl ether, dichloromethane, toluene, benzene, xylene, cyclohexane, hexane, chloroform, pentane, heptane, dioxane, methanol, ethanol, acetonitrile, mixtures thereof and the like. Preferred is ethanol.

Step V

Compound of the formula (VII-1) having the desired substituent $R^1$ and $R^2$ and Compound of the formula (VIII-4) are reacted to give Compound of the formula (VIII-5). The reaction condition is the same as the above Step M.

Step W

Compound of the formula (I-6) can be obtained from Compound of the formula (VIII-5) by a similar method as the above Step R.

When Ring A is pyrazole, compounds of this invention can be synthesized as below.

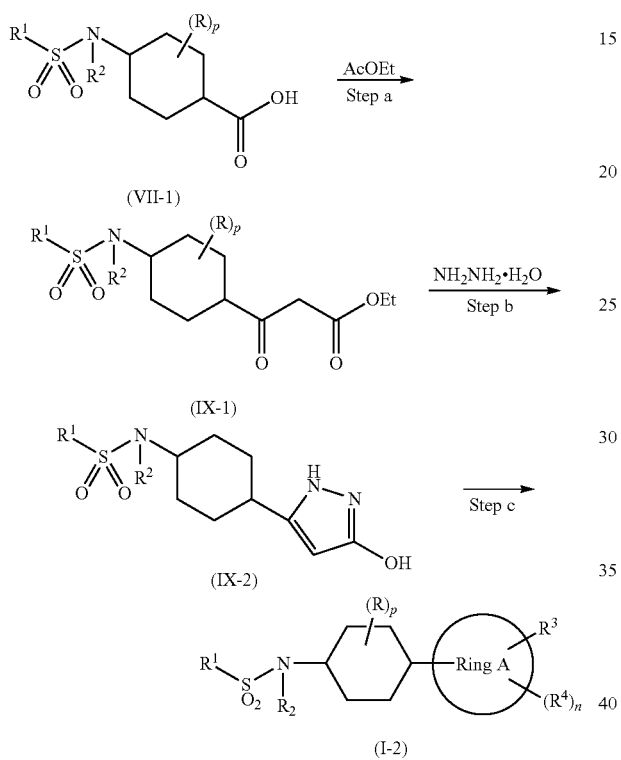

In the above scheme, Ring A is pyrazole and each of the other symbols has the same meaning as that of a compound of the formula (I).

Step a

Compound of the formula (VII-1) having the desired substituent $R^1$ and $R^2$ is treated with a dehydrating agent containing chlorine atoms in an appropriate solvent and reacted within the range of 0° C. to 50° C. for several minutes to several hours to give acid halide. The reaction solvent and dehydrating agent are the same as the above Step M.

The obtained acid halide and ethyl acetate are reacted in an appropriate solvent under the presence of Lewis acid and N-alkyl imidazole within the range of −100° C. to 0° C. for several minutes to several hours and the base is added to the solution to give Compound of the formula (IX-1).

Examples of the Lewis acid are titanium tetrachloride, tin tetrachloride, aluminium trichloride, trifluoroborane-ether complex, boron trichloride, trimethylsilyltrifluoromethansulfonate (TMSOTf), zinc dichloride and the like. Preferred is titanium tetrachloride.

Examples of the N-alkylimidazole are N-methylimidazole, N-ethylimidazole and the like. Preferred is N-methylimidazole.

Examples of the base are N,N'-diisopropylethylamine, diethylamine, triethylamine, pyridine, N-methylmorpholine, dimethylaniline, barium hydroxide, sodium hydroxide, potassium hydroxide and the like. Preferred is N,N'-diisopropylethylamine.

Examples of the reaction solvent are methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred are methylene chloride and/or ethyl acetate.

Step b

Compound of the formula (IX-1) is reacted with hydrazine (e.g., hydrazine monohydrate) in an appropriate solvent to give Compound of the formula (IX-2). The reaction can be carried out within the range of 0° C. to 100° C. for several minutes to several hours.

Examples of the reaction solvent are methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is methanol.

Instead of hydrazine, $NH_2NHR^5$ wherein $R^5$ is $R^3$, $R^4$, or a group from which $R^3$ or $R^4$ is derived can be used. In this case, $R^5$ and a hydroxyl group can be introduced onto the hydrazine ring at a time.

Step c

Compound of the formula (I-2) can be obtained from Compound of the formula (IX-2) by introducing the desired substituent $R^3$ and $R^4$ according to a known method.

When Ring A is triazole, compounds of this invention can be synthesized as below.

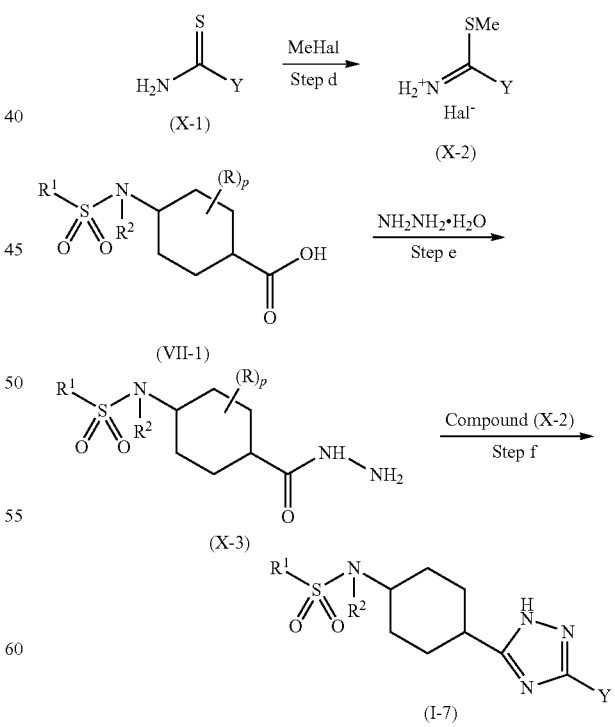

In the above scheme, Y is $R^3$ or $R^4$ of a compound of the formula (I) or hydrogen. Each of the other symbols has the same meaning as that of a compound of the formula (I).

Step d

Compound of the formula (X-1) having the desired substituent $R^3$ and $R^4$ is reacted with halogenomethyl in an appropriate solvent to give Compound of the formula (X-2). The reaction can be carried out within the range of 0° C. to 100° C. for several minutes to several hours.

Examples of the reaction solvent are methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is acetonitrile.

Step e

Compound of the formula (VII-1) having the desired substituent $R^1$ and $R^2$ is reacted with a dehydrating agent in an appropriate solvent and reacted within the range of 0° C. to 50° C. for several minutes to several hours. Hydrazine monohydrate is added to the solution and reacted in an appropriate solvent within the range of 0° C. to 50° C. for several minutes to several hours to give Compound of the formula (X-3).

Examples of the dehydrating agent are carbonyldiimidazole, dicyclohexylcarbodiimide, trifluorobenzene boronic acid, tin bis(bistrimethylsilylamino) and the like. Preferred is carbonyldiimidazole. The amount of the dehydrating agent is preferably 1 to 5 equivalent(s) to Compound of the formula (VII-1).

Examples of the reaction solvent are methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is tetrahydrofuran.

Step f

Compound of the formula (X-3) and Compound of the formula (X-2) are treated with the base in an appropriate solvent to give Compound of the formula (VI-7). The reaction can be carried out within the range of 50° C. to 150° C. for several minutes to several hours.

Examples of the base are diethylamine, triethylamine, pyridine, N-methylmorpholine, dimethylaniline, barium hydroxide, sodium hydroxide, potassium hydroxide, hydrazine, the lithium salt of propanethiol and the like. Preferred is triethylamine.

Examples of the reaction solvent are methylene chloride, tetrahydrofuran, dimethylformamide, diethyl ether, dichloromethane, toluene, benzene, xylene, cyclohexane, hexane, chloroform, ethyl acetate, butyl acetate, pentane, heptane, dioxane, aceton, methanol, ethanol, acetonitrile, water, mixtures thereof and the like. Preferred is ethanol.

In the above Steps, the following intermediates are useful. Especially preferable compounds are the followings.

A compound of the formula:

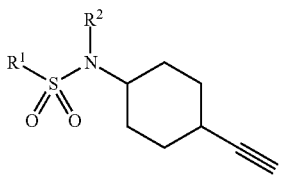

wherein
$R^1$ is substituted or unsubstituted alkyl, substituted or unsubstituted alkenyl or substituted or unsubstituted alkynyl, and
$R^2$ is hydrogen or substituted or unsubstituted alkyl.

Preferable $R^1$ is substituted or unsubstituted alkyl (Especially preferred as $R^1$ is ethyl, isopropyl or tert-butyl), and $R^2$ is hydrogen. A group attached to a cyclohexane ring is a group of the formula: —NHSO$_2$R$^1$ and a group of the formula: —C≡CH.

A compound of the formula:

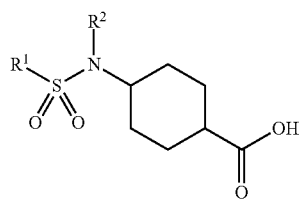

wherein
$R^1$ is substituted or unsubstituted alkyl, substituted or unsubstituted alkenyl or substituted or unsubstituted alkynyl, and
$R^2$ is hydrogen or substituted or unsubstituted alkyl. Especially, $R^1$ is ethyl, isopropyl or tert-butyl, and $R^2$ is hydrogen.

A compound of the formula:

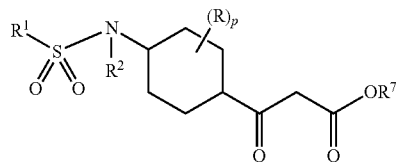

wherein
$R^1$ is substituted or unsubstituted alkyl, substituted or unsubstituted alkenyl or substituted or unsubstituted alkynyl,
$R^2$ is hydrogen or substituted or unsubstituted alkyl, and
$R^7$ is substituted or unsubstituted alkyl.

Preferable $R^1$ is substituted or unsubstituted alkyl (Especially preferable $R^1$ is ethyl, isopropyl or tert-butyl), $R^2$ is hydrogen and $R^7$ is methyl, ethyl, isopropyl or tert-butyl.

A compound of the formula:

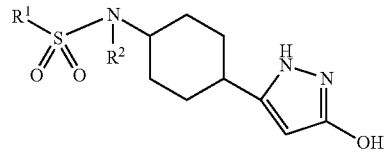

wherein
$R^1$ is substituted or unsubstituted alkyl, substituted or unsubstituted alkenyl or substituted or unsubstituted alkynyl, and
$R^2$ is hydrogen or substituted or unsubstituted alkyl.

Preferable $R^1$ is substituted or unsubstituted alkyl (Especially preferable $R^1$ is ethyl, isopropyl or tert-butyl.) and $R^2$ is hydrogen.

A compound of this invention is effective for all of the diseases associated with NPY Y5, e.g., feeding disorder, obesity, hyperorexia, sexual disorder, impaired fertility, depression, epileptic seizure, hypertension, cerebral hemorrhage, congestive heart failure or sleep disorders and it is especially useful for preventing and/or treating obesity and suppressing food intake. Moreover, it is effective for preventing and/or treating the diseases in which obesity acts as a risk factor, for example, diabetes, hypertension, hyperlipemia, atherosclerosis and acute coronary syndrome.

Furthermore, a compound of this invention has not only NPY Y5 receptor antagonistic activity but also usefulness as a medicine and any or all good characters selected from the followings.
a) weak CYP (e.g., CYP1A2, CYP2C9, CYP3A4 and the like) enzyme inhibition
b) less induction of a drug-metabolizing enzyme.
c) good drug disposition such as high bioavailability, appropriate clearance and the like.
d) low toxicity of anemia-inducing activity or the like.
e) high metabolic stability.
f) high selectivity for Y5 receptor.
g) high water solubility.
h) high transportability through the blood-brain barrier.

In addition, a compound of this invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the NPY Y5 receptor antagonist has a low risk of inducing side effects based on the peripheral vasoconstriction, and a pharmaceutical composition comprising the compound of this invention as an active ingredient is expected to be suitably used as a safe medicine.

The pharmaceutical composition comprising the compound of this invention shows an anti-obesity effect by suppressing food intake. Therefore, it is one of the features of the pharmaceutical composition not to induce side effects such as dyspepsia caused by an anti-obesity agent which inhibits digestion and absorption, or central nervous system side-effects such as an antidepressant effect due to a serotonin transporter inhibitor that shows an anti-obesity effect.

A pharmaceutical composition of this invention can be administered orally or parenterally as an anti-obesity agent or anorectic agent. In the case of oral administration, it may be in any usual form such as tablets, granules, powders, capsules, pills, solutions, syrups, buccal tablets, sublingual tablets and the like. When the compound is parenterally administered, any usual form is preferable, for example, injections (e.g., intravenous, intramuscular), suppositories, endermic agents, inhalations and the like. Oral administration is especially preferable because the compounds of this invention show a high oral absorbability.

A pharmaceutical composition may be manufactured by mixing an effective amount of a compound of this invention with various pharmaceutical additives suitable for the administration form, such as excipients, binders, moistening agents, disintegrants, lubricants, diluents and the like. When the composition is of an injection, an active ingredient together with a suitable carrier can be sterilized to give a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate, macrogol and the like. Cacao oil, macrogol, methylcellulose or the like may be used as base materials of suppositories. When the composition is manufactured as solutions, emulsified injections or suspended injections, solubilizing agent, suspending agents, emulsifiers, stabilizers, preservatives, isotonic agents and the like which are usually used may be added. For oral administration, sweetening agents, flavors and the like which are usually used may be added.

Although the dosage of a pharmaceutical composition of this invention as an anti-obesity agent or anorectic agent should be determined in consideration of the patient's age and body weight, the type and degree of diseases, the administration route and the like, a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

A pharmaceutical composition of this invention can be used in combination of the other known anti-obesity agent(s). Furthermore, a method of treatment by administering a pharmaceutical composition of this invention can be used in combination of the known dietary therapy, drug therapy, exercise and the like.

This invention is further explained by the following Examples, which are not intended to limit the scope of this invention.

The abbreviations used in the present description stand for the following meanings.
Me: methyl
Et: ethyl
Bu: butyl
Hex: hexyl
Ts: paratoluenesulfonyl
THF: tetrahydrofuran
DMF: N,N-dimethylformamide
DABCO: 1,4-diazabicyclo[2,2,2]octane
NBS: N-bromosuccinimide
TBAF: tetrabutylammonium fluoride
LDA: lithium diisopropylamine
DPPA: diphenyl phosphate azide
DBU: 1,8-diazabicyclo[5,4,0]-7-undecene
DCM: methylene chloride
WSCD: Water-Soluble Carbodiimide, 1-ethyl-3-(3-dimethylaminopropyl)carbodiimide
HOBt: 1-hydroxybenzotriazole
Boc: butoxycarbonyl
Tf: triflate
NIS: N-iodosuccinimide
DMA: dimethylacetoamide
CDI: carbonyldiimidazole

EXAMPLE

Example 1

Synthesis of Compound (Ia-7)

Step 1

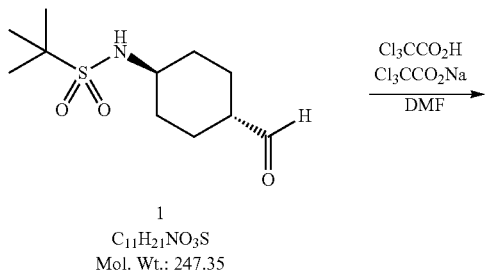

1
C₁₁H₂₁NO₃S
Mol. Wt.: 247.35

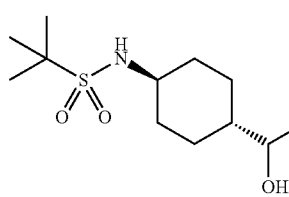

2
C₁₂H₂₂Cl₃NO₃S
Mol. Wt.: 366.73

To Aldehyde 1 (The synthesis method disclosed in WO2007/125952) (21.35 g, 86 mmol) in N,N'-dimethylformamide (120 ml) were added trichloroacetic acid (21.2 g, 129 mmol) and trichloroacetic acid sodium salt (24.0 g, 129 mmol) at 18° C. and the mixture was stirred within the range of 23° C. to 26° C. for 1 hour. To a reactant was added 10% sodium hydrogen carbonate solution (240 mL). After filtering the deposited solid, the obtained solid was washed with water and hexane to give Compound 2 (29.4 g, yield 93%) as pale yellow solid.

¹H-NMR (DMSO-d₆) δppm: 1.20-1.44 (m, 4H), 1.26 (s, 9H), 1.66-1.77 (m, 2H), 1.77-2.02 (m, 4H), 2.97 (m, 1H), 3.81 (s, 1H), 6.59 (s, 1H), 6.76 (d, 1H, J=8.6 Hz).

Step 2

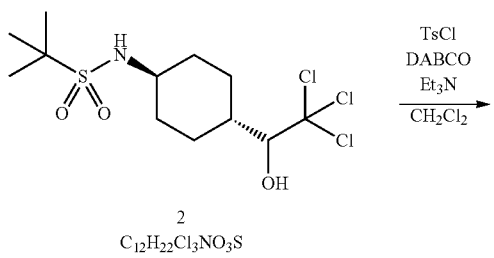

2
C₁₂H₂₂Cl₃NO₃S
Mol. Wt.: 366.73

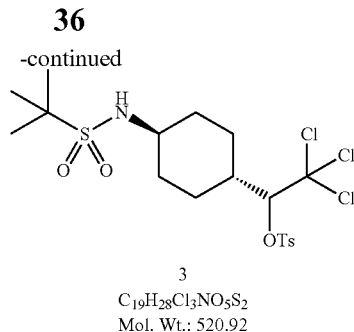

3
C₁₉H₂₈Cl₃NO₅S₂
Mol. Wt.: 520.92

To Compound 2 (30.0 g, 82 mmol) in methylene chloride (200 ml) were added successively triethylamine (34.0 g, 245 mmol), 1,4-diazabicyclo[2,2,2]octane (DABCOT™, 2.75 g, 24.5 mmol) and p-toluenesulfonyl chloride (31.2 g, 164 mmol) at room temperature and the mixture was stirred at room temperature for 7 hours. The reactant was poured into 2 N hydrochloric acid, extracted with chloroform and then washed with water. After drying over magnesium sulfate, the solvent was removed under reduced pressure. The residue was recrystallized with the mixed solvent of chloroform and hexane to give Compound 3 (38.24 g, yield 90%) as colorless solid.

¹H-NMR (DMSO-d₆) δppm: 0.95-1.11 (m, 2H), 1.17-1.33 (m, 2H), 1.25 (s, 9H), 1.75-1.93 (m, 4H), 2.00 (m, 1H), 2.43 (s, 3H), 2.73 (m, 1H), 4.89 (s, 1H), 6.81 (d, 1H, J=8.6 Hz), 7.50 (d, 1H, J=8.1 Hz), 7.90 (d, 1H, J=8.1 Hz).

Step 3

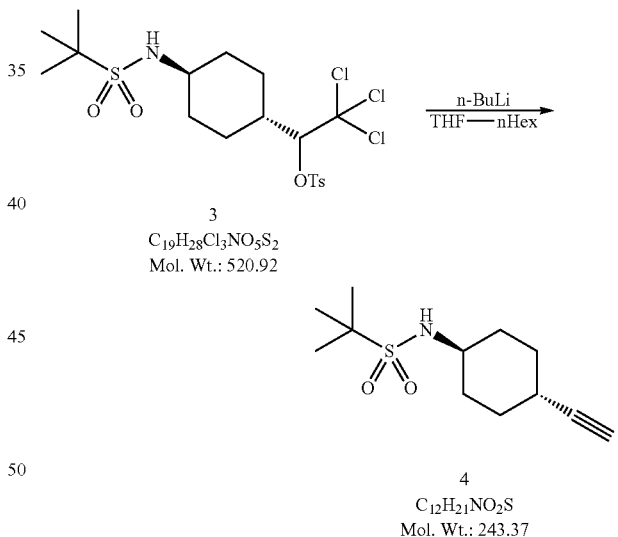

3
C₁₉H₂₈Cl₃NO₅S₂
Mol. Wt.: 520.92

4
C₁₂H₂₁NO₂S
Mol. Wt.: 243.37

To Compound 3 (91.0 g, 175 mmol) in tetrahydrofuran (750 ml) was added n-butyllithium in n-hexane (1.6 M solution, 600 mL, 960 mmol) at −30° C. and the mixture was stirred within the range of −22° C. to −15° C. for 30 minutes. To the reactant was added carefully 5% ammonium chloride solution. After extracting with ethyl acetate, the organic layer was washed with saturated saline and then dried over magnesium sulfate. The solvent was removed under reduced pressure and the residue was washed with hexane to give Compound 4 (34.5 g, yield 81%) as colorless solid.

¹H-NMR (DMSO-d₆) δppm: 1.15-1.42 (m, 4H), 1.25 (s, 9H), 1.80-1.95 (m, 4H), 2.16 (m, 1H), 2.83 (s, 1H), 3.04 (m, 1H), 6.78 (d, 1H, J=8.8 Hz).

Step 4

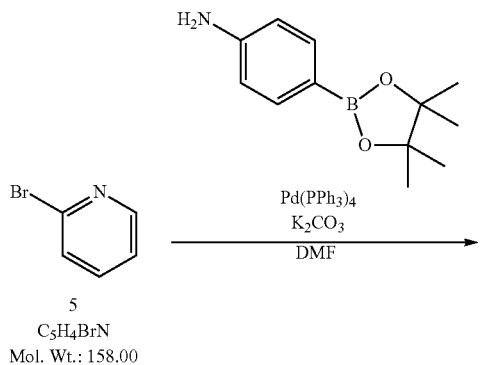

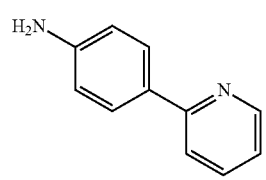

2-bromopyridine 5 (14.53 g, 92.0 mmol) and 4-aminophenylboronic acid pinacol ester (30.20 g, 138.0 mmol) were dissolved in dimethylformamide (200 ml). To the solution were added tetrakis triphenyl phosphine palladium (7.44 g, 6.4 mmol) and 2 M potassium carbonate solution (230 ml, 460 mmol) and the mixture was stirred for 2 hours at 100° C. The reactant was poured into water and filtered and the filtrate was extracted with ethyl acetate. The organic layer was washed with water and then saturated saline, and dried over anhydrous magnesium sulfate. The solvent was removed under reduced pressure and the residue was purified by silica gel chromatography. To the obtained solid were added ethyl acetate and hexane and the deposited solid was collected with filtration to give the desired substituted aniline 6 (12.35 g, yield 79%).

$^1$H-NMR (DMSO-d6) δppm: 5.42 (s, 2H), 6.63 (m, 2H), 7.14 (m, 1H), 7.69-7.75 (m, 2H), 7.79 (m, 2H), 8.51 (m, 1H).

Step 5

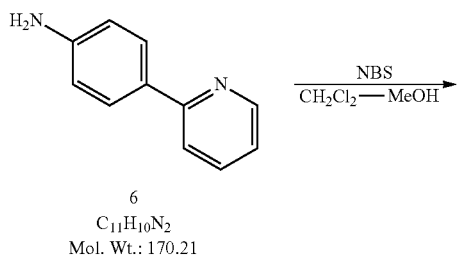

-continued

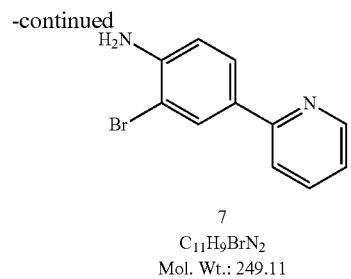

Compound 6 obtained in Step 4 (16.13 g, 95.0 mmol) was dissolved in dichloromethane (120 ml) and methanol (120 ml). To the solution was added N-bromosuccinimide (17.71 g, 100.0 mmol) under ice cooling and the mixture was stirred for 2 hours under ice cooling. The reactant was poured into saturated saline and extracted with ethyl acetate. The organic layer was washed with water and dried over anhydrous magnesium sulfate. The solvent was removed under reduced pressure and the residue was purified by silica gel chromatography to give the desired Compound 7 (19.36 g, yield 82%).

$^1$H-NMR (DMSO-d6) δppm: 5.64 (s, 2H), 6.86 (d, 1H, J=8.4 Hz), 7.20 (ddd, 1H, J=6.6, 5.1, 1.5 Hz), 7.72-7.84 (m, 3H), 8.12 (d, 1H, J=2.1 Hz), 8.54 (m, 1H).

Step 6

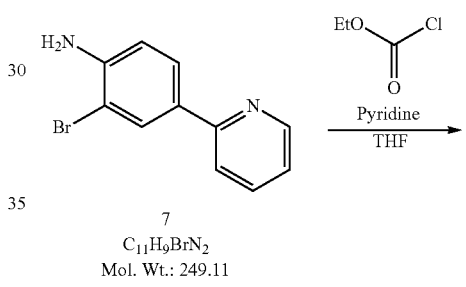

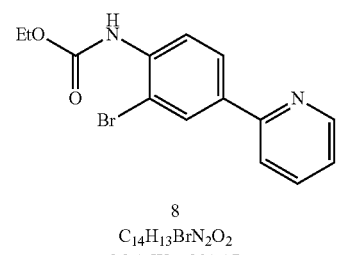

Compound 7 obtained in Step 5 (19.36 g, 78.0 mmol) was dissolved in tetrahydrofuran (150 ml). To the mixture were added pyridine (12.54 ml, 155.0 mmol) and ethyl chlorocarbonate (11.14 ml, 117.0 mmol) under ice cooling and the mixture was stirred for 1 hour at room temperature. The reactant was poured into saturated sodium hydrogen carbonate solution and extracted with ethyl acetate. The organic layer was washed with water and dried over anhydrous magnesium sulfate. The solvent was removed under reduced pressure. To the residue were added ethyl acetate and hexane. The deposited solid was collected with filtration to give the desired Compound 8 (20.21 g, yield 81%).

$^1$H-NMR (DMSO-d6) δppm: 1.26 (t, 3H, J=7.2 Hz), 4.15 (q, 2H, J=7.2 Hz), 7.36 (ddd, 1H, J=7.5, 4.8, 1.2 Hz), 7.68 (d, 1H, J=8.7 Hz), 7.88 (ddd, 1H, J=8.1, 7.5, 1.8 Hz), 8.00 (ddd, 1H, J=8.1, 1.2, 0.9 Hz), 8.07 (dd, 1H, J=8.7, 1.8 Hz), 8.35 (d, 1H, J=1.8 Hz), 8.65 (ddd, 1H, J=4.8, 1.8, 0.9 Hz), 8.97 (s, 1H).

Step 7

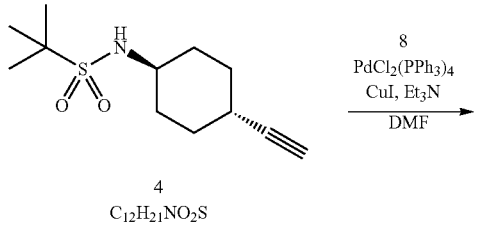

4
C₁₂H₂₁NO₂S
Mol. Wt.: 243.37

8
PdCl₂(PPh₃)₄
CuI, Et₃N
———————→
DMF

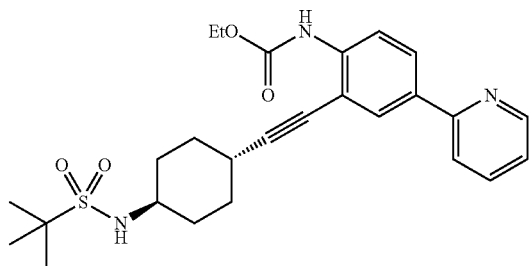

9
C₂₆H₃₃N₃O₄S
Mol. Et.: 483.62

Alkyne 4 (490 mg, 2.01 mmol) and Compound 8 (468 mg, 1.45 mmol) were dissolved in dimethylformamide (4.5 ml). To the solution were added dichlorobis triphenyl phosphine-palladium (44 mg, 0.063 mmol), copper iodide (21 mg, 0.11 mmol) and triethylamine (1.5 ml, 10.8 mmol) and the mixture was stirred for 8 hours at 80° C. The reactant was poured into saturated ammonium chloride solution and extracted with ethyl acetate. The organic layer was washed with water and dried over anhydrous magnesium sulfate. The solvent was removed under reduced pressure and the residue was purified by silica gel chromatography. To the obtained solid were added ethyl acetate and methanol and dissolved under heating. After radiational cooling, the deposited solid was collected with filtration to give the desired Compound 9 (536 mg, yield 71%).

¹H-NMR (DMSO-d6) δppm: 1.24-1.56 (m, 16H), 1.89-2.09 (m, 4H), 2.53 (m, 1H), 3.13 (m, 1H), 4.16 (q, 2H, J=7.2 Hz), 6.84 (d, 1H, J=8.4 Hz), 7.33 (ddd, 1H, J=7.5, 4.8, 0.9 Hz), 7.79-7.89 (m, 2H) 7.96 (m, 1H), 8.04 (dd, 1H, J=8.7, 2.1 Hz), 8.07 (d, 1H, J=2.1 Hz), 8.47 (s, 1H), 8.63 (m, 1H).

Step 8

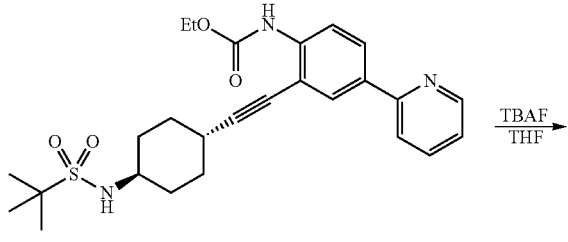

9
C₂₆H₃₃N₃O₄S
Mol. Wt.: 483.62

TBAF
———→
THF

-continued

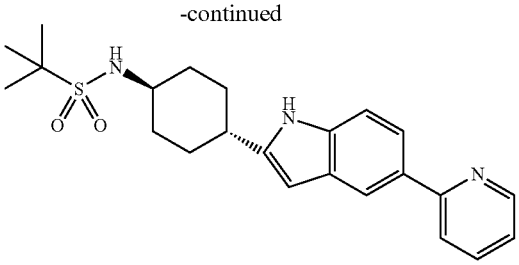

10 (Ia-7)
C₂₃H₂₉N₃O₂S
Mol. Wt.: 411.56

Compound 9 obtained in Step 7 (535 mg, 1.1 mmol) was dissolved in tetrahydrofuran (5 ml). To the solution was added tetrabutylammonium fluoride (1 M THF solution, 3.3 ml, 3.3 mmol) and the mixture was stirred for 4 hours at 80° C. The reactant was poured into water and extracted with ethyl acetate. The organic layer was washed with water and dried over anhydrous magnesium sulfate. The solvent was removed under reduced pressure and the residue was purified by silica gel chromatography. To the obtained solid was added ethyl acetate and dissolved under heating. After radiational cooling, the deposited solid was collected with filtration to give the desired Compound 10 (240 mg, yield 53%).

¹H-NMR (DMSO-d₆) δ: 1.29 (s, 9H), 1.35-1.63 (m, 4H), 1.97-2.14 (m, 4H), 2.64 (t, 1H, J=11.4 Hz), 3.06-3.23 (m, 1H), 6.20 (s, 1H), 6.85 (d, 1H, J=8.7 Hz), 7.18-7.25 (m, 1H), 7.33 (d, 1H, J=8.4 Hz), 7.77-7.81 (m, 2H), 7.89 (d, 1H, J=8.1 Hz), 8.15 (s, 1H), 8.57-8.62 (m, 1H), 10.99 (s, 1H).

Example 2

Synthesis of Compound (Ib-14)

Step 1

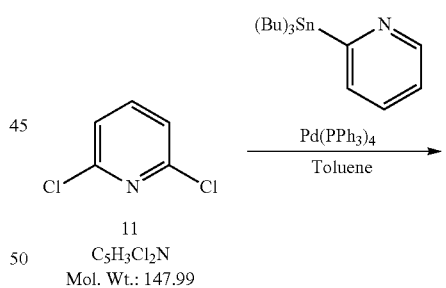

11
C₅H₃Cl₂N
Mol. Wt.: 147.99

Pd(PPh₃)₄
————→
Toluene

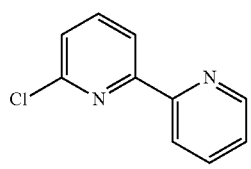

12
C₁₀H₇ClN₂
Mol. Wt.: 190.63

2,6-dichloropyridine 11 (8.88 g, 60.0 mmol) and 2-(tributylstannyl)pyridine (7.36 g, 20.0 mmol) were dissolved in toluene (74 ml). To the solution was added tetrakis triphenyl phosphinepalladium (2.31 g, 2.0 mmol) and the mixture was stirred under heat refluxing for 11 hours. The reactant was condensed under reduced pressure and the residue was purified by silica gel chromatography to give quantitatively the desired Compound 12 (3.9 g).

$^1$H-NMR (DMSO-d6) δppm: 7.50-7.53 (m, 1H), 7.59 (d, 1H, J=8.0 Hz), 7.93-8.05 (m, 2H), 8.30 (d, 1H, J=8.0 Hz), 8.38 (d, 1H, J=8.0 Hz), 8.72 (d, 1H, J=4.4 Hz).

Step 2

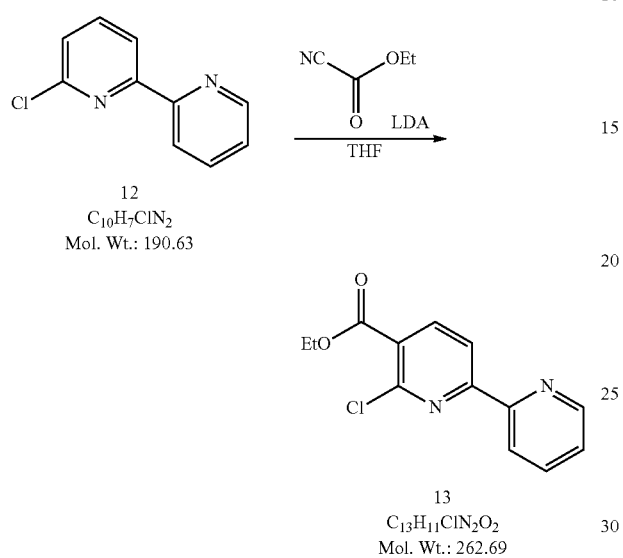

Compound 12 was obtained in Step 1 (3.8 g, 19.9 mmol) was dissolved in tetrahydrofuran (120 ml). To the solution was added dropwise lithium diisopropylamine (2.0 M in tetrahydrofuran, 29.9 mL, 59.8 mmol) at −78° C. and the mixture was stirred for 1 hour. Cyano ethyl formate (7.90 g, 80.0 mmol) in tetrahydrofuran (320 ml) was added dropwise to the reactant and the mixture was stirred for 2 hours. The reactant was poured into water. After separating, the water layer was extracted with chloroform. The organic layer was added thereto and dried over anhydrous magnesium sulfate. The solvent was removed under reduced pressure and the residue was purified by silica gel chromatography to give the desired Compound 13 (544.4 mg, yield 10.4%).

1H-NMR (DMSO-d6) δppm: 1.36 (t, 3H, J=6.8 Hz), 4.38 (q, 2H, J=6.8 Hz), 7.55-7.58 (m, 1H), 8.00-8.04 (m, 1H), 8.34 (d, 1H, J=8.4 Hz), 8.41 (d, 1H, J=8.4 Hz), 8.47 (d, 1H, J=8.4 Hz), 8.75 (d, 1H, J=4.4 Hz).

Step 3

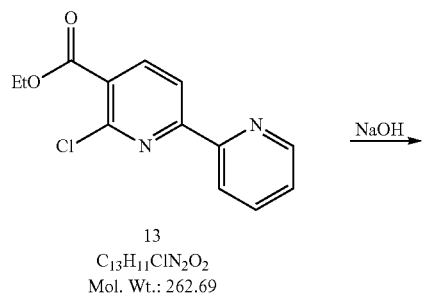

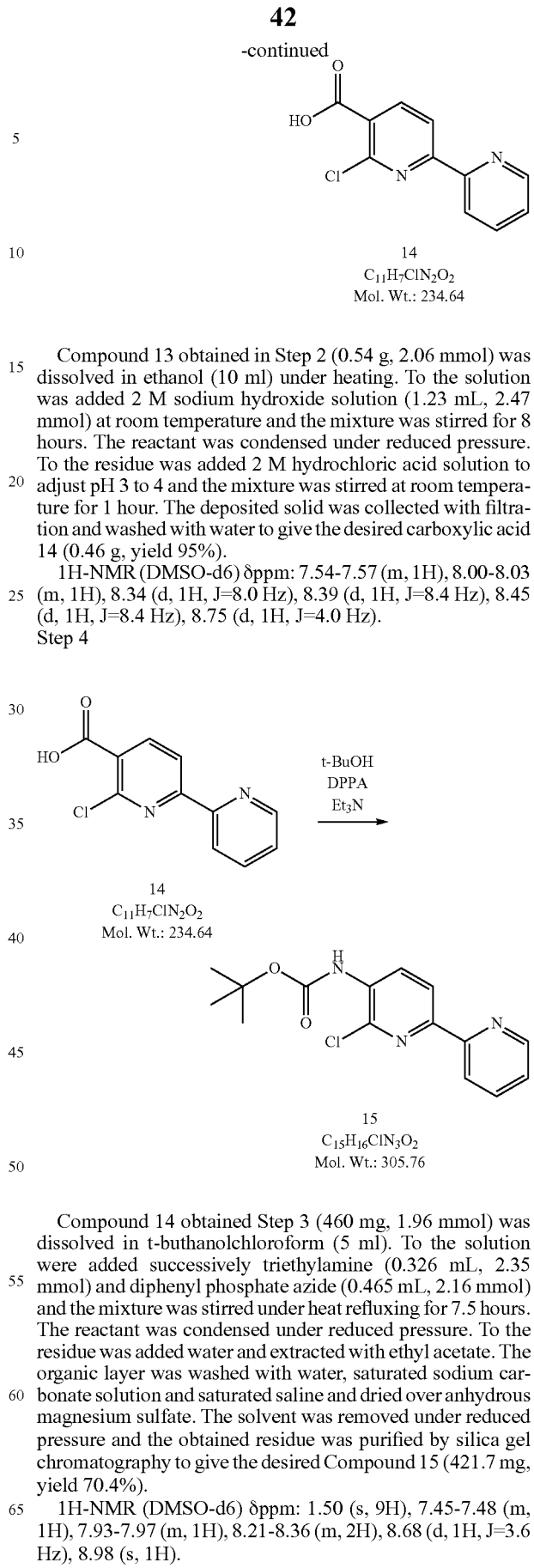

Compound 13 obtained in Step 2 (0.54 g, 2.06 mmol) was dissolved in ethanol (10 ml) under heating. To the solution was added 2 M sodium hydroxide solution (1.23 mL, 2.47 mmol) at room temperature and the mixture was stirred for 8 hours. The reactant was condensed under reduced pressure. To the residue was added 2 M hydrochloric acid solution to adjust pH 3 to 4 and the mixture was stirred at room temperature for 1 hour. The deposited solid was collected with filtration and washed with water to give the desired carboxylic acid 14 (0.46 g, yield 95%).

1H-NMR (DMSO-d6) δppm: 7.54-7.57 (m, 1H), 8.00-8.03 (m, 1H), 8.34 (d, 1H, J=8.0 Hz), 8.39 (d, 1H, J=8.4 Hz), 8.45 (d, 1H, J=8.4 Hz), 8.75 (d, 1H, J=4.0 Hz).

Step 4

Compound 14 obtained Step 3 (460 mg, 1.96 mmol) was dissolved in t-buthanolchloroform (5 ml). To the solution were added successively triethylamine (0.326 mL, 2.35 mmol) and diphenyl phosphate azide (0.465 mL, 2.16 mmol) and the mixture was stirred under heat refluxing for 7.5 hours. The reactant was condensed under reduced pressure. To the residue was added water and extracted with ethyl acetate. The organic layer was washed with water, saturated sodium carbonate solution and saturated saline and dried over anhydrous magnesium sulfate. The solvent was removed under reduced pressure and the obtained residue was purified by silica gel chromatography to give the desired Compound 15 (421.7 mg, yield 70.4%).

1H-NMR (DMSO-d6) δppm: 1.50 (s, 9H), 7.45-7.48 (m, 1H), 7.93-7.97 (m, 1H), 8.21-8.36 (m, 2H), 8.68 (d, 1H, J=3.6 Hz), 8.98 (s, 1H).

Step 5

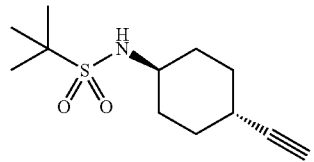

4
C₁₂H₂₁NO₂S
Mol. Wt.: 243.37

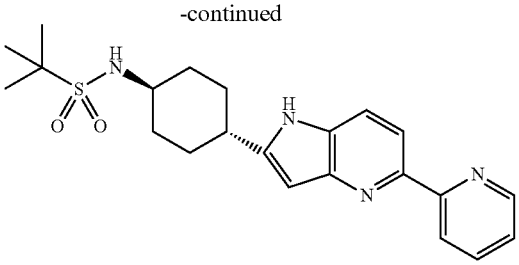

17 (Ib-14)
C₂₂H₂₈N₄O₂S
Mol. Wt.: 412.55

Crude product 16 obtained in Step 1 was dissolved in methanol/water (3/1) (4 mL). To the solution was added 1,8-diazabicyclo[5,4,0]-7-undecene (0.402 mL, 2.67 mmol) and the mixture was stirred for 3 hours at 85° C. The reactant was neutralized and extracted with ethyl acetate. The organic layer was washed with water and dried over anhydrous magnesium sulfate. The solvent was removed under reduced pressure and the residue was purified by silica gel chromatography. The obtained solid was recrystallized from n-hexane and ethyl acetate and the deposited solid was collected with filtration to give the desired Compound 17 (38 mg, yield 17%).

$_1$H-NMR (DMSO-d₆) δ: 1.29 (s, 9H), 1.44-1.60 (m, 4H), 2.06-2.10 (m, 4H), 2.67-2.69 (m, 1H), 3.18-3.20 (m, 1H), 6.36 (s, 1H), 6.85 (d, 1H, J=8.8 Hz), 7.31-7.38 (m, 1H), 7.74 (d, 1H, J=8.8 Hz), 7.85-7.89 (m, 1H), 8.15 (d, 1H, J=8.0 Hz), 8.41 (d, 1H, J=8.0 Hz), 8.60-8.63 (m, 1H), 11.25 (s, 1H).

Example 3

Synthesis of Compound (IIa-1)

Step 1

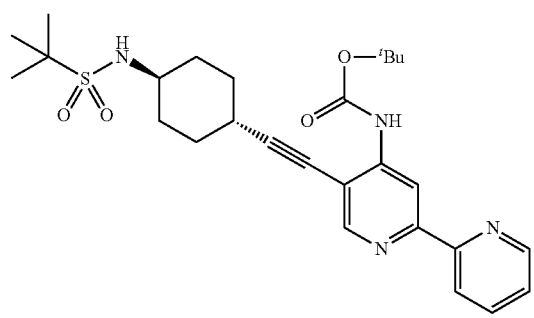

16
C₂₃H₂₇N₄O₃S
Mol. Wt.: 439.55

Alkyne 4 (143 mg, 0.586 mmol) and Compound 15 (163 mg, 0.533 mmol) were dissolved in dimethylformamide (1 ml). To the solution were added dichlorobis triphenyl phosphinepalladium (18.7 mg, 0.027 mmol), copper iodide (5.1 mg, 0.027 mmol) and triethylamine (5.0 ml, 36.1 mmol) and the mixture was stirred for 8 hours at 80° C. The reactant was filtered by celite and the filtrate was removed under reduced pressure. The obtained residue was purified by silica gel chromatography to give the desired Compound 16 as crude product.

Step 6

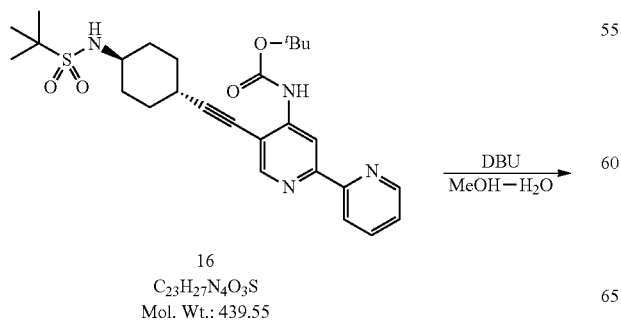

16
C₂₃H₂₇N₄O₃S
Mol. Wt.: 439.55

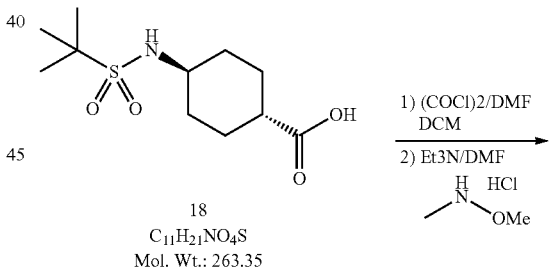

18
C₁₁H₂₁NO₄S
Mol. Wt.: 263.35

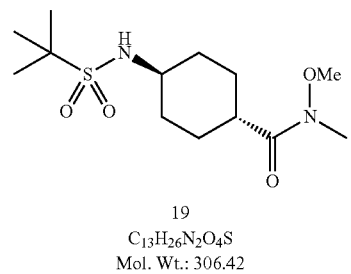

19
C₁₃H₂₆N₂O₄S
Mol. Wt.: 306.42

To Carboxylic acid 18 (The synthesis method disclosed in WO2001/037826) (21.07 g, 80 mmol) was added methylene chloride (120 ml). To the mixture were added N,N'-dimethylformamide (311 μL, 4.0 mmol) and oxalyl chloride (7.70 mL, 88.0 mmol) at 4° C. The mixture was stirred at room temperature for 1 hour. To the mixture were added successively N,O-dimethyl hydroxylamine hydrochloride (7.80 g), tetrahydrofuran (45 ml) and triethylamine (44.4 mL, 320 mmol) and the mixture was stirred at room temperature for 1 hour. The reactant was poured into 2 N hydrochloric acid and extracted with ethyl acetate. The organic layer was washed with saturated sodium hydrogen carbonate solution and saturated saline and dried over magnesium sulfate. The solvent was removed under reduced pressure. To the residue were added ethyl acetate and hexane and the deposited solid was collected with filtration to give Compound 19 (15.8 g, yield 64%) as colorless solid.

$^1$H-NMR (DMSO-d$_6$) δppm: 1.23 (s, 9H), 1.26-1.44 (m, 4H), 1.66-1.78 (m, 2H), 2.54 (m, 1H), 3.03 (m, 1H), 3.08 (s, 3H), 3.67 (s, 3H), 6.80 (d, 1H, J=8.8 Hz).

Step 2

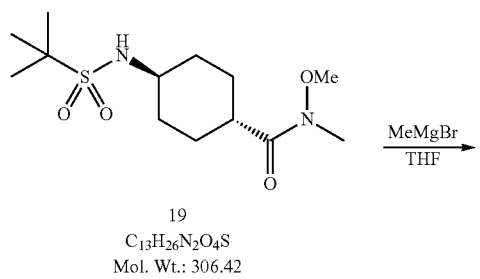

19
C$_{13}$H$_{26}$N$_2$O$_4$S
Mol. Wt.: 306.42

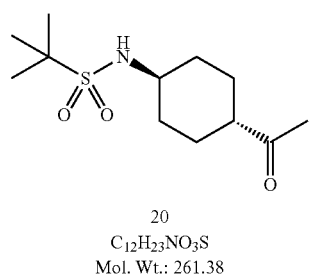

20
C$_{12}$H$_{23}$NO$_3$S
Mol. Wt.: 261.38

To Compound 19 (15.56 g, 50.8 mmol) in tetrahydrofuran (45 ml) was added a solution of methyl magnesium bromide and diethyl ether (3 M solution, 43 mL, 127 mmol) at 5° C. and the mixture was stirred at room temperature for 1.5 hours. To the reactant was added 5% ammonium chloride solution and the mixture was extracted with ethyl acetate. The organic layer was washed with saturated saline and dried over magnesium sulfate. The solvent was removed under reduced pressure. To the residue was added the mixed solvent of ethyl acetate and hexane and the deposited solid was collected with filtration to give Compound 20 (10.1 g, yield 76%) as colorless solid.

$^1$H-NMR (DMSO-d6) δppm: 1.15-1.37 (m, 4H), 1.26 (s, 9H), 1.80-1.96 (m, 4H), 2.09 (s, 3H), 2.24 (m, 1H), 2.99 (m, 1H), 6.78 (d, 1H, J=8.4 Hz).

Step 3

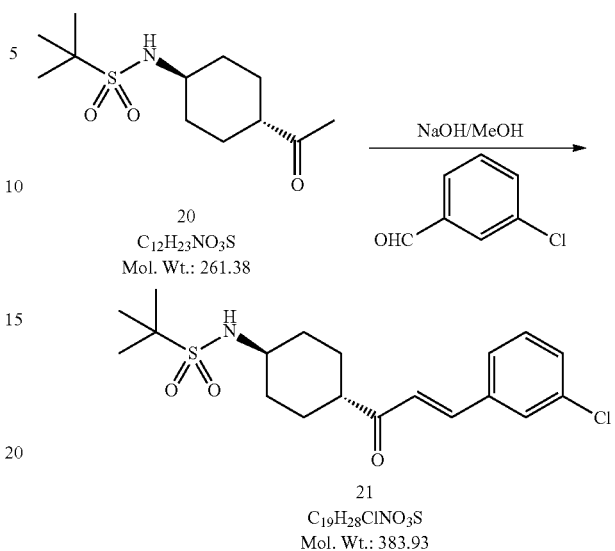

To Compound 20 (262 mg, 1.00 mmol) in methanol (3 ml) were added successively 3-chlorobenzaldehyde (141 mg, 1.00 mmol) and 1 N sodium hydroxide solution (1.50 mL, 1.50 mmol) at 0° C. and the mixture was stirred at room temperature for 3 hours. The reactant was poured into 2 N hydrochloric acid and extracted with ethyl acetate. The organic layer was washed with saturated saline and dried over magnesium sulfate. The solvent was removed under reduced pressure. The residue was recrystallized from the mixed solvent of ethyl acetate and hexane to give Compound 21 (246 mg, yield 64%) as colorless solid.

$^1$H-NMR (DMSO-d$_6$) δppm: 1.27 (s, 9H), 1.29-1.46 (m, 4H), 1.83-2.02 (m, 4H), 2.63 (m, 1H), 3.06 (m, 1H), 6.84 (d, 1H, J=8.8 Hz), 7.16 (d, 1H, J=16.2 Hz), 7.42-7.50 (m, 2H), 7.55 (d, 1H, J=16.2 Hz), 7.69 (d, 1H, J=7.0 Hz), 7.88 (s, 1H).

Step 4

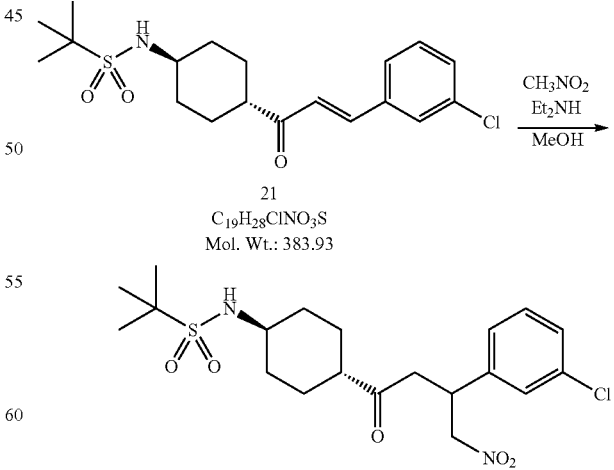

To Compound 21 (240 mg, 0.625 mmol) in methanol (3 ml) were added successively diethylamine (327 μL, 3.13 mmol) and nitro methane (169 μL, 3.13 mmol) at room temperature and the mixture was stirred at 60° C. for 9 hours. The reactant was poured into 2 N Hydrochloric acid and extracted with chloroform. The organic layer was washed with water and dried over magnesium sulfate. The solvent was removed under reduced pressure and the residue was purified by column chromatography (n-hexane ethyl acetate=2:8→4:6) with silica gel (12 g) to give Compound 22 (173 mg, yield 62%) as colorless powder.

$^1$H-NMR (DMSO-$d_6$) δppm: 1.00-1.35 (m, 4H), 1.24 (s, 9H), 1.66-1.83 (m, 2H), 1.83-1.96 (m, 2H), 2.25 (m, 1H), 2.90-3.06 (m, 3H), 3.83 (m, 1H), 4.79 (dd, 1H, J=13.1, 9.2 Hz), 4.85 (dd, 1H, J=13.1, 6.0 Hz), 6.76d, 1H, J=8.6 Hz), 7.24-7.35 (m, 3H), 7.43 (s, 1H).

Step 5

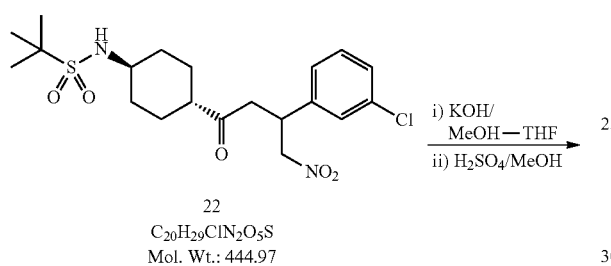

22
C$_{20}$H$_{29}$ClN$_2$O$_5$S
Mol. Wt.: 444.97

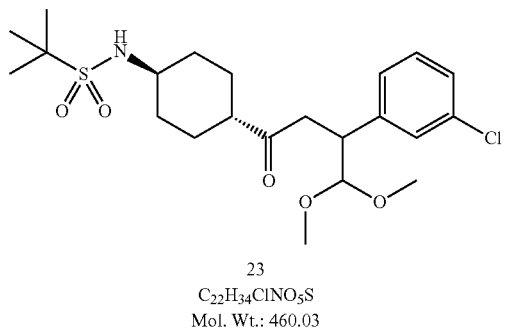

23
C$_{22}$H$_{34}$ClNO$_5$S
Mol. Wt.: 460.03

To Compound 22 (163 mg, 0.366 mmol) in methanol (2 ml) were added successively tetrahydrofuran (4 ml) and potassium hydroxide (103 mg, 1.83 mmol) at room temperature and the mixture was stirred at room temperature for 1 hour. The reactant was added to concentrated sulphuric acid (780 μL) in methanol at 0° C. and the mixture was stirred at room temperature for 2 hours. The reactant was poured into 2 N sodium hydroxide solution and extracted with ethyl acetate. The organic layer was washed with saturated saline and dried over magnesium sulfate. The solvent was removed under reduced pressure to give Compound 23 (161 mg, yield 96%) as colorless oil.

$^1$H-NMR (DMSO-$d_6$) δppm: 0.99-1.12 (m, 2H), 1.15-1.33 (m, 2H), 1.24 (s, 9H), 1.64-1.79 (m, 2H), 1.79-2.02 (m, 4H), 2.21 (m, 1H), 2.89 (m, 1H), 2.97 (m, 1H), 3.16 (s, 3H), 3.25 (s, 3H), 4.43 (d, 1H, J=6.3 Hz), 6.76 (d, 1H, J=9.2 Hz), 7.19-7.25 (m, 2H), 7.27 (d, 1H, J=7.8 Hz), 7.31 (s, 1H).

Step 6

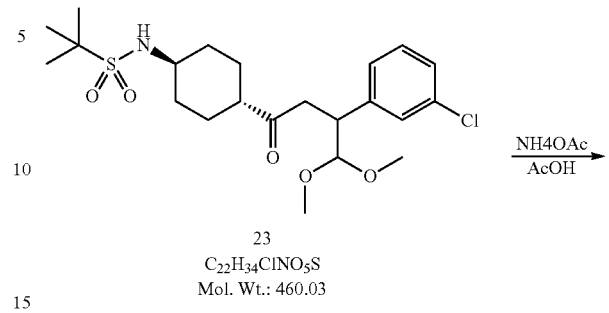

23
C$_{22}$H$_{34}$ClNO$_5$S
Mol. Wt.: 460.03

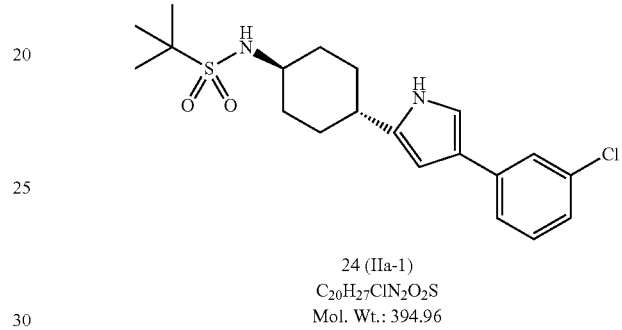

24 (IIa-1)
C$_{20}$H$_{27}$ClN$_2$O$_2$S
Mol. Wt.: 394.96

To Compound 23 (163 mg, 0.348 mmol) in acetic acid (2 ml) was added ammonium acetate (134 mg, 1.74 mmol) at room temperature and the mixture was stirred at 100° C. for 5 hours. The reactant was poured saturated sodium hydrogen carbonate solution and extracted with ethyl acetate. The organic layer was washed with saturated saline and dried over magnesium sulfate. The solvent was removed under reduced pressure. The residue was purified by column chromatography (n-hexane:ethyl acetate=8:2→6:5) with silica gel (12 g) to Compound 24 (21 mg, yield 15%) as yellow powder.

$^1$H-NMR (DMSO-$d_6$) δ: 1.28 (s, 9H), 1.37-1.47 (m, 4H), 1.91-2.01 (m, 4H), 2.42 (m, 1H), 3.09 (m, 1H), 6.16 (s, 1H), 6.80 (d, 1H, J=9.2 Hz), 7.14 (s, 1H), 7.27 (dd, 1H, J=8.4, 7.6 Hz), 7.42 (d, 1H, J=7.6 Hz), 7.50 (s, 1H), 10.7 (s, 1H).

Example 4

Synthesis of Compound (IIIa-2)

Step 1

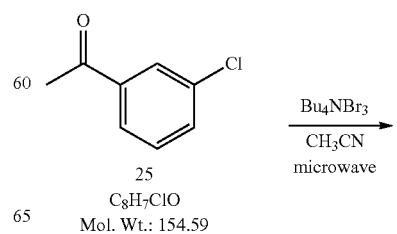

25
C$_8$H$_7$ClO
Mol. Wt.: 154.59

-continued

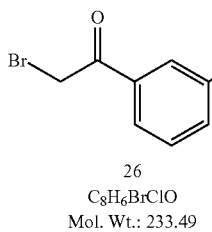

26
C$_8$H$_6$BrClO
Mol. Wt.: 233.49

1-(3-chlorophenyl)ethanone 25 (750 mg, 4.85 mmol) was dissolved in acetonitrile (11.5 ml). To the solution was added tetrabutylammonium bromide (2.34 g, 4.85 mmol) and the mixture was in sealed tubes and stirred by a microwave reactor for 2 minutes at 150° C. The reactant was poured into water and extracted with ethyl acetate. The organic layer was washed with saturated sodium hydrogen carbonate solution, washed with water and dried over anhydrous magnesium sulfate. The solvent was removed under reduced pressure and the residue was purified by silica gel chromatography to give the desired compound 26 (1.02 g, yield 90%).

$^1$H-NMR (DMSO-d$_6$) δ: 5.01 (s, 2H), 7.60-7.65 (m, 1H), 7.77-7.80 (m, 1H), 7.96-8.06 (m, 2H).

Step 2

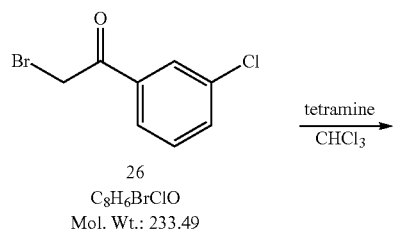

26
C$_8$H$_6$BrClO
Mol. Wt.: 233.49

27
C$_{14}$H$_{18}$BrClN$_4$O
Mol. Wt.: 373.68

Compound 26 obtained in Step 1 (4.78 g, 20.47 mmol) was dissolved in chloroform (25 ml). To the solution was added hexamethylenetetramine (2.87 g, 20.47 mmol) and the mixture was stirred for 1.5 hours at 50° C. After stirring for 30 minutes at 0° C., the deposited solid was collected with filtration and washed with chloroform to give the desired Compound 27 (7.30 g, yield 95%).

$^1$H-NMR (DMSO-d$_6$) δ: 4.61-4.75 (m, 8H), 5.40 (s, 6H), 7.66-7.72 (m, 1H), 7.85-7.89 (m, 1H), 7.95-7.99 (m, 1H), 8.05-8.06 (m, 1H).

Step 3

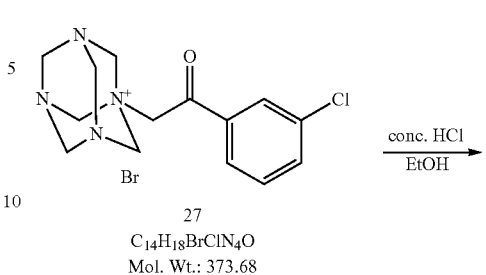

27
C$_{14}$H$_{18}$BrClN$_4$O
Mol. Wt.: 373.68

28
C$_8$H$_9$Cl$_2$NO
Mol. Wt.: 206.07

Compound 27 obtained in Step 2 (7.30 g, 19.54 mmol) was suspended in ethanol (43 ml). To the mixture was added concentrated hydrochloric acid (9.8 ml) and the mixture was stirred for 2.5 hours at 50° C. After stirring for 30 minutes at 0° C., the deposited solid was collected with filtration. To the obtained solid was added water, dissolved under heating and standed to cool to room temperature to deposit solid. The deposited solid was collected with filtration to give the desired Compound 28 (850 mg, yield 21%).

$^1$H-NMR (DMSO-d$_6$) δ: 4.11 (br, 3H), 4.67 (s, 2H), 7.65-7.71 (m, 1H), 7.84-7.87 (m, 1H), 8.01-8.05 (m, 1H), 8.09-8.11 (m, 1H).

Step 4

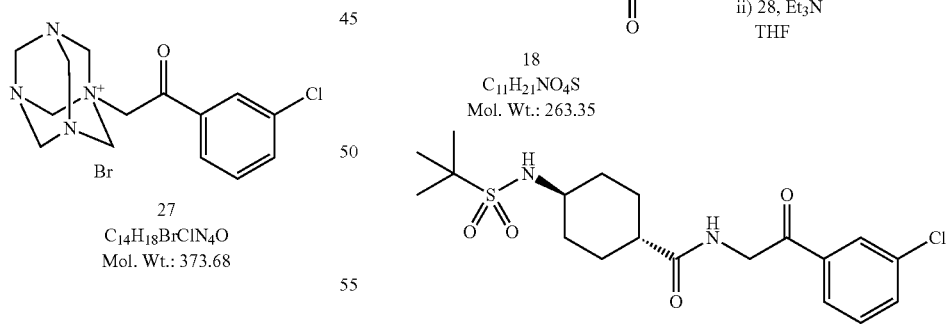

18
C$_{11}$H$_{21}$NO$_4$S
Mol. Wt.: 263.35

29
C$_{19}$H$_{27}$ClN$_2$O$_4$S
Mol. Wt.: 414.95

Carboxylic acid 18 (The synthesis method disclosed in WO2001/037826) (422 mg, 1.608 mmol) was suspended in methylene chloride (4 ml). To the mixture were added oxalyl-chloride (0.17 ml, 1.92 mmol) and 2 drops of N,N-dimethyl-formamide carefully and the mixture was stirred at room temperature for 1 hour.

In the other reaction container, Compound 28 obtained in Step 3 (451 mg, 1.60 mmol) was suspended in tetrahydrofuran (4 ml). To the mixture were added dropwise methylene chloride solution obtained as above and triethylamine (0.81 ml, 5.82 mmol) at 0° C. and the mixture was stirred at room temperature overnight. The reactant was poured into saturated sodium hydrogen carbonate solution and extracted with ethyl acetate. The organic layer was washed with water and saturated sodium chloride solution and dried over magnesium sulfate.

The solvent was removed under reduced pressure and the residue was purified by silica gel chromatography to give the desired Compound 29 (598 mg, yield 99%).

$^1$H-NMR (DMSO-$d_6$) δ: 1.28 (s, 9H), 1.33-1.42 (m, 4H), 1.77-1.97 (m, 4H), 2.11-2.21 (m, 1H), 2.98-3.07 (m, 1H), 4.57 (d, 2H, J=6.0 Hz), 6.80 (d, 1H, J=9.0 Hz), 7.57-7.64 (m, 1H), 7.74-7.77 (m, 1H), 7.92-7.99 (m, 2H), 8.18 (d, 1H, J=6.0 Hz).

Step 5

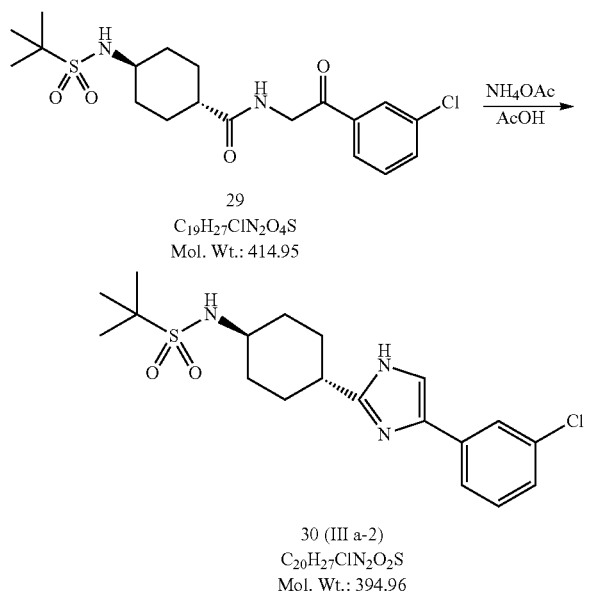

Compound 29 obtained in Step 4 (598 mg, 1.44 mmol) was dissolved in acetic acid (10 ml). To the solution was added ammonium acetate (3.33 g, 43.2 mmol) and the mixture was stirred and refluxed for 8 hours.

The reactant was neutralized with saturated sodium hydrogen carbonate solution and extracted with ethyl acetate. The organic layer was washed with water and saturated sodium chloride solution and dried over magnesium sulfate. The solvent was removed under reduced pressure and the residue was purified by silica gel chromatography. During removing the solvent under reduced pressure, solid was deposited. To the solid was added diisopropyl ether and the mixture was stirred at room temperature. The deposited solid was collected with filtration to give the desired Compound 30 (402 mg, yield 71%).

$^1$H-NMR (DMSO-$d_6$) δ: 1.31 (s, 9H), 1.37-1.63 (m, 4H), 2.00-2.03 (m, 4H), 2.57-2.65 (m, 1H), 3.07-3.20 (m, 1H), 6.85 (d, 1H, J=8.4 Hz), 7.38-7.18 (m, 2H), 7.61-7.79 (m, 3H), 11.85 (s, 1H).

Example 5

Synthesis of Compound (IIIb-3)

Step 1

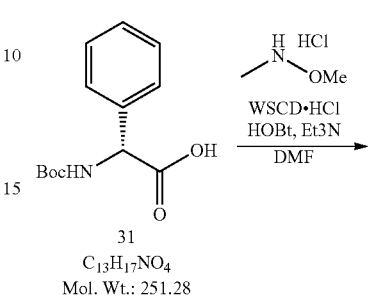

Carboxylic acid 31 (2.00 g, 7.96 mmol), WSCD hydrochloride (1.98 g, 10.4 mmol) and HOBt (0.13 g, 0.96 mmol) were dissolved in N,N-dimethylformamide (20 ml). To the solution were added N,O-dimethylhydroxy ammonium chloride (0.85 g, 8.76 mmol) and triethylamine (1.43 ml, 10.4 mmol) and the mixture was stirred at room temperature for 2 hours. The reactant was poured into water and extracted with ethyl acetate. The organic layer was washed with water and dried over magnesium sulfate. The solvent was removed under reduced pressure and the residue was purified by silica gel chromatography to give the desired Compound 32 (1.21 g, yield 52%).

$^1$H-NMR (DMSO-$d_6$) δ: 1.40 (s, 9H), 3.11 (s, 3H), 3.55 (s, 3H), 5.60 (d, 1H, J=6.0 Hz), 7.31-7.42 (m, 6H).

Step 2

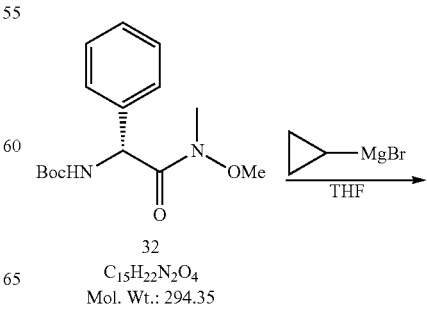

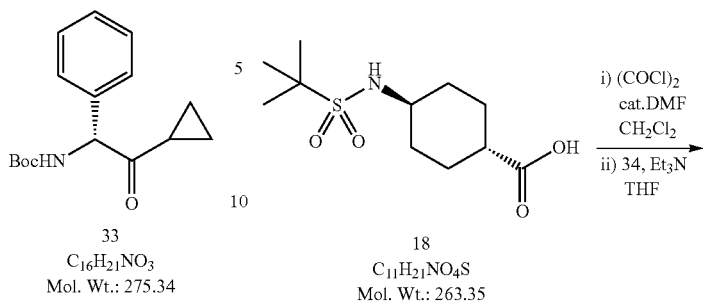

33
C₁₆H₂₁NO₃
Mol. Wt.: 275.34

Compound 32 obtained in Step 1 (494 mg, 1.68 mmol) was dissolved in tetrahydrofuran (5 ml). To the solution was added carefully cyclopropyl magnesium bromide (1M, 10 ml, 10.0 mmol) at 0° C. and the mixture was stirred at room temperature for 3 hours. The reactant was poured into saturated ammonium chloride solution and extracted with ethyl acetate. The organic layer was washed with water and dried over magnesium sulfate. The solvent was removed under reduced pressure and the residue was purified by silica gel chromatography to give the desired Compound 33 (438 mg, yield 95%).

Step 3

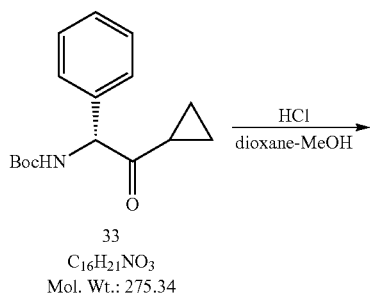

33
C₁₆H₂₁NO₃
Mol. Wt.: 275.34

34
C₁₁H₁₄ClNO
Mol. Wt.: 211.69

Compound 33 obtained in Step 2 (295 mg, 1.06 mmol) was dissolved in methanol (5 ml). To the solution was added hydrochloric acid in dioxane (4 M, 1.1 ml, 4.25 mmol) at 0° C. and the mixture was stirred at room temperature overnight. The solvent was removed under reduced pressure. To the residue were added ethyl acetate and diisopropyl ether and the deposited solid was collected with filtration to give the desired amine hydrochloride 34 (337 mg, yield 90%).

Step 4

18
C₁₁H₂₁NO₄S
Mol. Wt.: 263.35

35
C₂₂H₃₂N₂O₄S
Mol. Wt.: 420.57

Carboxylic acid 18 (The synthesis method disclosed in WO2001/037826) (416 mg, 1.58 mmol) was suspended in methylene chloride (4 ml). To the mixture were added oxalyl chloride (0.17 ml, 1.89 mmol) and 2 drops of N,N-dimethylformamide carefully and the mixture was stirred at room temperature for 1 hour.

In the other reaction container, Compound 34 obtained in Step 3 (304 mg, 1.44 mmol) was suspended in tetrahydrofuran (4 ml). To the mixture were added dropwise methylene chloride solution obtained as above and triethylamine (0.80 ml, 5.74 mmol) at 0° C. and the mixture was stirred at room temperature for 2 hours. The reactant was poured into saturated sodium hydrogen carbonate solution and extracted with ethyl acetate. The organic layer was washed with water and saturated sodium chloride solution and dried over magnesium sulfate. The solvent was removed under reduced pressure and the obtained residue was used for the next step without purification.

Step 5

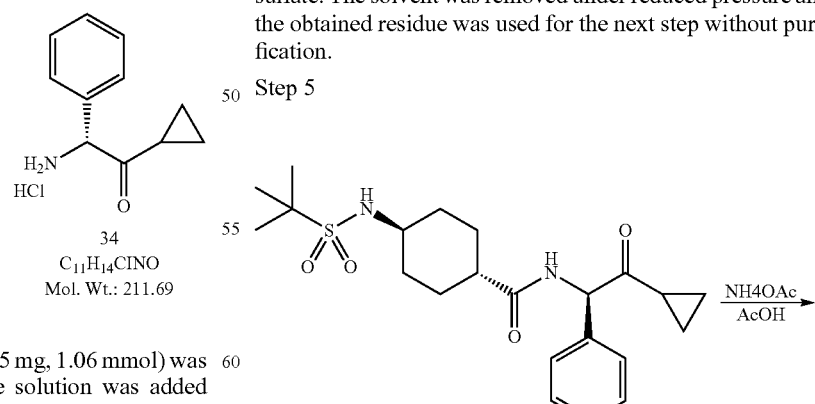

35
C₂₂H₃₂N₂O₄S
Mol. Wt.: 420.57

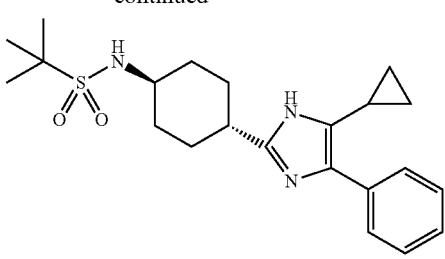

36 (III b-3)
C$_{22}$H$_{31}$N$_3$O$_2$S
Mol. Wt.: 401.57

The residue of Compound 35 obtained in Step 5 was dissolved in acetic acid (10 ml). To the solution was added ammonium acetate (3.31 g, 43.1 mmol) and the mixture was stirred and refluxed for 2 hours. The reactant was neutralized with saturated sodium hydrogen carbonate solution and extracted with ethyl acetate. The organic layer was washed with water and saturated sodium chloride solution and dried over magnesium sulfate. The solvent was removed under reduced pressure and the residue was purified by silica gel chromatography. To the residue obtained by removing the solvent under reduced pressure were added ethyl acetate, ethanol and hexane and the deposited solid was collected with filtration to give the desired Compound 36 (88.4 mg, yield 15% (2 Steps)).

$^1$H-NMR (DMSO-d$_6$) δ: 1.20-1.65 (m, 8H), 1.30 (s, 9H), 1.90-2.00 (m, 4H), 2.52-2.60 (m, 1H), 2.99-3.17 (m, 2H), 6.60-7.71 (m, 6H), 12.09 (s, 1H).

Example 6

Synthesis of Compound (IVa-7)

Step 1

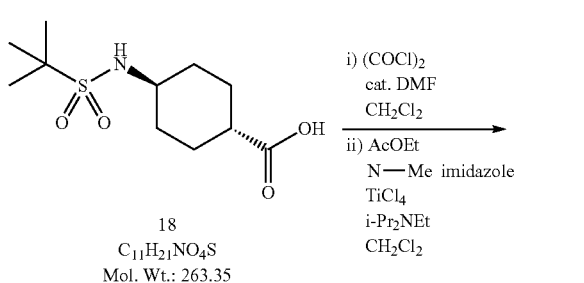

18
C$_{11}$H$_{21}$NO$_4$S
Mol. Wt.: 263.35 i) (COCl)$_2$
cat. DMF
CH$_2$Cl$_2$ ii) AcOEt
N—Me imidazole
TiCl$_4$
i-Pr$_2$NEt
CH$_2$Cl$_2$

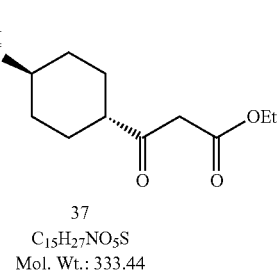

37
C$_{15}$H$_{27}$NO$_5$S
Mol. Wt.: 333.44

To Carboxylic acid 18 (The synthesis method disclosed in WO2001037826) (79 g, 300 mmol) was added methylene chloride (400 ml). To the mixture were added N,N'-dimethylformamide (700 μL, 9.0 mmol) and oxalyl chloride (27.0 mL, 309 mmol) at 4° C. The mixture was stirred at room temperature for 1 hour and the reactant was condensed under reduced pressure to give acid chloride.

To N-methylimidazole (28.7 mL, 309 mmol) in a solution of methylene chloride (400 ml) and ethyl acetate (28.7 mL, 309 mmol), was added acid chloride (300 mmol) in methylene chloride (400 ml) at −60° C. and then added dropwise titanium tetrachloride (99 mL, 900 mmol) at the same time, and the mixture was stirred for 30 minutes. To the reactant was added N,N'-diisopropylethylamine (172 mL, 990 mmol) and the mixture was stirred at −40° C. for 40 minutes. To the mixture was added water and extracted with chloroform. The organic layer was washed with saturated saline and dried over magnesium sulfate. The solvent was removed under reduced pressure and the obtained residue was recrystallized from the mixed solvent of ethyl acetate and hexane to give Compound 37 (78.6 g, yield 79%) as colorless solid.

$^1$H-NMR (DMSO-d$_6$) δppm: 1.18 (t, 3H, J=7.0 Hz), 1.18-1.35 (m, 4H), 1.25 (s, 9H), 1.81-1.97 (m, 4H), 2.37 (m, 1H), 3.00 (m, 1H), 3.63 (s, 2H), 4.08 (q, 2H, J=7.0 Hz), 6.79 (d, 1H, J=8.6 Hz).

Step 2

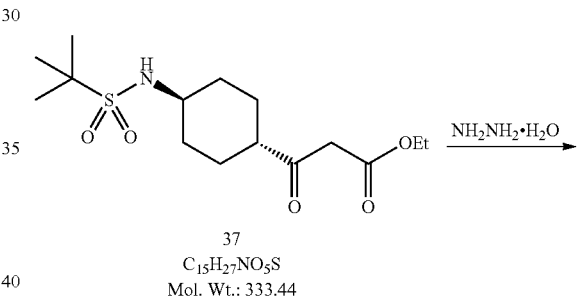

37
C$_{15}$H$_{27}$NO$_5$S
Mol. Wt.: 333.44

NH$_2$NH$_2$·H$_2$O →

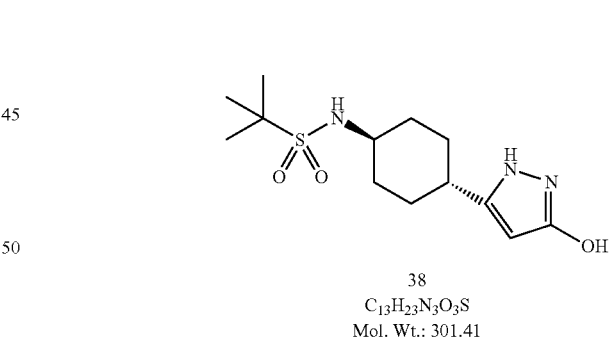

38
C$_{13}$H$_{23}$N$_3$O$_3$S
Mol. Wt.: 301.41

Diketoester 37 (15.00 g, 45.0 mmol) was suspended in methanol (105 ml). To the mixture was added hydrazine monohydrate (6.55 ml, 135 mmol) and the mixture was stirred for 1 hour at room temperature. The reactant was poured into water (400 ml) and stirred at room temperature. The deposited solid was collected with filtration and washed with water and dried under reduced pressure and heating to give the desired 3-hydroxypyrazole 38 (12.22 g, yield 90%).

$^1$H-NMR (d$_6$-DMSO) δppm: 1.26 (s, 9H), 1.30-1.50 (m, 4H), 1.80-2.02 (m, 4H), 2.36 (m, 1H), 3.05 (m, 1H), 5.21 (s, 1H), 6.81 (d, 1H, J=8.7 Hz), 9.40 (brs, 1H), 11.20 (brs, 1H).

Step 3

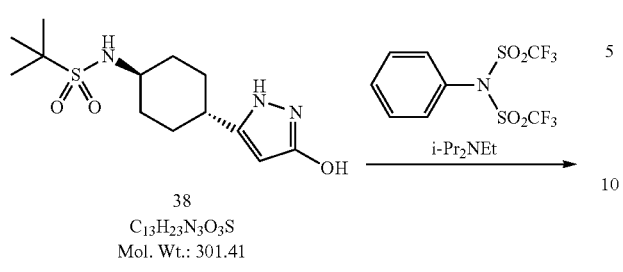

38
C₁₃H₂₃N₃O₃S
Mol. Wt.: 301.41

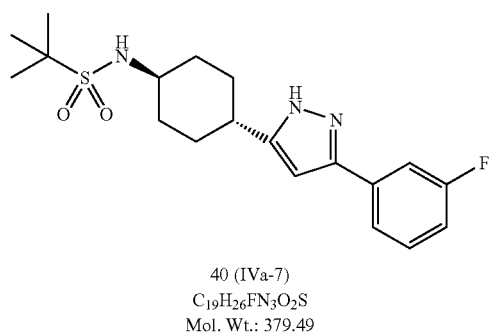

40 (IVa-7)
C₁₉H₂₆FN₃O₂S
Mol. Wt.: 379.49

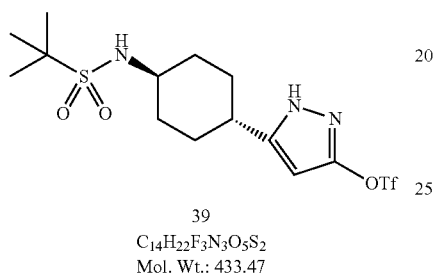

39
C₁₄H₂₂F₃N₃O₅S₂
Mol. Wt.: 433.47

3-hydroxypyrazole 38 (12.22 g, 40.5 mmol) was suspended in tetrahydrofuran (250 ml). To the mixture were added N,N-diisopropylethylamine (21.2 ml, 122 mmol) and N-phenyl trifluoromethanesulfonamide (17.38 g, 48.7 mmol) and the mixture was refluxed for 3 hours under heating. The reactant was poured into dilute hydrochloric acid solution to acidize and extracted with ethyl acetate. The organic layer was washed with water and then saturated saline, and dried over anhydrous magnesium sulfate. The solvent was removed under reduced pressure and the residue was purified by column chromatography and recrystallized from ethyl acetate and n-hexane to give the desired triflate 39 (12.19 g, yield 69%).

¹H-NMR (d₆-DMSO) δppm: 1.27 (s, 9H), 1.34-1.54 (m, 4H), 1.86-2.05 (m, 4H), 2.55 (m, 1H), 3.10 (m, 1H), 6.15 (s, 1H), 6.84 (d, 1H, J=8.7 Hz), 12.86 (brs, 1H).

Step 4

Compound 39 obtained in Step 3 (350 mg, 0.81 mmol), 3-fluoro phenyl boronate (339 mg, 2.42 mmol), potassium phosphate (514 mg, 2.42 mmol), potassium bromide (106 mg, 0.89 mmol) and tetrakis triphenylphosphine palladium complex (28.0 mg, 24.0 μmol) were suspended in 1,4-dioxane (6.5 ml) and the mixture was in sealed tubes and stirred by a microwave reactor for 30 minutes at 160° C. The reactant was poured into water and extracted with ethyl acetate. The organic layer was washed with water and saturated sodium chloride solution and dried over magnesium sulfate. The solvent was removed under reduced pressure and the residue was purified by silica gel chromatography. To the residue obtained by removing the solvent under reduced pressure, were added ethyl acetate and hexane and the deposited solid was collected with filtration to give the desired Compound 40 (210.9 mg, yield 69%).

¹H-NMR (DMSO-d₆) δ: 1.30 (s, 9H), 1.37-1.52 (m, 4H), 1.99-2.03 (m, 4H), 2.52-2.60 (m, 1H), 3.07-3.19 (m, 1H), 6.55 (s, 1H), 6.88 (d, 1H, J=9.0 Hz), 7.08-7.13 (m, 1H), 7.40-7.64 (m, 3H), 12.69 (s, 1H).

Example 7

Synthesis of Compound (IVb-26)

Step 1

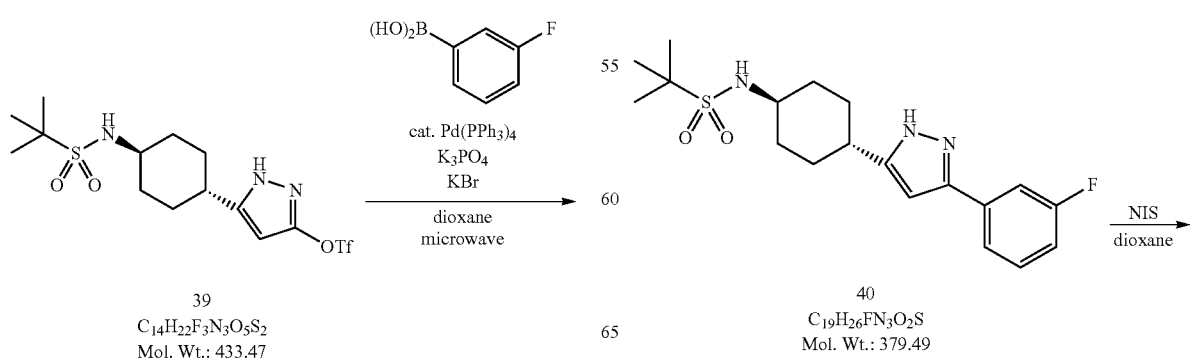

39
C₁₄H₂₂F₃N₃O₅S₂
Mol. Wt.: 433.47

40
C₁₉H₂₆FN₃O₂S
Mol. Wt.: 379.49

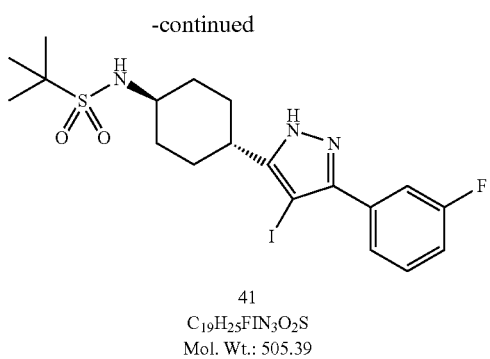

41
C₁₉H₂₅FIN₃O₂S
Mol. Wt.: 505.39

Compound 40 (200 mg, 0.527 mmol) was dissolved in dioxane (4 ml). To the mixture was added N-iodosuccinimide (142 mg, 0.632 mmol) and the mixture was stirred for 30 minutes at 80° C. The reactant was poured into thiosodium sulphate solution and extracted with ethyl acetate. The organic layer was washed with water and dried over anhydrous magnesium sulfate. The solvent was removed under reduced pressure and the deposited solid was washed with the mixed solvent of hexane/ethyl acetate (5/1) and collected with filtration to give the desired substituted Pyrazole 41 (221 mg, yield 83%). This product is racemic mixture and the ratio is 3:1.

$^1$H-NMR (CDCl₃) δ: 1.29 (s, 9H), 1.39-1.67 (m, 4H), 1.85-2.03 (m, 4H), 2.65 (t, 1H, J=12.0 Hz), 3.13 (d, 1H, J=7.6 Hz), 6.82 (d, 1H, J=8.0 Hz, minor), 6.97 (d, 1H, J=8.4 Hz, major), 7.21 (t, 1H, J=8.0 Hz, major), 7.31 (t, 1H, J=7.6 Hz, minor), 7.42-7.56 (m, 2H), 7.65 (d, 1H, J=7.6 Hz, major), 13.2 (s, 1H, major), 13.3 (s, 1H, minor).

Step 2

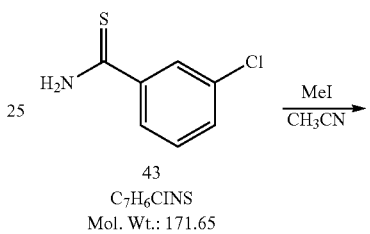

41
C₁₉H₂₅FIN₃O₂S
Mol. Wt.: 505.39

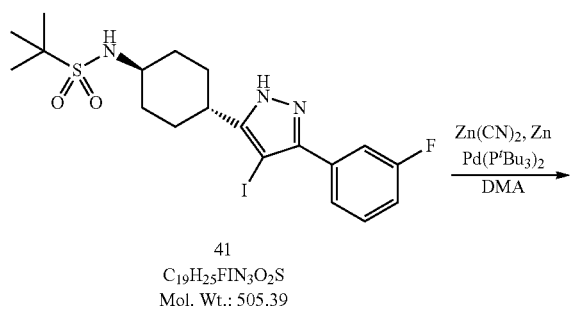

42 (IVb-26)
C₂₀H₂₅FN₄O₂S
Mol. Wt.: 404.5

Compound 41 obtained in Step 1 (221 mg, 0.437 mmol), zinc powder (5.7 mg, 0.087 mmol) and zinc potassium (30 mg, 0.254 mmol) were dissolved in dimethylacetamide (4 ml). To the solution was added Pd(P$^t$Bu₃)₂ (22 mg, 0.044 mmol) under nitrogen gas and the mixture was stirred for 3 hours at 95° C. The reactant was poured into water and extracted with ethyl acetate. The organic layer was washed with water and dried over anhydrous magnesium sulfate. The filtrate was condensed under reduced pressure and the residue was purified by silica gel chromatography to give the desired nitrile 42 (72 mg, yield 41%).

$^1$H-NMR (DMSO-d₆) δ: 1.28 (s, 9H), 1.36-1.52 (m, 2H), 1.58-1.76 (m, 2H), 1.94-2.08 (m, 4H), 2.72-2.90 (m, 1H), 3.06-3.20 (m, 1H), 6.99 (d, 1H, J=6.0 Hz), 7.24-7.38 (m, 1H), 7.52-7.72 (m, 3H), 13.68 (s, 1H×4/5), 13.88 (s, 1H×1/5).

Example 8

Synthesis of Compound (Va-5)

Step 1

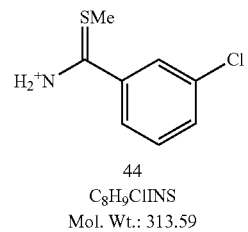

43
C₇H₆ClNS
Mol. Wt.: 171.65

44
C₈H₉ClINS
Mol. Wt.: 313.59

3-chlorothioamide 43 (3 g, 17.48 mmol) was dissolved in acetonitrile (52 mL). To the solution was added MeI (5.44 mL, 87.00 mmol) at room temperature with stirring. Then, the mixture was stirred in oil bath of 80° C. for 2 hours. The mixture was cooled to room temperature and the deposited solid was collected with filtration and washed with acetonitrile to give the desired Compound 44 (5 g, 91%).

$^1$H-NMR (DMSO-d₆) δ: 2.81 (s, 3H), 7.68 (t, 1H, J=8.0 Hz), 7.82 (d, 1H, J=8.0 Hz), 7.87 (d, 1H, J=8.0 Hz), 7.93 (s, 1H).

Step 2

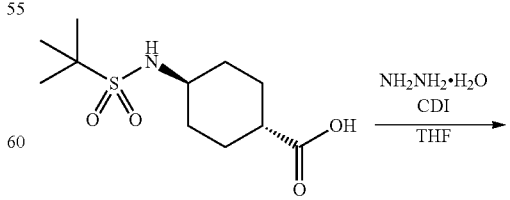

18
C₁₁H₂₁NO₄S
Mol. Wt.: 263.35

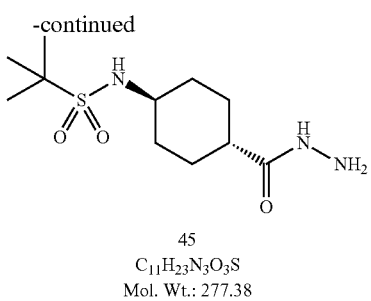

45
C₁₁H₂₃N₃O₃S
Mol. Wt.: 277.38

Carboxylic acid 18 (20 g, 76 mmol) was dissolved in THF (150 mL). With stirring at room temperature, carbonyldiimidazole (13.55 g, 84 mmol) was added to the solution. After stirring at room temperature for 30 minutes, the obtained white suspension was added dropwise in hydrazine monohydrate (18.42 mL, 380 mmol) in THF (150 mL) at 0° C. The mixture was cooled to room temperature and stirred for 50 minutes. The solid was collected with filtration and washed with THF to give the desired hydrazide 45 (16.25 g, 77%).

¹H-NMR (DMSO-d₆) δ: 1.18-1.32 (m, 2H), 1.25 (s, 9H), 1.32-1.46 (m, 2H), 1.60-1.73 (m, 2H), 1.84-2.00 (m, 3H), 2.93-3.06 (m, 1H), 4.15 (brs, 2H), 6.75 (d, 1H, J=8.0 Hz), 8.87 (s, 1H).

Step 3

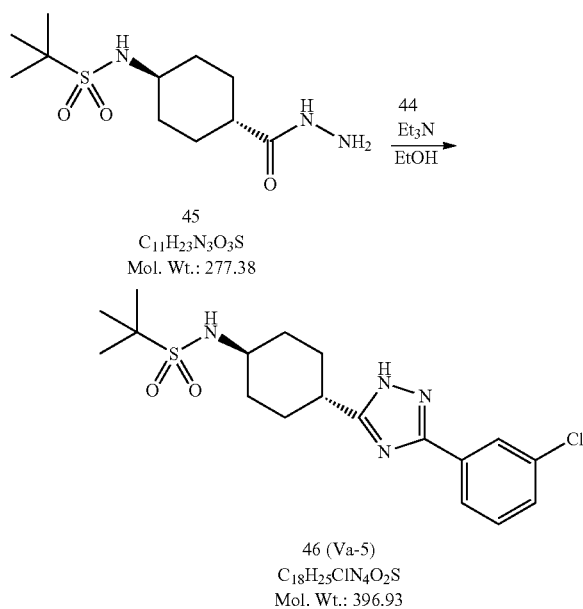

45
C₁₁H₂₃N₃O₃S
Mol. Wt.: 277.38

46 (Va-5)
C₁₈H₂₅ClN₄O₂S
Mol. Wt.: 396.93

Hydrazide 45 (1.50 g, 5.41 mmol) and Compound 44 (4.24 g, 13.52 mmol) was dissolved in ethanol (20 mL). With stirring at room temperature, triethylamine (1.88 mL, 13.52 mmol) was added to the solution. The mixture was stirred in oil bath of 80° C. for 12 hours. After removing ethanol under reduced pressure, the residue was purified by silica gel column chromatography. The residue was recrystallized from ethyl acetate:hexane (1:1) to give the desired Compound 46 (1245 mg, 58%).

¹H-NMR (DMSO-d₆) δ: 1.28 (s, 9H), 1.36-1.45 (m, 2H), 1.46-1.64 (m, 2H), 1.94-2.12 (m, 4H), 2.64-2.76 (m, 1H), 3.06-3.20 (m, 1H), 6.85 (d, 1H, J=8.0 Hz), 7.34-7.53 (m, 2H), 13.83 (brs, 1H).

The following compounds synthesized in similar methods also include this invention.

Compound Ia-1

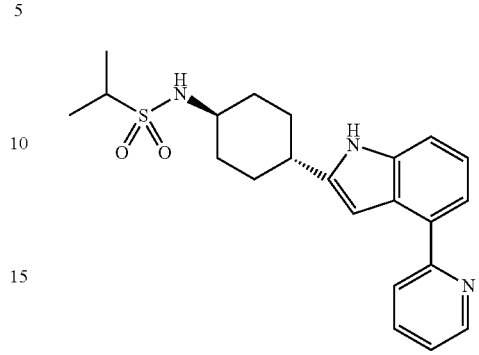

¹H-NMR (DMSO-d₆) δ: 1.24 (d, 6H, J=6.6 Hz), 1.36-1.66 (m, 4H), 1.96-2.14 (m, 4H), 2.67 (t, 1H, J=11.4 Hz), 3.13-3.36 (m, 2H), 6.64 (s, 1H), 7.05 (d, 1H, J=7.2 Hz), 7.12 (t, 1H, J=7.8 Hz), 7.28-7.40 (m, 2H), 7.46 (d, 1H, J=7.2 Hz), 7.87 (d, 1H, J=5.4 Hz), 8.69 (s, 1H), 11.08 (s, 1H).

Compound Ia-2

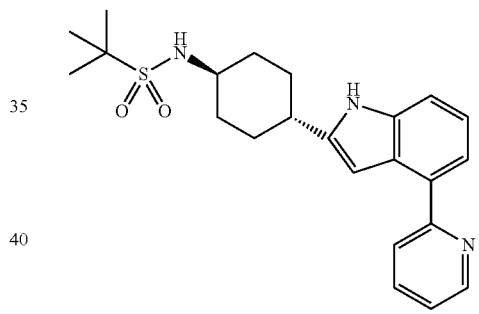

¹H-NMR (DMSO-d₆) δ: 1.29 (s, 9H), 1.36-1.66 (m, 4H), 1.96-2.14 (m, 4H), 2.67 (t, 1H, J=11.4 Hz), 3.06-3.26 (m, 1H), 6.64 (s, 1H), 6.86 (d, 1H, J=7.2 Hz), 7.11 (t, 1H, J=7.8 Hz), 7.28-7.40 (m, 2H), 7.45 (d, 1H, J=7.2 Hz), 7.87 (d, 2H, J=3.9 Hz), 8.69 (d, 1H, J=4.5 Hz), 11.07 (s, 1H).

Compound Ia-3

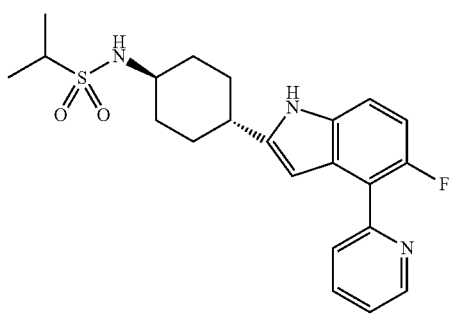

$^1$H-NMR (DMSO-d$_6$) δ: 1.23 (d, 6H, J=6.9 Hz), 1.32-1.60 (m, 4H), 1.96-2.10 (m, 4H), 2.62 (t, 1H, J=11.4 Hz), 3.06-3.20 (m, 2H), 6.30 (s, 1H), 6.91-6.98 (m, 1H), 7.04 (d, 1H, J=7.8 Hz), 7.28-7.40 (m, 2H), 7.64 (d, 1H, J=7.8 Hz), 7.89 (td, 1H, J=7.8, 1.5 Hz), 8.74 (d, 1H, J=4.8 Hz), 11.10 (s, 1H).

$^1$H-NMR (DMSO-d$_6$) δ: 1.24 (d, 6H, J=6.6 Hz), 1.35-1.63 (m, 4H), 1.96-2.15 (m, 4H), 2.64 (t, 1H, J=11.4 Hz), 3.07-3.22 (m, 2H), 6.21 (s, 1H), 7.04 (d, 1H, J=7.8 Hz), 7.20-7.27 (m, 1H), 7.35 (d, 1H, J=8.7 Hz), 7.76-7.83 (m, 2H), 7.90 (d, 1H, J=8.1 Hz), 8.16 (s, 1H), 8.57-8.62 (m, 1H), 11.00 (s, 1H).

Compound Ia-4

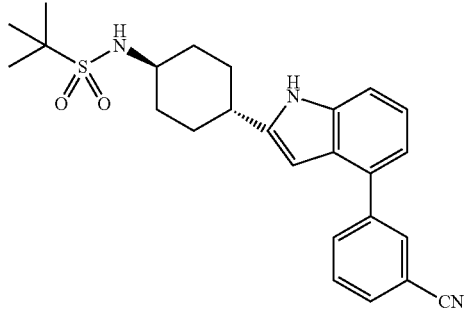

Compound Ia-7

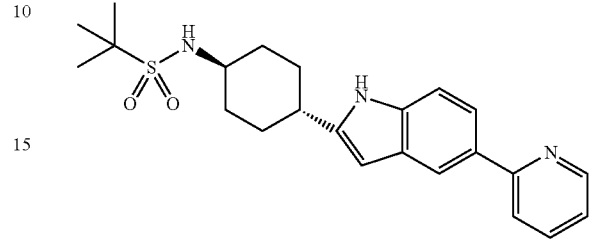

$^1$H-NMR (DMSO-d$_6$) δ: 1.29 (s, 9H), 1.35-1.63 (m, 4H), 1.97-2.14 (m, 4H), 2.64 (t, 1H, J=11.4 Hz), 3.06-3.23 (m, 1H), 6.20 (s, 1H), 6.85 (d, 1H, J=8.7 Hz), 7.18-7.25 (m, 1H), 7.33 (d, 1H, J=8.4 Hz), 7.77-7.81 (m, 2H), 7.89 (d, 1H, J=8.1 Hz), 8.15 (s, 1H), 8.57-8.62 (m, 1H), 10.99 (s, 1H).

$^1$H-NMR (DMSO-d$_6$) δ: 1.28 (s, 9H), 1.36-1.66 (m, 4H), 1.96-2.10 (m, 4H), 2.66 (t, 1H, J=11.4 Hz), 3.06-3.20 (m, 1H), 6.29 (s, 1H), 6.86 (d, 1H, J=8.4 Hz), 7.16-7.05 (m, 2H), 7.35 (d, 1H, J=7.2 Hz), 7.69 (t, 1H, J=7.5 Hz), 7.83 (d, 1H, J=7.8 Hz), 7.99 (d, 1H, J=8.1 Hz), 8.02 (s, 1H), 11.16 (s, 1H).

Compound Ia-8

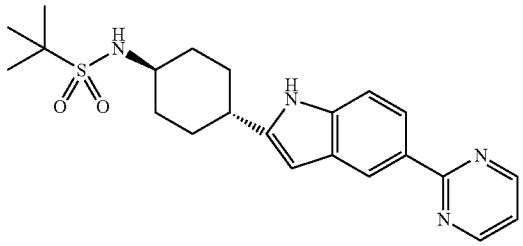

$^1$H-NMR (DMSO-d$_6$) δ: 1.29 (s, 9H), 1.38-1.64 (m, 4H), 1.97-2.16 (m, 4H), 2.64 (t, 1H, J=11.4 Hz), 3.08-3.24 (m, 1H), 6.24 (s, 1H), 6.85 (d, 1H, J=8.7 Hz), 7.29 (t, 1H, J=4.8 Hz), 7.35 (d, 1H, J=8.4 Hz), 8.12 (dd, 1H, J=8.4, 1.5 Hz), 8.53 (s, 1H), 8.80 (d, 2H, J=4.8 Hz), 11.09 (s, 1H).

Compound Ia-5

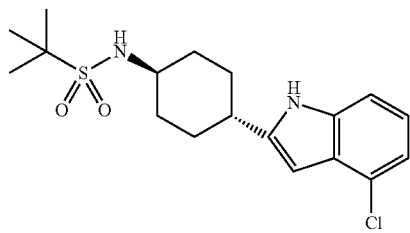

$^1$H-NMR (DMSO-d$_6$) δ: 1.29 (s, 9H), 1.36-1.64 (m, 4H), 1.96-2.10 (m, 4H), 2.65 (t, 1H, J=11.4 Hz), 3.08-3.22 (m, 1H), 6.16 (s, 1H), 6.87 (d, 1H, J=9.0 Hz), 6.95-7.03 (m, 2H), 7.21-7.29 (m, 1H), 11.25 (s, 1H).

Compound Ia-9

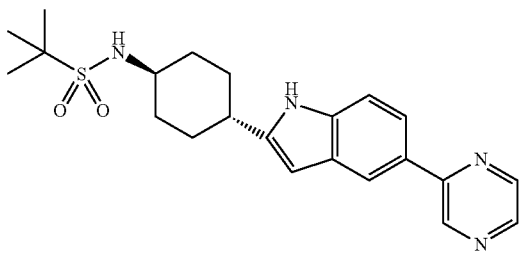

Compound Ia-6

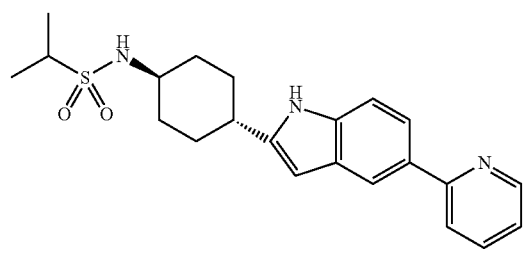

$^1$H-NMR (DMSO-d$_6$) δ: 1.29 (s, 9H), 1.37-1.63 (m, 4H), 1.96-2.12 (m, 4H), 2.65 (t, 1H, J=11.4 Hz), 3.06-3.23 (m, 1H), 6.23 (s, 1H), 6.86 (d, 1H, J=8.7 Hz), 7.38 (d, 1H, J=8.4 Hz), 7.82 (dd, 1H, J=8.7, 1.5 Hz), 8.23 (s, 1H), 8.47 (d, 1H, J=2.7 Hz), 8.60-8.64 (m, 1H), 9.19 (d, 1H, J=1.5 Hz), 11.10 (s, 1H).

Compound Ia-10

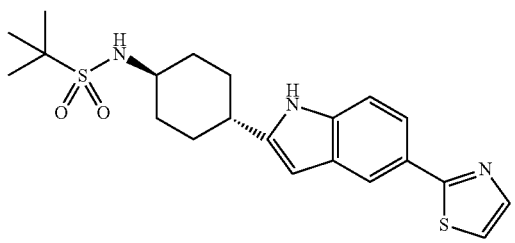

¹H-NMR (DMSO-d₆) δ: 1.29 (s, 9H), 1.37-1.63 (m, 4H), 1.96-2.12 (m, 4H), 2.64 (t, 1H, J=11.4 Hz), 3.07-3.23 (m, 1H), 6.24 (s, 1H), 6.86 (d, 1H, J=8.4 Hz), 7.35 (d, 1H, J=8.4 Hz), 7.61-7.67 (m, 2H), 7.82 (d, 1H, J=3.3 Hz), 8.02 (s, 1H), 11.15 (s, 1H).

Compound Ia-11

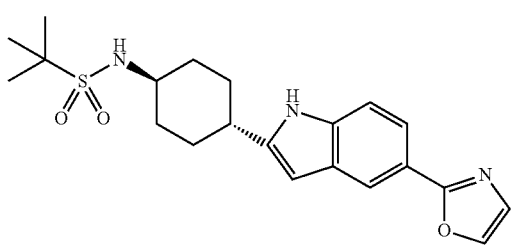

¹H-NMR (DMSO-d₆) δ: 1.29 (s, 9H), 1.37-1.63 (m, 4H), 1.96-2.12 (m, 4H), 2.65 (t, 1H, J=11.4 Hz), 3.07-3.22 (m, 1H), 6.26 (s, 1H), 6.86 (d, 1H, J=9.0 Hz), 7.29 (s, 1H), 7.38 (d, 1H, J=8.4 Hz), 7.67 (dd, 1H, J=8.4, 1.5 Hz), 8.06-8.12 (m, 2H), 11.20 (s, 1H).

Compound Ia-12

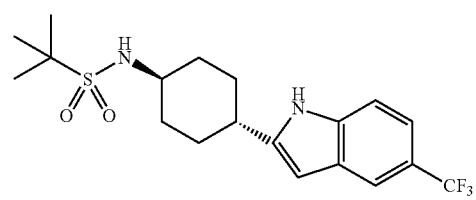

¹H-NMR (DMSO-d₆) δ: 1.29 (s, 9H), 1.37-1.64 (m, 4H), 1.98-2.12 (m, 4H), 2.67 (t, 1H, J=11.4 Hz), 3.08-3.24 (m, 1H), 6.30 (s, 1H), 6.86 (d, 1H, J=8.7 Hz), 7.28 (d, 1H, J=8.4 Hz), 7.44 (d, 1H, J=8.4 Hz), 7.80 (s, 1H), 11.35 (s, 1H).

Compound Ia-13

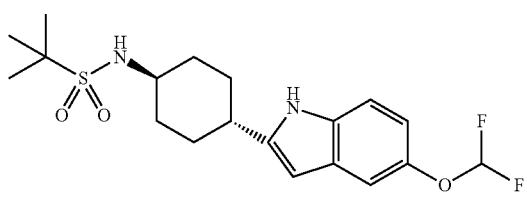

¹H-NMR (DMSO-d₆) δ: 1.28 (s, 9H), 1.38-1.60 (m, 4H), 1.98-2.08 (m, 4H), 2.62 (t, 1H, J=11.4 Hz), 3.08-3.20 (m, 1H), 6.14 (s, 1H), 6.80-6.87 (m, 2H), 7.03 (s, 1H), 7.18-7.22 (m, 1H), 7.27 (d, 1H, J=6.3 Hz), 10.99 (s, 1H).

Compound Ia-14

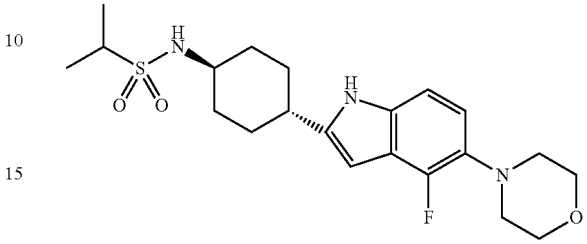

¹H-NMR (DMSO-d₆) δ: 1.23 (d, 6H, J=6.9 Hz), 1.32-1.60 (m, 4H), 1.92-2.08 (m, 4H), 2.59 (t, 1H, J=11.4 Hz), 2.88-2.96 (m, 4H), 3.05-3.20 (m, 2H), 3.70-3.76 (m, 4H), 6.09 (s, 1H), 6.81 (t, 1H, J=8.7 Hz), 6.88-7.08 (m, 2H), 10.96 (s, 1H).

Compound Ia-15

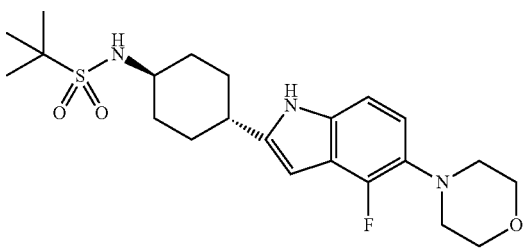

¹H-NMR (DMSO-d₆) δ: 1.28 (s, 9H), 1.34-1.60 (m, 4H), 1.95-2.08 (m, 4H), 2.59 (t, 1H, J=11.4 Hz), 2.88-2.95 (m, 4H), 3.05-3.20 (m, 1H), 3.70-3.76 (m, 4H), 6.09 (s, 1H), 6.77-6.87 (m, 2H), 7.01 (d, 1H, J=8.7 Hz), 10.95 (s, 1H).

Compound Ia-16

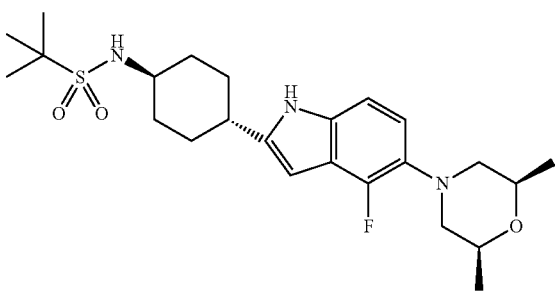

¹H-NMR (DMSO-d₆) δ: 1.11 (d, 6H, J=6.3 Hz), 1.28 (s, 9H), 1.34-1.60 (m, 4H), 1.94-2.08 (m, 4H), 2.37 (t, 2H, J=10.8 Hz), 2.59 (t, 1H, J=11.4 Hz), 3.02-3.20 (m, 3H), 3.68-3.82 (m, 2H), 6.08 (s, 1H), 6.77-6.88 (m, 2H), 7.00 (d, 1H, J=8.4 Hz), 10.94 (s, 1H).

Compound Ia-17

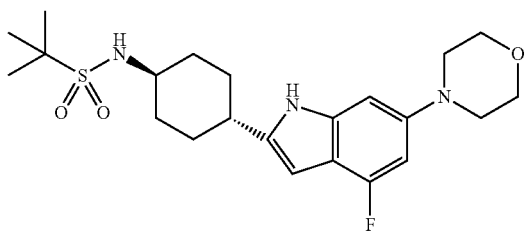

¹H-NMR (DMSO-d₆) δ: 1.28 (s, 9H), 1.38-1.60 (m, 4H), 1.94-2.08 (m, 4H), 2.56 (t, 1H, J=11.4 Hz), 3.00-3.06 (m, 4H), 3.06-3.20 (m, 1H), 3.70-3.80 (m, 4H), 6.01 (s, 1H), 6.47-6.58 (m, 2H), 6.83 (d, 1H, J=8.7 Hz), 10.85 (s, 1H).

Compound Ia-18

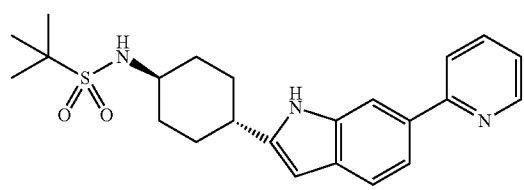

¹H-NMR (DMSO-d₆) δ: 1.29 (s, 9H), 1.38-1.65 (m, 4H), 1.96-2.14 (m, 4H), 2.66 (t, 1H, J=11.4 Hz), 3.08-3.26 (m, 1H), 6.16 (s, 1H), 6.87 (d, 1H, J=8.1 Hz), 7.22-7.28 (m, 1H), 7.48 (d, 1H, J=8.4 Hz), 7.68 (d, 1H, J=8.4 Hz), 7.82 (td, 1H, J=7.8, 1.5 Hz), 7.91 (d, 1H, J=7.5 Hz), 8.03 (s, 1H), 8.62 (d, 1H, J=4.8 Hz), 11.04 (s, 1H).

Compound Ia-19

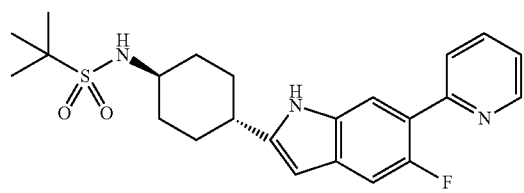

¹H-NMR (DMSO-d₆) δ: 1.29 (s, 9H), 1.36-1.63 (m, 4H), 1.96-2.14 (m, 4H), 2.66 (t, 1H, J=11.4 Hz), 3.08-3.26 (m, 1H), 6.17 (s, 1H), 6.86 (d, 1H, J=8.4 Hz), 7.28 (d, 1H, J=12.6 Hz), 7.29-7.36 (m, 1H), 7.74-7.88 (m, 3H), 8.69 (d, 1H, J=4.5 Hz), 11.11 (s, 1H).

Compound Ia-20

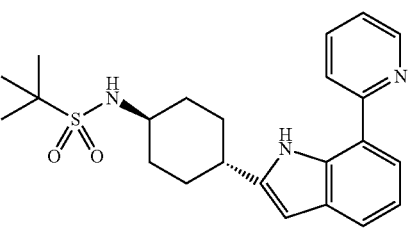

¹H-NMR (DMSO-d₆) δ: 1.29 (s, 9H), 1.40-1.64 (m, 4H), 1.96-2.16 (m, 4H), 2.82 (t, 1H, J=11.4 Hz), 3.12-3.28 (m, 1H), 6.23 (s, 1H), 6.87 (d, 1H, J=8.7 Hz), 7.08 (t, 1H, J=7.8 Hz), 7.36 (dd, 1H, J=7.2, 4.8 Hz), 7.53 (d, 1H, J=7.8 Hz), 7.70 (d, 1H, J=7.8 Hz), 7.92 (t, 1H, J=7.8 Hz), 8.11 (d, 1H, J=8.1 Hz), 8.79 (d, 1H, J=3.9 Hz), 11.23 (s, 1H).

Compound Ib-1

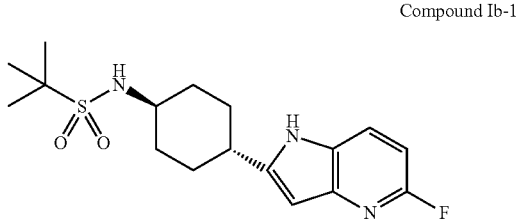

¹H-NMR (DMSO-d₆) δ: 1.28 (s, 9H), 1.28-1.61 (m, 4H), 1.99-2.03 (m, 4H), 2.63-2.70 (m, 1H), 3.08-3.18 (m, 1H), 6.19 (s, 1H), 6.68 (dd, 1H, J=1.5, 8.5 Hz), 6.86 (d, 1H, J=8.5 Hz), 7.73-7.78 (m, 1H), 11.31 (s, 1H).

Compound Ib-2

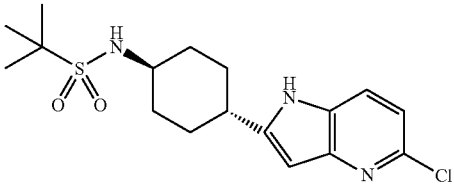

¹H-NMR (DMSO-d₆) δ: 1.28 (s, 9H), 1.40-1.60 (m, 4H), 1.99-2.08 (m, 4H), 2.63-2.71 (m, 1H), 3.08-3.16 (m, 1H), 6.26 (s, 1H), 6.85 (d, 1H, J=8.4 Hz), 7.02 (d, 1H, J=8.4 Hz), 7.68 (d, 1H, J=8.4 Hz), 11.38 (s, 1H).

Compound Ib-3

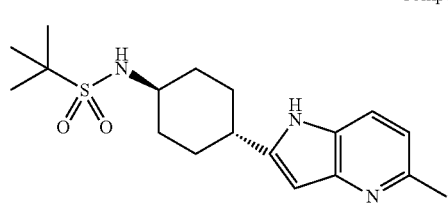

¹H-NMR (DMSO-d₆) δ: 1.27 (s, 9H), 1.37-1.59 (m, 4H), 1.96-2.05 (m, 4H), 2.45 (s, 3H), 2.58-2.67 (m, 1H), 3.10-3.16 (m, 1H), 6.12 (m, 1H), 6.84 (d, 1H, J=8.2 Hz), 6.85 (d, 1H, J=8.7 Hz), 7.47 (d, 1H, J=8.2 Hz), 10.92 (s, 1H).

Compound Ib-4

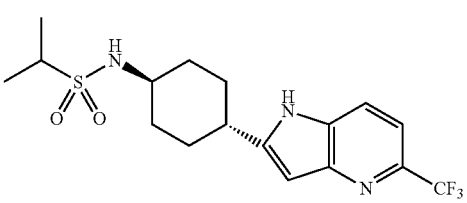

¹H-NMR (DMSO-d₆) δ: 1.24 (d, 6H, J=6.6 Hz), 1.36-1.66 (m, 4H), 1.96-2.16 (m, 4H), 2.73 (t, 1H, J=11.4 Hz), 3.08-3.24 (m, 2H), 6.44 (s, 1H), 7.07 (d, 1H, J=7.5 Hz), 7.47 (d, 1H, J=8.4 Hz), 7.85 (d, 1H, J=8.4 Hz), 11.63 (s, 1H).

Compound Ib-5

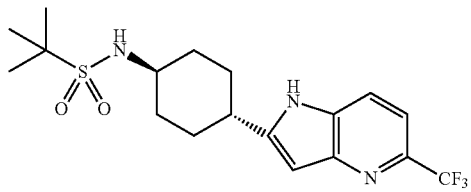

¹H-NMR (DMSO-d₆) δ: 1.29 (s, 9H), 1.38-1.68 (m, 4H), 1.98-2.14 (m, 4H), 2.73 (t, 1H, J=11.4 Hz), 3.08-3.24 (m, 2H), 6.45 (s, 1H), 6.87 (d, 1H, J=8.1 Hz), 7.46 (d, 1H, J=8.4 Hz), 7.84 (d, 1H, J=8.4 Hz), 11.63 (s, 1H).

Compound Ib-6

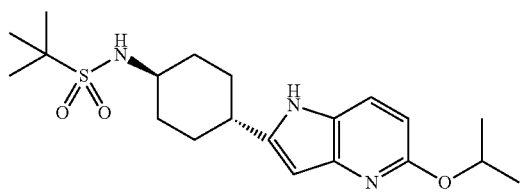

¹H-NMR (DMSO-d₆) δ: 1.26 (d, 6H, J=6.1 Hz), 1.28 (s, 9H), 1.37-1.58 (m, 4H), 1.99-2.02 (m, 4H), 2.56-2.63 (m, 1H), 3.10-3.15 (m, 1H), 5.24 (m, 1H), 6.08 (m, 1H), 6.35 (d, 1H, J=8.5 Hz), 6.85 (d, 1H, J=8.5 Hz), 7.50 (dd, 1H, J=0.6, 8.5 Hz), 10.89 (s, 1H).

Compound Ib-7

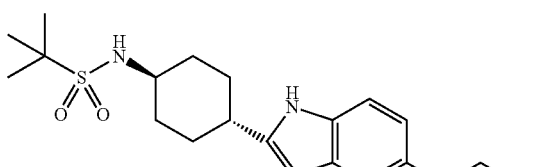

¹H-NMR (CDCl₃) δ: 1.34-1.37 (m, 2H), 1.42 (s, 9H), 1.55-1.69 (m, 2H), 2.13-2.19 (m, 2H), 2.25-2.31 (m, 2H), 2.68 (tt, 1H, J=3.3, 11.7 Hz), 3.29-3.42 (m, 1H), 3.73 (d, 1H, J=9.6 Hz), 4.79 (q, 2H, J=8.7 Hz), 6.26-6.28 (m, 1H), 6.63 (d, 1H, J=8.7 Hz), 7.53 (dd, 1H, J=0.8, 8.7 Hz), 7.97 (s, 1H).

Compound Ib-8

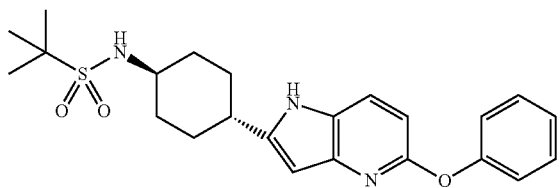

¹H-NMR (DMSO-d₆) δ: 1.20-1.32 (m, 10H), 1.35-1.60 (m, 4H), 1.90-2.10 (m, 4H), 2.63 (t, 1H), 3.12 (m, 1H), 6.10 (s, 1H), 6.68 (d, 1H, J=6.0 Hz), 6.86 (d, 1H, J=6.0 Hz), 6.98-7.04 (m, 2H), 7.11 (t, 1H, J=6.0 Hz), 7.30-7.39 (m, 2H), 7.71 (d, 1H, J=9.0 Hz), 11.16 (s, 1H).

Compound Ib-9

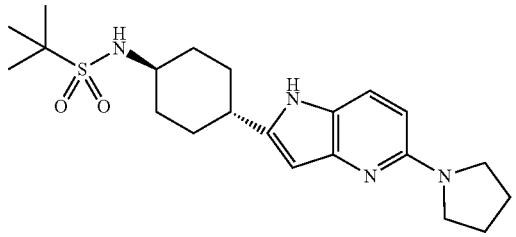

¹H-NMR (DMSO-d₆) δ: 1.28 (s, 9H), 1.35-1.57 (m, 4H), 1.89-1.94 (m, 4H), 1.97-2.03 (m, 4H), 2.52-2.60 (m, 1H), 3.07-3.16 (m, 1H), 3.32-3.37 (m, 4H), 5.95 (m, 1H), 6.19 (d, 1H, J=8.8 Hz), 6.84 (d, 1H, J=8.8 Hz), 7.38 (dd, 1H, J=0.6, 8.8 Hz), 10.51 (s, 1H).

Compound Ib-10

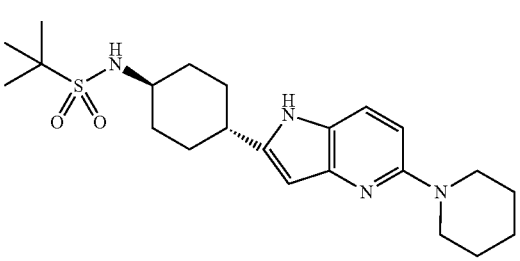

¹H-NMR (CDCl₃) δ: 1.31-1.44 (m, 2H), 1.41 (s, 9H), 1.52-1.72 (m, 8H), 2.09-2.17 (m, 2H), 2.22-2.29 (m, 2H), 2.63 (tt, 1H, J=3.3, 11.9 Hz), 3.26-3.40 (m, 1H), 3.45-3.48 (m, 4H), 3.69 (d, 1H, J=9.5 Hz), 6.22-6.25 (m, 1H), 6.58 (d, 1H, J=8.8 Hz), 7.41 (dd, 1H, J=0.9, 8.8 Hz), 7.76 (s, 1H).

Compound Ib-11

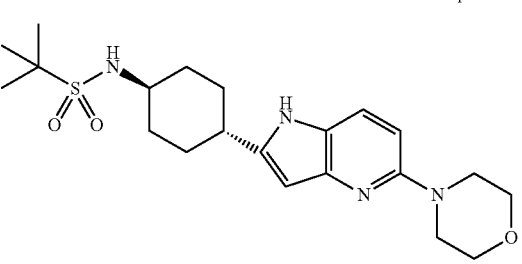

¹H-NMR (DMSO-d₆) δ: 1.28 (s, 9H), 1.36-1.58 (m, 4H), 1.98-2.02 (m, 4H), 2.54-2.62 (m, 1H), 3.08-3.16 (m, 1H), 3.29-3.33 (m, 4H), 3.69-3.72 (m, 4H), 6.01 (m, 1H), 6.58 (d, 1H, J=8.7 Hz), 6.84 (d, 1H, J=8.7 Hz), 7.45 (d, 1H, J=8.7 Hz), 10.71 (s, 1H).

Compound Ib-12

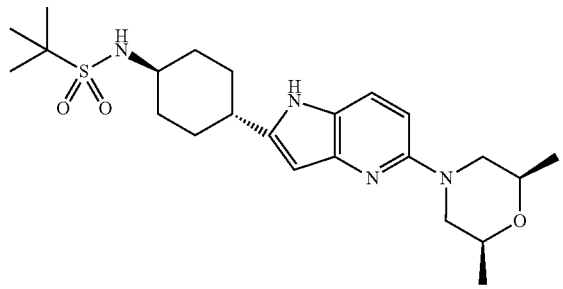

¹H-NMR (DMSO-d₆) δ: 1.16 (d, 6H, J=6.3 Hz), 1.28 (s, 9H), 1.36-1.58 (m, 4H), 1.97-2.04 (m, 4H), 2.27 (dd, 2H, J=10.5, 12.5 Hz), 2.55-2.61 (m, 1H), 3.08-3.17 (m, 1H), 3.64 (ddq, 2H, J=2.3, 10.5, 6.3 Hz), 3.98 (dd, 2H, J=2.3, 12.5 Hz), 6.00-6.01 (m, 1H), 6.58 (d, 1H, J=8.7 Hz), 6.85 (d, 1H, J=8.7 Hz), 7.44 (dd, 1H, J=0.6, 8.7 Hz), 10.69 (m, 1H).

Compound Ib-13

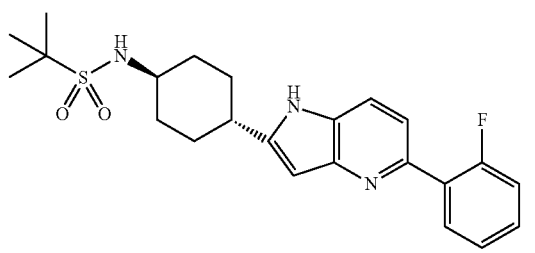

¹H-NMR (DMSO-d₆) δ: 1.29 (s, 9H), 1.43-1.63 (m, 4H), 1.90-2.09 (m, 4H), 2.68-2.73 (m, 1H), 3.15-3.18 (m, 1H), 6.35 (s, 1H), 6.85 (d, 1H, J=8.4 Hz), 7.26-7.32 (m, 1H), 7.39-7.45 (m, 1H), 7.73 (d, 1H, J=8.4 Hz), 7.89-7.93 (m, 1H), 11.26 (s, 1H).

Compound Ib-14

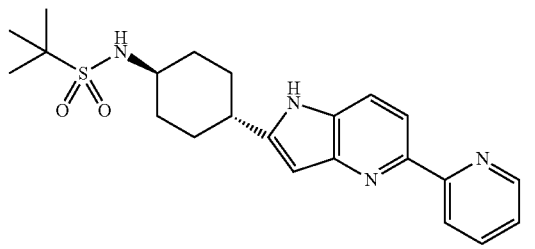

¹H-NMR (DMSO-d₆) δ: 1.29 (s, 9H), 1.44-1.60 (m, 4H), 2.06-2.10 (m, 4H), 2.67-2.69 (m, 1H), 3.18-3.20 (m, 1H), 6.36 (s, 1H), 6.85 (d, 1H, J=8.8 Hz), 7.31-7.38 (m, 1H), 7.74 (d, 1H, J=8.8 Hz), 7.85-7.89 (m, 1H), 8.15 (d, 1H, J=8.0 Hz), 8.41 (d, 1H, J=8.0 Hz), 8.60-8.63 (m, 1H), 11.25 (s, 1H).

Compound Ib-15

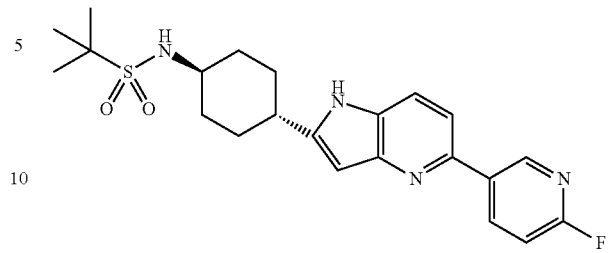

¹H-NMR (DMSO-d₆) δ: 1.29 (s, 9H), 1.43-1.62 (m, 4H), 1.99-2.09 (m, 4H), 2.67-2.72 (m, 1H), 3.15-3.17 (m, 1H), 6.36 (s, 1H), 6.86 (d, 1H, J=8.4 Hz), 7.25 (d, 1H, J=7.6 Hz), 7.66 (d, 1H, J=8.4 Hz), 7.74 (d, 1H, J=8.0 Hz), 8.58-8.63 (m, 1H), 8.87 (s, 1H), 11.26 (s, 1H).

Compound Ib-16

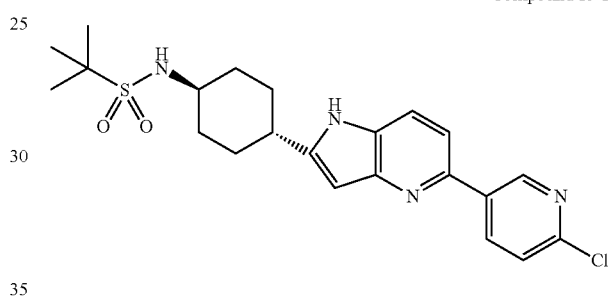

¹H-NMR (DMSO-d₆) δ: 1.29 (s, 9H), 1.38-1.68 (m, 4H), 1.98-2.14 (m, 4H), 2.70 (t, 1H, J=11.4 Hz), 3.08-3.24 (m, 1H), 6.37 (s, 1H), 6.88 (d, 1H, J=8.4 Hz), 7.58 (d, 1H, J=8.4 Hz), 7.69 (d, 1H, J=8.4 Hz), 7.75 (d, 1H, J=8.4 Hz), 8.49 (dd, 1H, J=8.4, 2.4 Hz), 9.07 (d, 1H, J=2.4 Hz), 11.30 (s, 1H).

Compound Ib-17

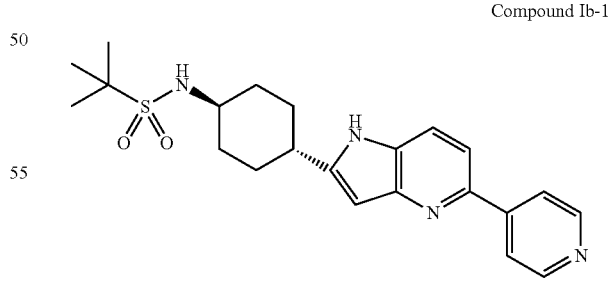

¹H-NMR (DMSO-d₆) δ: 1.29 (s, 9H), 1.46-1.64 (m, 4H), 2.02-2.15 (m, 4H), 2.68-2.74 (m, 1H), 3.15-3.18 (m, 1H), 6.39 (s, 1H), 6.86 (d, 1H, J=9.2 Hz), 7.76 (s, 2H), 8.04-8.06 (m, 2H), 8.59-8.64 (m, 2H), 11.31 (s, 1H).

Compound Ib-18

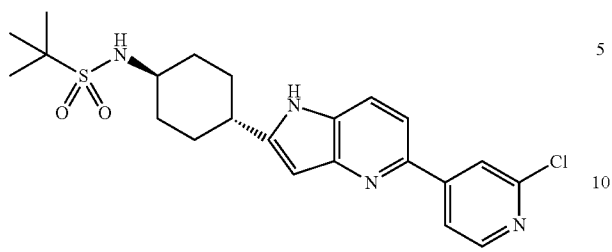

¹H-NMR (DMSO-d₆) δ: 1.29 (s, 9H), 1.40-1.68 (m, 4H), 1.98-2.14 (m, 4H), 2.71 (t, 1H, J=11.4 Hz), 3.08-3.24 (m, 1H), 6.41 (s, 1H), 6.88 (d, 1H, J=8.7 Hz), 7.77 (d, 1H, J=8.4 Hz), 7.84 (d, 1H, J=8.4 Hz), 8.09 (dd, 1H, J=5.4, 1.5 Hz), 8.15 (s, 1H), 8.45 (d, 1H, J=5.4 Hz), 11.40 (s, 1H).

Compound Ib-19

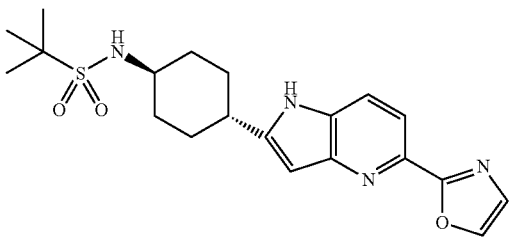

¹H-NMR (DMSO-d₆) δ: 1.29 (s, 9H), 1.46-1.62 (m, 4H), 2.00-2.11 (m, 4H), 2.68-2.71 (m, 1H), 3.14-3.18 (m, 1H), 6.39 (s, 1H), 6.84-6.87 (m, 1H), 7.37 (s, 1H), 7.76-7.84 (m, 2H), 8.20 (s, 1H), 11.44 (s, 1H).

Compound Ib-20

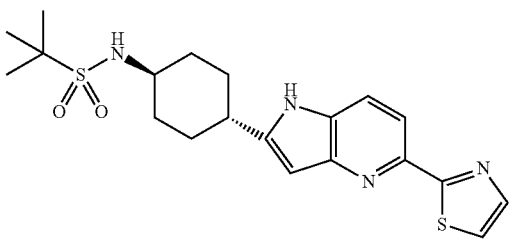

¹H-NMR (DMSO-d₆) δ: 1.27 (s, 9H), 1.43-1.54 (m, 4H), 2.00-2.11 (m, 4H), 2.60-2.70 (m, 1H), 3.10-3.30 (m, 1H), 6.35 (s, 1H), 6.85-6.87 (m, 2H), 7.68-7.74 (m, 1H), 7.84-7.86 (m, 2H), 11.39 (s, 1H).

Compound Ib-21

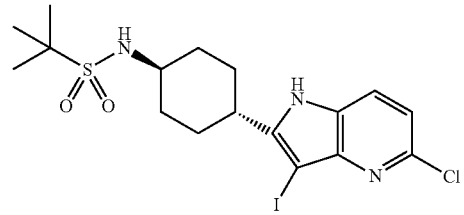

¹H-NMR (DMSO-d₆) δ: 1.29 (s, 9H), 1.42-1.51 (m, 2H), 1.67-87 (m, 4H), 2.02-2.05 (m, 2H), 2.82-2.84 (m, 1H), 3.16-3.20 (m, 1H), 6.88-6.93 (m, 1H), 7.13-7.15 (m, 1H), 7.72-7.74 (m, 1H), 11.86 (s, 1H).

Compound Ib-22

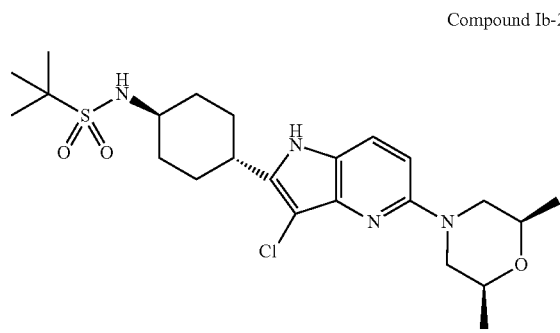

¹H-NMR (DMSO-d₆) δ: 1.17 (d, 6H, J=6.3 Hz), 1.29 (s, 9H), 1.40-1.50 (m, 2H), 1.63-1.75 (m, 2H), 1.81-1.85 (m, 2H), 1.98-2.03 (m, 2H), 2.32 (dd, 2H, J=10.5, 12.5 Hz), 2.78-2.86 (m, 1H), 3.10-3.19 (m, 1H), 3.60-3.70 (m, 2H), 4.04-4.10 (m, 2H), 6.70 (d, 1H, J=8.8 Hz), 6.90 (d, 1H, J=8.5 Hz), 7.51 (d, 1H, J=8.8 Hz), 11.02 (s, 1H).

Compound Ib-23

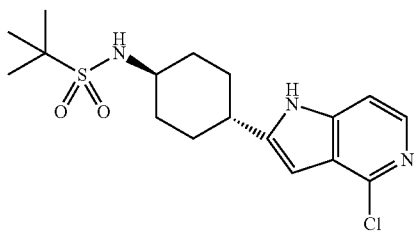

¹H-NMR (DMSO-d₆) δ: 1.28 (s, 9H), 1.38-1.62 (m, 4H), 1.99-2.07 (m, 4H), 2.63-2.73 (m, 1H), 3.09-3.18 (m, 1H), 6.23 (s, 1H), 6.85 (d, 1H, J=8.5 Hz), 7.29 (d, 1H, J=5.5 Hz), 7.87 (d, 1H, J=5.5 Hz), 11.74 (s, 1H).

Compound Ib-24

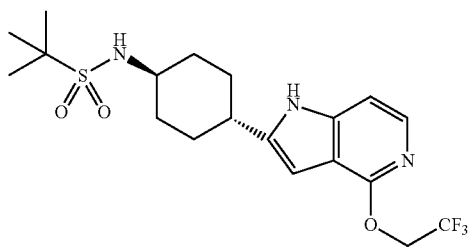

¹H-NMR (CDCl₃) δ: 1.34-1.47 (m, 2H), 1.42 (s, 9H), 1.55-1.69 (m, 2H), 2.13-2.20 (m, 2H), 2.25-2.32 (m, 2H), 2.67 (tt, 1H, J=3.2, 12.0 Hz), 3.28-3.42 (m, 1H), 3.45-3.48 (m, 4H), 3.69 (d, 1H, J=9.5 Hz), 4.89 (q, 2H, J=8.7 Hz), 6.34-6.37 (m, 1H), 6.95 (dd, 1H, J=0.8, 5.8 Hz), 7.74 (d, 1H, J=5.8 Hz), 8.19 (s, 1H).

Compound Ib-25

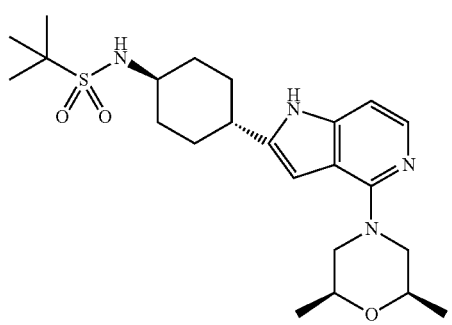

¹H-NMR (DMSO-d₆) δ: 1.15 (d, 6H, J=6.3 Hz), 1.28 (s, 9H), 1.36-1.61 (m, 4H), 1.97-2.04 (m, 4H), 2.55-2.64 (m, 1H), 3.08-3.18 (m, 1H), 3.65-3.76 (m, 2H), 4.02-4.09 (m, 2H), 6.23 (m, 1H), 6.76 (dd, 1H, J=0.6, 5.5 Hz), 6.84 (d, 1H, J=8.7 Hz), 7.64 (d, 1H, J=5.5 Hz), 11.15 (m, 1H).

Compound Ib-26

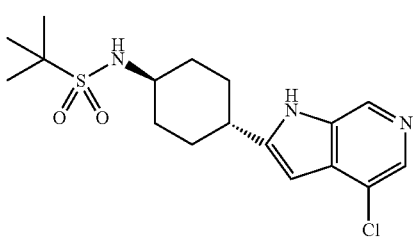

¹H-NMR (DMSO-d₆) δ: 1.28 (s, 9H), 1.41-1.62 (m, 4H), 1.98-2.12 (m, 4H), 2.70-2.75 (m, 1H), 3.14-3.15 (m, 1H), 6.34 (s, 1H), 6.85 (d, 1H, J=8.4 Hz), 8.06 (brs, 1H), 8.57 (brs, 1H), 11.81 (s, 1H).

Compound Ib-27

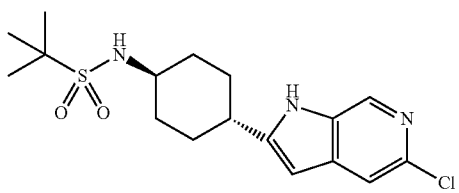

¹H-NMR (DMSO-d₆) δ: 1.27 (s, 9H), 1.43-1.58 (m, 4H), 1.95-2.08 (m, 4H), 2.65-2.73 (m, 1H), 3.10-3.20 (m, 1H), 6.20 (s, 1H), 6.85 (d, 1H, J=8.4 Hz), 7.44 (s, 1H), 8.39 (s, 1H), 11.62 (s, 1H).

Compound Ib-28

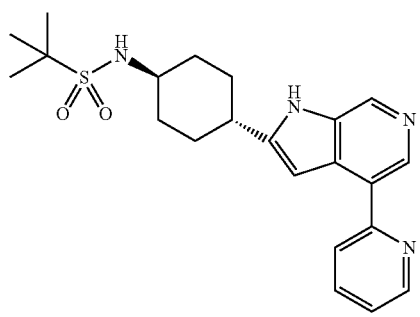

¹H-NMR (DMSO-d₆) δ: 1.29 (s, 9H), 1.45-1.66 (m, 4H), 2.01-2.09 (m, 4H), 2.67-2.78 (m, 1H), 3.14-3.22 (m, 1H), 6.76 (s, 1H), 6.86 (d, 1H, J=8.8 Hz), 7.36-7.39 (m, 1H), 7.89-7.97 (m, 2H), 8.57 (s, 1H), 8.66 (s, 1H), 8.73-8.74 (m, 1H), 11.66 (s, 1H).

Compound Ib-29

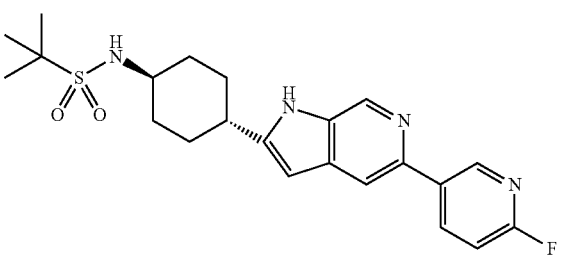

¹H-NMR (DMSO-d₆) δ: 1.29 (s, 9H), 1.43-1.63 (m, 4H), 2.02-2.09 (m, 4H), 2.69-2.75 (m, 1H), 3.10-3.22 (m, 1H), 6.30 (s, 1H), 6.87 (d, 1H, J=8.4 Hz), 7.22-7.25 (m, 1H), 8.06 (s, 1H), 8.57-8.61 (m, 1H), 8.72 (s, 1H), 8.88 (s, 1H), 11.54 (s, 1H).

Compound Ib-30

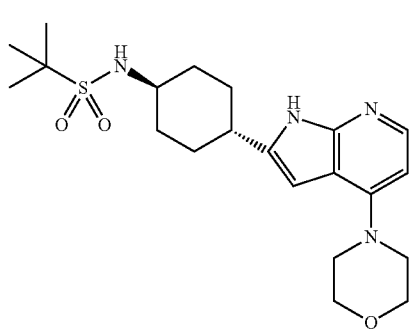

¹H-NMR (DMSO-d₆) δ: 1.28 (s, 9H), 1.36-1.64 (m, 4H), 1.96-2.08 (m, 4H), 2.57 (t, 1H, J=11.4 Hz), 3.05-3.20 (m, 1H), 3.24-3.36 (m, 4H), 3.76-3.84 (m, 4H), 6.17 (s, 1H), 6.38 (d, 1H, J=5.4 Hz), 6.85 (d, 1H, J=8.4 Hz), 7.88 (d, 1H, J=5.1 Hz), 11.25 (s, 1H).

Compound Ib-31

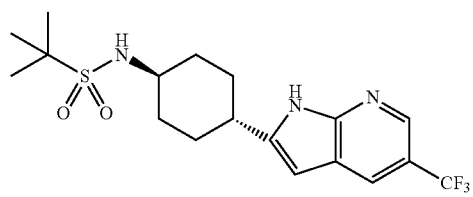

¹H-NMR (DMSO-d₆) δ: 1.29 (s, 9H), 1.36-1.64 (m, 4H), 1.96-2.12 (m, 4H), 2.69 (t, 1H, J=11.4 Hz), 3.06-3.24 (m, 1H), 6.32 (s, 1H), 6.86 (d, 1H, J=9.0 Hz), 8.21 (d, 1H, J=2.1 Hz), 8.44 (d, 1H, J=2.1 Hz), 11.98 (s, 1H).

Compound Ib-32

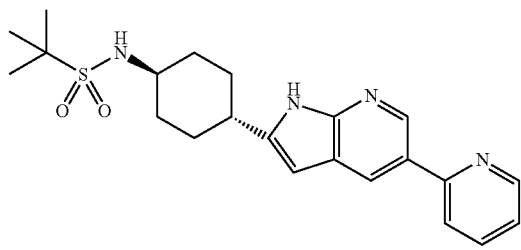

¹H-NMR (DMSO-d₆) δ: 1.29 (s, 9H), 1.38-1.68 (m, 4H), 1.96-2.14 (m, 4H), 2.66 (t, 1H, J=11.4 Hz), 3.06-3.24 (m, 1H), 6.23 (s, 1H), 6.87 (d, 1H, J=8.1 Hz), 7.31 (dd, 1H, J=7.5, 4.5 Hz), 7.85 (t, 1H, J=8.4 Hz), 7.99 (d, 1H, J=7.8 Hz), 8.47 (d, 1H, J=1.8 Hz), 8.65 (d, 1H, J=4.5 Hz), 8.85 (d, 1H, J=1.8 Hz), 11.59 (s, 1H).

Compound Ib-33

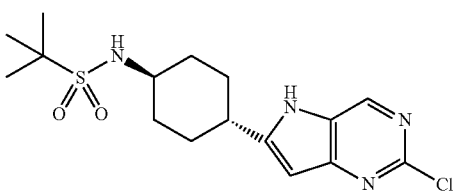

¹H-NMR (DMSO-d₆) δ: 1.29 (s, 9H), 1.41-1.64 (m, 4H), 1.99-2.09 (m, 4H), 2.67-2.79 (m, 1H), 3.12-3.18 (m, 1H), 6.37 (s, 1H), 6.86 (d, 1H, J=8.4 Hz), 8.65 (s, 1H), 11.94 (s, 1H).

Compound Ib-34

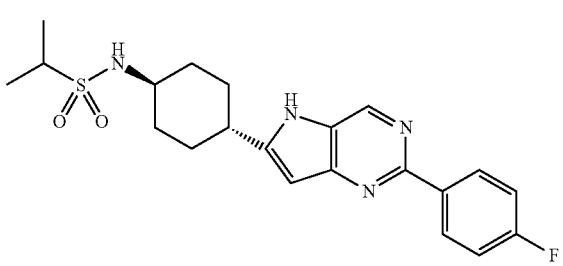

¹H-NMR (DMSO-d₆) δ: 1.25 (d, 6H, J=6.4 Hz), 1.37-1.51 (m, 2H), 1.52-1.68 (m, 2H), 1.97-2.12 (m, 4H), 2.75 (m, 1H), 3.10-3.21 (m, 2H), 6.40 (s, 1H), 7.05 (d, 1H, J=8.4 Hz), 7.28 (t, 2H, J=8.4 Hz), 8.40-8.49 (m, 2H), 8.83 (s, 1H), 11.7 (s, 1H).

Compound Ib-35

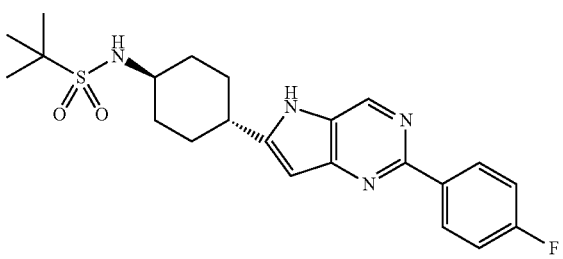

¹H-NMR (DMSO-d₆) δ: 1.30 (s, 9H), 1.47-1.66 (m, 4H), 2.00-2.10 (m, 4H), 2.73-2.79 (m, 1H), 3.17-3.18 (m, 1H), 6.42 (s, 1H), 6.89 (d, 1H, J=8.0 Hz), 7.27-7.31 (m, 2H), 8.44-8.50 (m, 2H), 8.84 (s, 1H), 11.72 (s, 1H).

Compound Ib-36

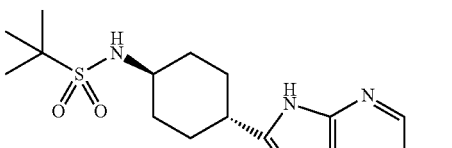

¹H-NMR (DMSO-d₆) δ: 1.28 (s, 9H), 1.44-1.64 (m, 4H), 2.00-2.10 (m, 4H), 2.69-2.75 (m, 1H), 3.14-3.16 (m, 1H), 6.37 (s, 1H), 6.82-6.86 (m, 1H), 8.22 (s, 1H), 12.14 (s, 1H).

Compound Ib-37

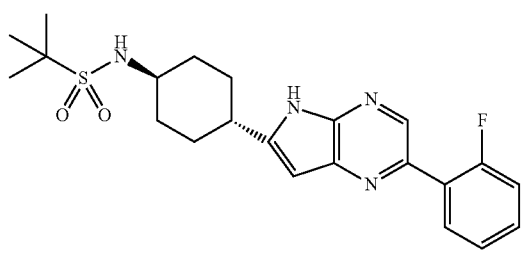

¹H-NMR (DMSO-d₆) δ: 1.29 (s, 9H), 1.43-1.67 (m, 4H), 2.02-2.10 (m, 4H), 2.71-2.77 (m, 1H), 3.10-3.22 (m, 1H), 6.43 (s, 1H), 6.87 (d, 1H, J=8.8 Hz), 7.32-7.40 (m, 2H), 7.45-7.54 (m, 1H), 7.91 (t, 1H, J=7.6 Hz), 8.51 (d, 1H, J=2.4 Hz), 11.97 (s, 1H).

Compound Ib-38

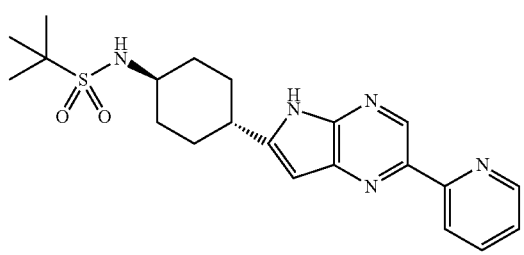

¹H-NMR (DMSO-d₆) δ: 1.29 (s, 9H), 1.46-1.68 (m, 4H), 2.03-2.10 (m, 4H), 2.68-2.73 (m, 1H), 3.10-3.20 (m, 1H), 6.44 (s, 1H), 6.86-6.88 (m, 1H), 7.41-7.43 (m, 1H), 8.35-8.37 (m, 1H), 8.65-8.70 (m, 1H), 9.14 (s, 1H), 11.97 (s, 1H).

Compound IIa-1

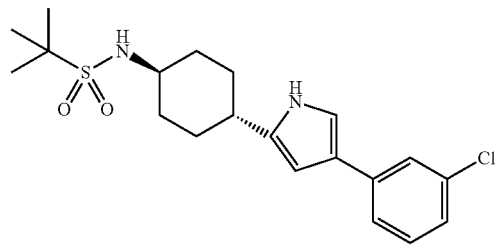

¹H-NMR (DMSO-d₆) δ: 1.28 (s, 9H), 1.37-1.47 (m, 4H), 1.91-2.01 (m, 4H), 2.42 (m, 1H), 3.09 (m, 1H), 6.16 (s, 1H), 6.80 (d, 1H, J=9.2 Hz), 7.14 (s, 1H), 7.27 (dd, 1H, J=8.4, 7.6 Hz), 7.42 (d, 1H, J=7.6 Hz), 7.50 (s, 1H), 10.7 (s, 1H).

Compound IIa-2

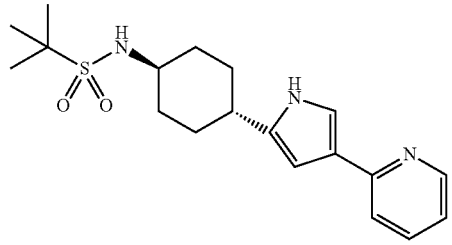

¹H-NMR (DMSO-d₆) δ: 1.28 (s, 9H), 1.37-1.49 (m, 4H), 1.93-2.04 (m, 4H), 2.45 (m, 1H), 3.10 (m, 1H), 6.29 (s, 1H), 6.80 (d, 1H, J=8.0 Hz), 7.01 (m, 1H), 7.25 (s, 1H), 7.49 (d, 1H, J=7.2 Hz), 7.62 (dd, 1H, J=8.4, 7.2 Hz), 8.39 (d, 1H, J=4.0 Hz), 10.8 (s, 1H).

Compound IIa-3

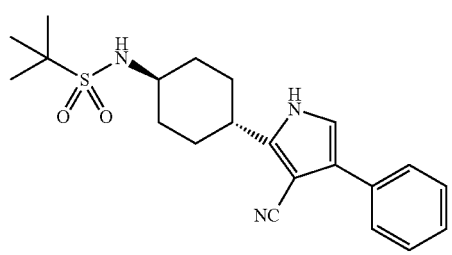

¹H-NMR (DMSO-d₆) δ: 1.29 (s, 9H), 1.37-1.52 (m, 2H), 1.60-1.75 (m, 2H), 1.83-1.92 (m, 2H), 1.97-2.05 (m, 2H), 2.71 (m, 1H), 3.12 (m, 1H), 6.89 (d, 1H, J=8.8 Hz), 7.14 (s, 1H), 7.25 (t, 1H, J=7.6 Hz), 7.39 (dd, 1H, J=7.6, 7.6 Hz), 7.60 (d, 2H, J=7.6 Hz), 11.7 (s, 1H).

Compound IIa-4

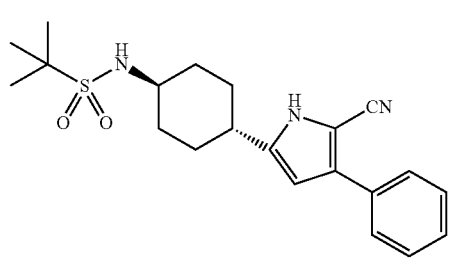

¹H-NMR (DMSO-d₆) δ: 1.28 (s, 9H), 1.33-1.54 (m, 4H), 1.92-2.02 (m, 4H), 2.51 (m, 1H), 3.12 (m, 1H), 6.34 (s, 1H), 6.83 (d, 1H, J=8.8 Hz), 7.31 (t, 1H, J=7.6 Hz), 7.43 (dd, 1H, J=7.6, 7.6 Hz), 7.63 (d, 2H, J=7.6 Hz), 12.1 (s, 1H).

Compound IIa-5

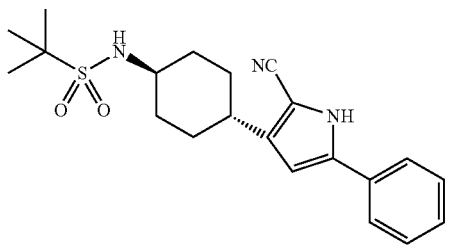

¹H-NMR (DMSO-d₆) δ: 1.29 (s, 9H), 1.37-1.49 (m, 2H), 1.49-1.61 (m, 2H), 1.82-1.91 (m, 2H), 1.95-2.03 (m, 2H), 2.47 (m, 1H), 3.14 (m, 1H), 6.65 (s, 1H), 6.86 (d, 1H, J=8.4 Hz), 7.29 (t, 1H, J=7.6 Hz), 7.42 (dd, 1H, J=7.6, 7.6 Hz), 7.69 (d, 2H, J=7.6 Hz), 12.3 (s, 1H).

Compound IIa-6

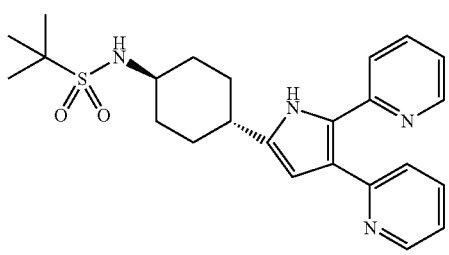

¹H-NMR (DMSO-d₆) δ: 1.28 (s, 9H), 1.34-1.49 (m, 4H), 1.93-2.04 (m, 4H), 2.58 (m, 1H), 3.15 (m, 1H), 6.18 (s, 1H), 6.80 (d, 1H, J=8.8 Hz), 7.11-7.26 (m, 2H), 7.43 (m, 1H), 7.51 (m, 1H), 7.62 (m, 1H), 7.72 (m, 1H), 8.48-8.58 (m, 2H), 11.2 (s, 1H).

Compound IIa-7

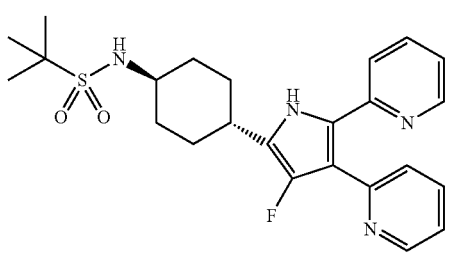

Compound IIIa-1

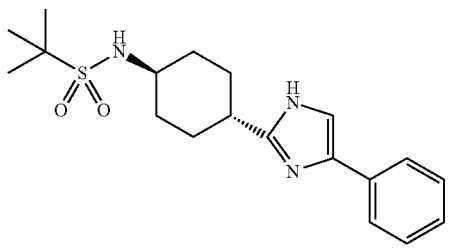

¹H-NMR (DMSO-d₆) δ: 1.28 (s, 9H), 1.35-1.61 (m, 4H), 1.97-2.00 (m, 4H), 2.54-2.62 (m, 1H), 3.09-3.12 (m, 1H), 6.84 (d, 1H, J=8.4 Hz), 7.18 (t, 1H, J=8.4 Hz), 7.32 (t, 1H, J=8.4 Hz), 7.44 (s, 1H), 7.71 (d, 2H, J=7.8 Hz), 11.71 (s, 1H).

Compound IIIa-2

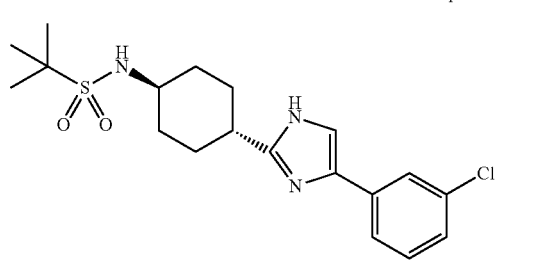

¹H-NMR (DMSO-d₆) δ: 1.31 (s, 9H), 1.37-1.63 (m, 4H), 2.00-2.03 (m, 4H), 2.57-2.65 (m, 1H), 3.07-3.20 (m, 1H), 6.85 (d, 1H, J=8.4 Hz), 7.38-7.18 (m, 2H), 7.61-7.79 (m, 3H), 11.85 (s, 1H).

Compound IIIa-3

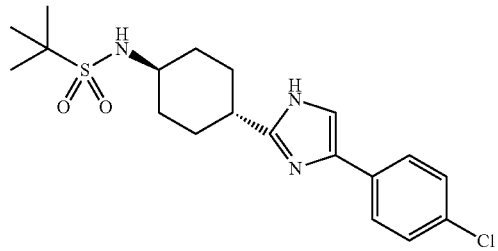

¹H-NMR (DMSO-d₆) δ: 1.30 (s, 9H), 1.37-1.60 (m, 4H), 1.99-2.03 (m, 4H), 2.56-2.64 (m, 1H), 3.10-3.16 (m, 1H), 6.86 (d, 1H, J=8.6 Hz), 7.37-7.77 (m, 5H), 11.81 (s, 1H).

Compound IIIa-4

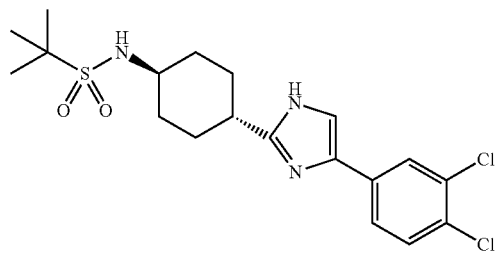

¹H-NMR (DMSO-d₆) δ: 1.27 (s, 9H), 1.30-1.62 (m, 4H), 1.90-2.04 (m, 4H), 2.57 (t, 1H, J=11.4 Hz), 3.03-3.18 (m, 1H), 6.82 (d, 1H, J=8.7 Hz), 7.53 (d, 1H, J=8.4 Hz), 7.60-7.72 (m, 2H), 7.91 (s, 1H), 11.87 (s, 1H).

Compound IIIa-5
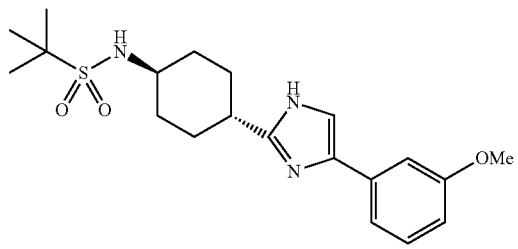
¹H-NMR (DMSO-d₆) δ: 1.30 (s, 9H), 1.37-1.64 (m, 4H), 1.99-2.03 (m, 4H), 2.56-2.65 (m, 1H), 3.09-3.20 (m, 1H), 3.80 (s, 3H), 6.72-6.88 (m, 2H), 7.20-7.33 (m, 3H), 7.50 (d, 1H, J=1.9 Hz), 11.76 (1H, s).
Compound IIIa-8
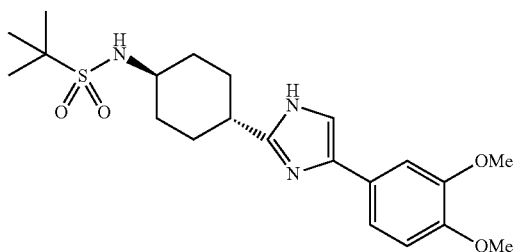
¹H-NMR (DMSO-d₆) δ: 1.28 (s, 9H), 1.35-1.62 (m, 4H), 1.97-1.99 (m, 4H), 2.51-2.62 (m, 1H), 3.11-3.14 (m, 1H), 3.74 (s, 3H), 3.79 (s, 3H), 6.83-7.86 (m, 5H), 11.65 (s, 1H).
Compound IIIa-6
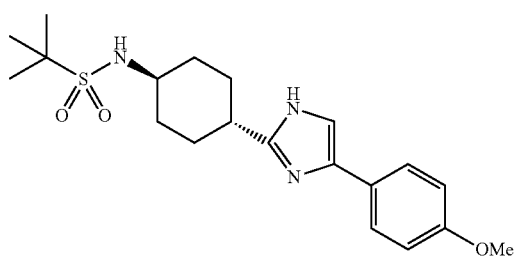
¹H-NMR (DMSO-d₆) δ: 1.38 (s, 9H), 1.41-1.63 (m, 4H), 1.98-2.03 (m, 4H), 2.57-2.63 (m, 1H), 3.11-3.16 (m, 1H), 3.77 (s, 3H), 6.85-7.05 (m, 3H), 7.34 (d, 1H, J=1.5 Hz), 7.64-7.67 (m, 2H), 11.64 (s, 1H).
Compound IIIa-9
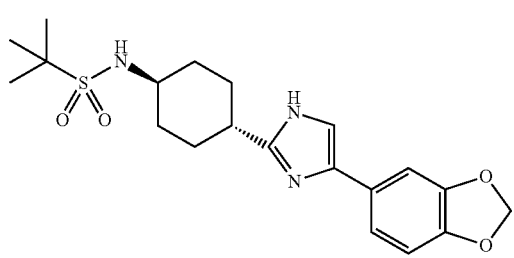
¹H-NMR (DMSO-d₆) δ: 1.28 (s, 9H), 1.35-1.61 (m, 4H), 1.97-1.99 (m, 4H), 2.50-2.61 (m, 1H), 3.10-3.13 (m, 1H), 5.99 (s, 2H), 6.83-6.88 (m, 2H), 7.25-7.66 (m, 3H), 11.66 (s, 1H).
Compound IIIa-7
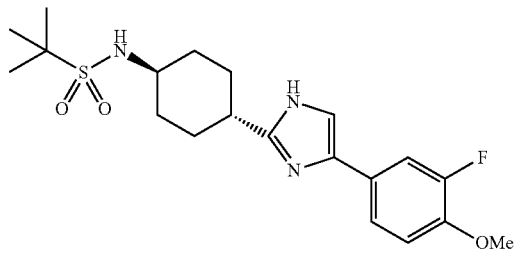
¹H-NMR (DMSO-d₆) δ: 1.30 (s, 9H), 1.37-1.62 (m, 4H), 1.99-2.03 (m, 4H), 2.52-2.63 (m, 1H), 3.12-3.15 (m, 1H), 3.85 (s, 3H), 6.87 (d, 1H, J=9.0 Hz), 7.10-7.16 (m, 1H), 7.45-7.55 (m, 3H), 11.73 (s, 1H).
Compound IIIa-10
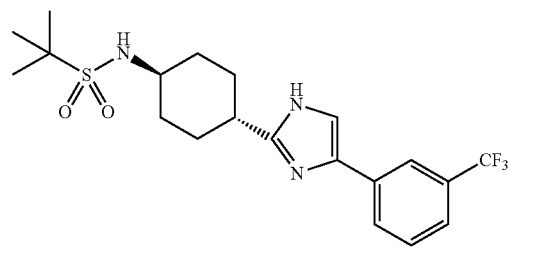
¹H-NMR (CDCl3) δ: 1.41 (s, 9H), 1.58-1.78 (m, 4H), 2.15-2.32 (m, 4H), 2.70-2.84 (m, 1H), 3.28-3.45 (m, 1H), 3.80 (d, 1H, J=9.3 Hz), 7.42-7.50 (m, 2H), 7.84-7.98 (m, 2H), 9.18 (brs, 1H).

Compound IIIa-11

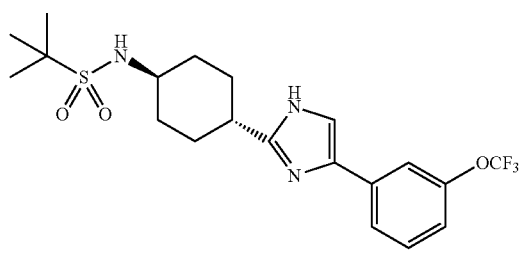

¹H-NMR (DMSO-d₆) δ: 1.30 (s, 9H), 1.35-1.67 (m, 4H), 1.92-2.05 (m, 4H), 2.64-2.76 (m, 1H), 3.07-3.18 (m, 1H), 6.83-6.89 (m, 1H), 7.21-7.23 (m, 1H), 7.49-7.80 (m, 4H), 11.66 (s, 1H).

Compound IIIa-14

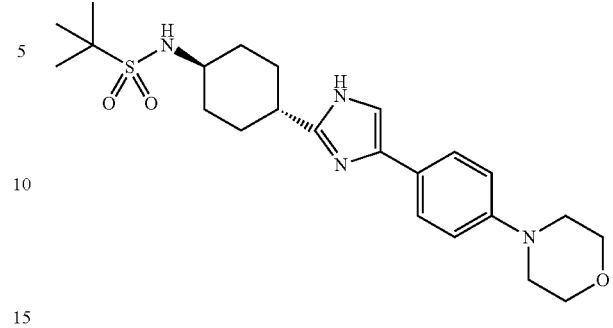

¹H-NMR (DMSO-d₆) δ: 1.31 (s, 9H), 1.37-1.64 (m, 4H), 1.94-2.01 (m, 4H), 2.54-2.76 (m, 1H), 3.10-3.13 (m, 5H), 3.74-3.77 (m, 5H), 6.86 (d, 1H, J=9.0 Hz), 6.94 (d, 2H, J=8.0 Hz), 7.24 (s, 1H), 7.57 (d, 2H, J=8.0 Hz), 11.64 (s, 1H).

Compound IIIa-12

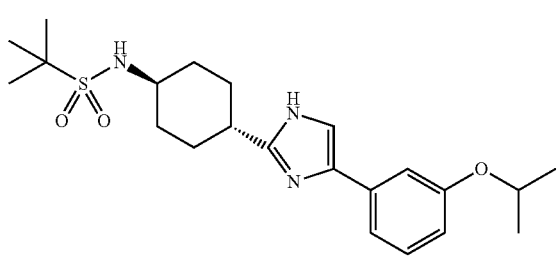

¹H-NMR (DMSO-d₆) δ: 1.31 (s, 9H), 1.37-1.60 (m, 10H), 2.00-2.03 (m, 4H), 2.57-2.64 (m, 1H), 3.08-3.20 (m, 1H), 4.58-4.72 (m, 1H), 6.58-7.65 (m, 6H), 11.74 (s, 1H).

Compound IIIa-15

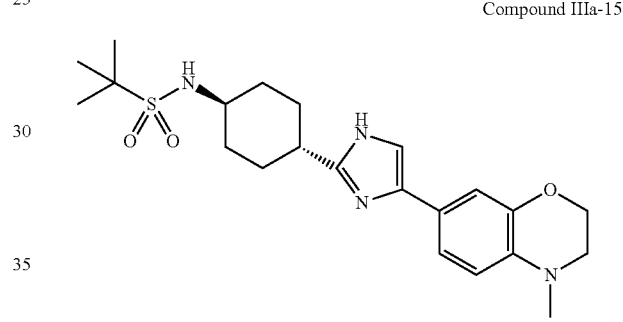

¹H-NMR (DMSO-d₆) δ: 1.31 (s, 9H), 1.37-1.50 (m, 2H), 1.65-1.81 (m, 2H), 2.02-2.09 (m, 4H), 2.52-2.53 (m, 1H), 2.91 (s, 3H), 3.09-3.18 (m, 1H), 3.31-3.35 (m, 2H), 4.26-4.30 (m, 2H), 6.81 (d, 1H, J=9.0 Hz), 6.93 (d, 1H, J=8.0 Hz), 7.19 (s, 1H), 7.27 (d, 1H, J=8.0 Hz), 7.84 (s, 1H), 14.09 (s, 1H).

Compound IIIa-13

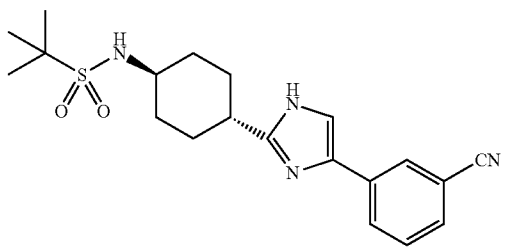

¹H-NMR (DMSO-d₆) δ: 1.31 (s, 9H), 1.38-1.65 (m, 4H), 2.02-2.04 (m, 4H), 2.59-2.67 (m, 1H), 3.10-3.20 (m, 1H), 6.88 (d, 1H, J=9.0 Hz), 7.53-7.70 (m, 3H), 8.06-8.15 (m, 2H), 11.95 (s, 1H).

Compound IIIa-16

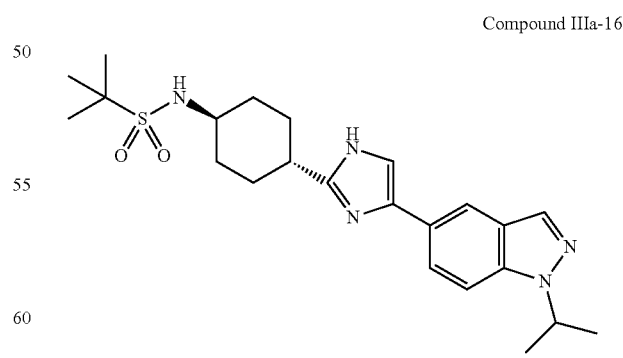

¹H-NMR (DMSO-d₆) δ: 1.31 (s, 9H), 1.38-1.670 (m, 10H), 2.01-2.06 (m, 4H), 2.59-2.67 (m, 1H), 3.14-3.17 (m, 1H), 4.93-5.02 (m, 1H), 6.88 (d, 1H, J=9.0 Hz), 7.46-7.81 (m, 3H), 7.98-8.08 (m, 2H), 11.70 (s, 1H).

Compound IIIa-17

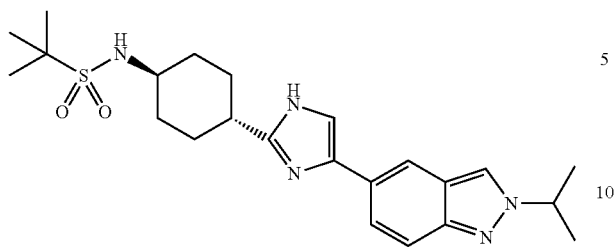

¹H-NMR (DMSO-d₆) δ: 1.31 (s, 9H), 1.39-1.68 (m, 10H), 2.01-2.06 (m, 4H), 2.59-2.67 (m, 1H), 3.15-3.18 (m, 1H), 4.77-4.85 (m, 1H), 6.88 (d, 1H, J=9.0 Hz), 7.39-7.65 (m, 3H), 7.99 (s, 1H), 8.35 (s, 1H), 11.71 (s, 1H).

Compound IIIa-18

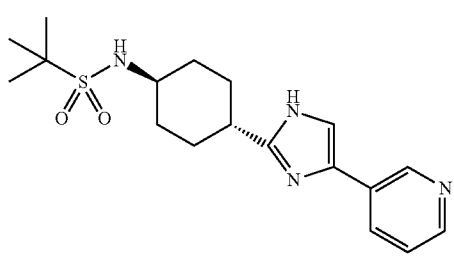

¹H-NMR (DMSO-d₆) δ: 1.30 (s, 9H), 1.37-1.64 (m, 4H), 2.01-2.05 (m, 4H), 2.59-2.67 (m, 1H), 3.08-3.19 (m, 1H), 6.87 (d, 1H, J=9.0 Hz), 7.33-7.37 (m, 1H), 7.64-7.65 (m, 1H), 8.05-8.08 (m, 1H), 8.36-8.38 (m, 1H), 8.95-8.96 (m, 1H), 11.90 (s, 1H).

Compound IIIa-19

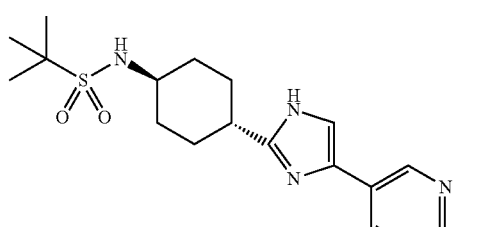

¹H-NMR (DMSO-d₆) δ: 1.30 (s, 9H), 1.37-1.63 (m, 4H), 2.00-2.03 (m, 4H), 2.59-2.66 (m, 1H), 3.12-3.15 (m, 1H), 6.87 (d, 1H, J=9.0 Hz), 7.14-7.18 (m, 1H), 7.63-7.65 (m, 1H), 8.22-8.29 (m, 1H), 8.57-8.58 (m, 1H), 11.91 (s, 1H).

Compound IIIb-1

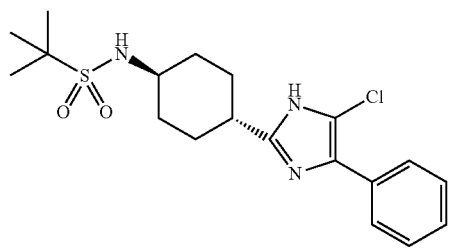

¹H-NMR (DMSO-d₆) δ: 1.28 (s, 9H), 1.36-1.64 (m, 4H), 1.90-2.04 (m, 4H), 2.57 (t, 1H, J=11.4 Hz), 3.05-3.18 (m, 1H), 6.82 (d, 1H, J=6.6 Hz), 7.27-7.35 (m, 1H), 7.42-7.50 (m, 2H), 7.68 (d, 2H, J=5.7 Hz), 12.25 (s, 1H).

Compound IIIb-2

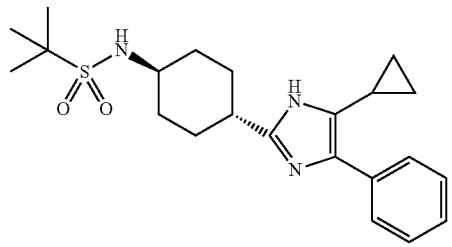

¹H-NMR (DMSO-d₆) δ: 1.21-1.67 (m, 10H), 1.31 (s, 9H), 1.93-2.02 (m, 4H), 2.53-2.61 (m, 1H), 3.05-3.36 (m, 2H), 6.85 (d, 1H, J=9.0 Hz), 7.20-7.53 (m, 5H), 11.38 (s, 1H×7/10), 11.50 (s, 1H×3/10).

Compound IIIb-3

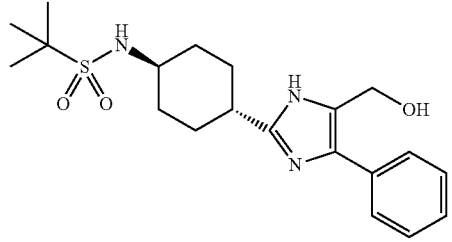

¹H-NMR (DMSO-d₆) δ: 1.20-1.65 (m, 8H), 1.30 (s, 9H), 1.90-2.00 (m, 4H), 2.52-2.60 (m, 1H), 2.99-3.17 (m, 2H), 6.60-7.71 (m, 6H), 12.09 (s, 1H).

Compound IIIb-4

¹H-NMR (DMSO-d₆) δ: 1.28 (s, 9H), 1.36-1.64 (m, 4H), 1.92-2.04 (m, 4H), 2.57 (t, 1H, J=11.4 Hz), 3.05-3.18 (m, 1H), 4.50 (s, 2H), 5.16 (brs, 1H), 6.82 (d, 1H, J=6.3 Hz), 7.16-7.26 (m, 1H), 7.32-7.42 (m, 2H), 7.60-7.68 (m, 2H), 11.75 (s, 1H).

Compound IIIb-8

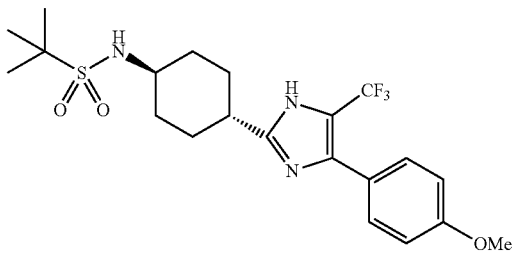

Compound IIIb-5

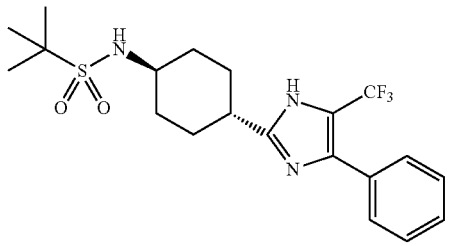

¹H-NMR (DMSO-d₆) δ: 1.28 (s, 9H), 1.32-1.48 (m, 2H), 1.51-1.65 (m, 2H), 1.96-2.03 (m, 4H), 2.60 (m, 1H), 3.13 (m, 1H), 3.80 (s, 3H), 6.83 (d, 1H, J=8.4 Hz), 7.04 (d, 2H, J=8.4 Hz), 7.39 (d, 2H, J=8.4 Hz), 12.4 (s, 1H).

¹H-NMR (DMSO-d₆) δ: 1.28 (s, 9H), 1.32-1.68 (m, 4H), 1.94-2.06 (m, 4H), 2.62 (t, 1H, J=11.4 Hz), 3.05-3.20 (m, 1H), 6.82 (d, 1H, J=8.7 Hz), 7.38-7.58 (m, 5H), 12.53 (s, 1H).

Compound IIIb-9

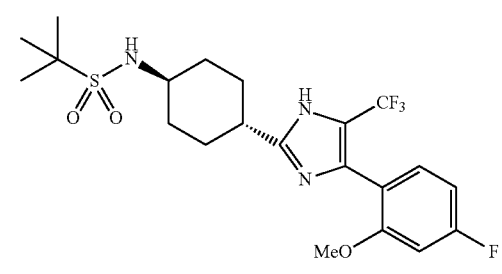

Compound IIIb-6

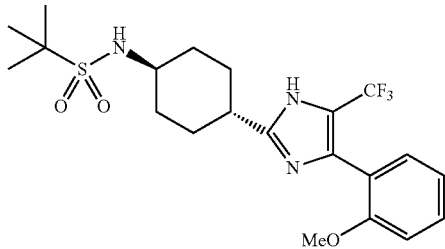

¹H-NMR (DMSO-d₆) δ: 1.28 (s, 9H), 1.32-1.47 (m, 2H), 1.49-1.61 (m, 2H), 1.94-2.04 (m, 4H), 2.59 (m, 1H), 3.12 (m, 1H), 3.77 (s, 3H), 6.83 (d, 1H, J=8.8 Hz), 6.86 (ddd, 1H, J=8.4, 8.4, 2.4 Hz), 7.05 (dd, 1H, J=11.2, 2.4 Hz), 7.28 (dd, 1H, J=8.4, 8.4 Hz), 12.3 (s, 1H).

¹H-NMR (DMSO-d₆) δ: 1.28 (s, 9H), 1.32-1.48 (m, 2H), 1.50-1.62 (m, 2H), 1.95-2.05 (m, 4H), 2.60 (m, 1H), 3.13 (m, 1H), 3.75 (s, 3H), 6.82 (d, 1H, J=8.4 Hz), 7.02 (dd, 1H, J=8.4, 7.2 Hz), 7.12 (d, 1H, J=8.4 Hz), 7.12 (d, 1H, J=7.6 Hz), 7.65 (dd, 1H, J=7.6, 7.2 Hz), 12.3 (s, 1H).

Compound IIIb-10

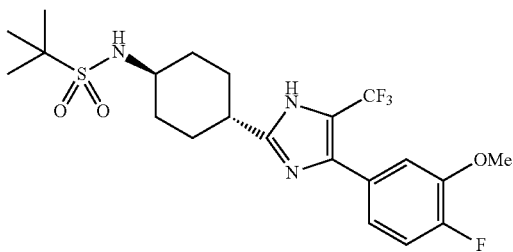

Compound IIIb-7

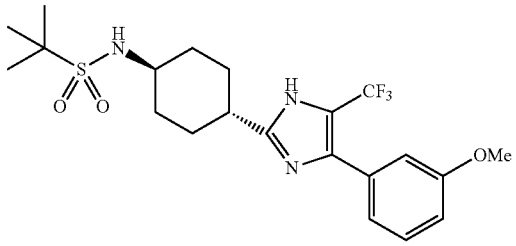

¹H-NMR (DMSO-d₆) δ: 1.28 (s, 9H), 1.34-1.48 (m, 2H), 1.52-1.66 (m, 2H), 1.95-2.06 (m, 4H), 2.62 (m, 1H), 3.13 (m, 1H), 3.80 (s, 3H), 6.83 (d, 1H, J=8.4 Hz), 6.98-7.08 (m, 3H), 7.40 (dd, 1H, J=8.0, 8.0 Hz), 12.5 (s, 1H).

¹H-NMR (DMSO-d₆) δ: 1.28 (s, 9H), 1.33-1.48 (m, 2H), 1.52-1.65 (m, 2H), 1.96-2.05 (m, 4H), 2.62 (m, 1H), 3.13 (m, 1H), 3.88 (s, 3H), 6.83 (d, 1H, J=8.8 Hz), 7.03 (m, 1H), 7.23 (d, 1H, J=6.8 Hz), 7.33 (dd, 1H, J=9.2, 8.4 Hz), 12.5 (s, 1H).

Compound IIIb-11

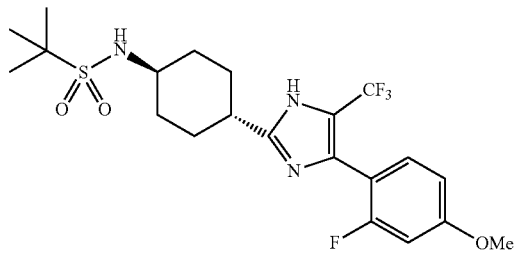

¹H-NMR (DMSO-d₆) δ: 1.28 (s, 9H), 1.37-1.48 (m, 2H), 1.50-1.62 (m, 2H), 1.94-2.06 (m, 4H), 2.61 (m, 1H), 3.12 (m, 1H), 3.82 (s, 3H), 6.83 (d, 1H, J=8.0 Hz), 6.90 (d, 1H, J=6.8 Hz), 6.98 (d, 1H, J=12.4 Hz), 7.34 (dd, 2H, J=6.8, 6.8 Hz), 12.6 (s, 1H).

Compound IIIb-12

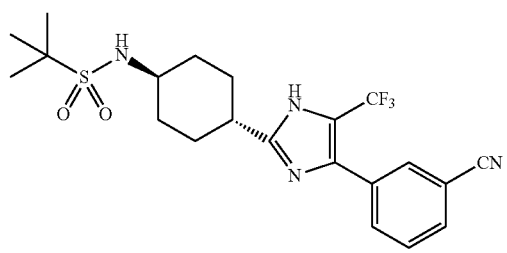

¹H-NMR (DMSO-d₆) δ: 1.29 (s, 9H), 1.32-1.68 (m, 4H), 1.96-2.08 (m, 4H), 2.65 (t, 1H, J=11.4 Hz), 3.05-3.20 (m, 1H), 6.83 (d, 1H, J=6.0 Hz), 7.71 (t, 1H, J=6.0 Hz), 7.79 (d, 1H, J=6.0 Hz), 7.88-7.95 (m, 2H), 12.70 (s, 1H).

Compound IIIb-13

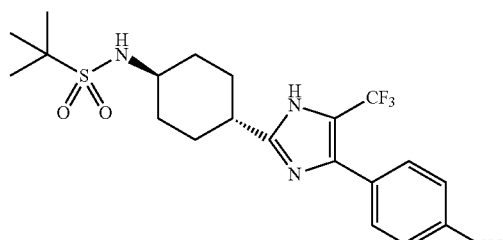

¹H-NMR (CDCl3) δ: 1.30-1.50 (m, 2H), 1.39 (s, 9H), 1.62-1.82 (m, 2H), 2.18-2.38 (m, 4H), 2.79 (t, 1H, J=12.3 Hz), 3.28-3.44 (m, 1H), 3.65-3.76 (m, 1H), 7.57 (d, 2H, J=8.4 Hz), 7.73 (d, 2H, J=8.4 Hz), 9.48 (brs, 1H).

Compound IIIb-14

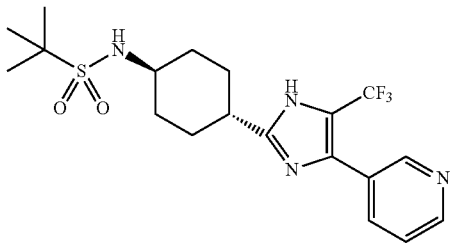

¹H-NMR (DMSO-d₆) δ: 1.28 (s, 9H), 1.34-1.48 (m, 2H), 1.52-1.66 (m, 2H), 1.97-2.08 (m, 4H), 2.65 (m, 1H), 3.13 (m, 1H), 6.83 (d, 1H, J=8.8 Hz), 7.53 (m, 1H), 7.87 (d, 1H, J=7.2 Hz), 8.63 (d, 1H, J=4.4 Hz), 8.67 (s, 1H), 12.8 (s, 1H).

Compound IVa-1

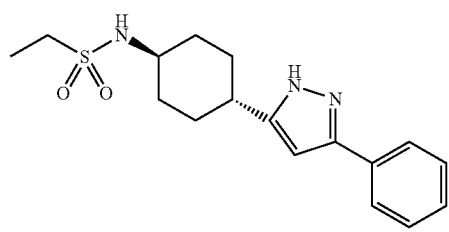

¹H-NMR (DMSO-d₆) δ: 1.23 (t, 3H, J=6.0 Hz), 1.34-1.57 (m, 4H), 1.99-2.01 (m, 4H), 2.56-2.65 (m, 1H), 3.03 (q, 2H, J=6.0 Hz), 3.08-3.18 (m, 1H), 6.47 (s, 1H), 7.10 (d, 1H, J=9.0 Hz), 7.28-7.40 (m, 3H), 7.77-7.79 (m, 2H), 12.58 (s, 1H×4/5), 12.88 (s, 1H×1/5).

Compound IVa-2

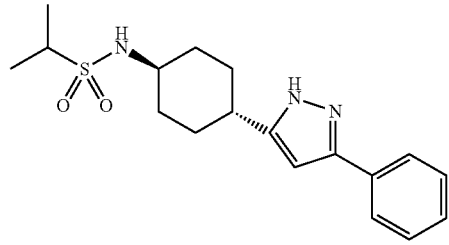

¹H-NMR (DMSO-d₆) δ: 1.23 (d, 6H, J=6.6 Hz), 1.30-1.58 (m, 4H), 1.90-2.10 (m, 4H), 2.48-2.60 (m, 1H), 3.03-3.20 (m, 2H), 6.45 (s, 1H), 7.04 (d, 1H, J=7.8 Hz), 7.26 (t, 1H, J=7.2 Hz), 7.33-7.42 (m, 2H), 7.73 (d, 2H, J=7.5 Hz), 12.61 (brs, 1H).

Compound IVa-3

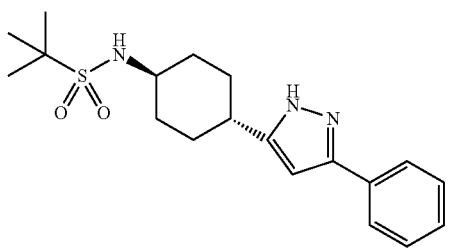

¹H-NMR (DMSO-d₆) δ: 1.28 (s, 9H), 1.32-1.56 (m, 4H), 1.93-2.03 (m, 4H), 2.48-2.64 (m, 1H), 3.04-3.20 (m, 1H), 6.44 (s, 1H), 6.84 (d, 1H, J=8.4 Hz), 7.20-7.45 (m, 3H), 7.65-7.78 (m, 2H), 12.54 (s, 1H×3/4), 12.85 (brs, 1H×1/4).

Compound IVa-6

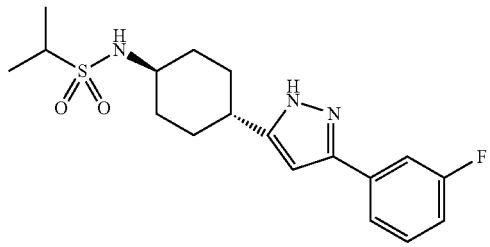

¹H-NMR (DMSO-d₆) δ: 1.23 (d, 6H, J=6.9 Hz), 1.32-1.58 (m, 4H), 1.92-2.04 (m, 4H), 2.48-2.64 (m, 1H), 3.02-3.20 (m, 2H), 6.53 (s, 1H), 7.02-7.14 (m, 2H), 7.36-7.48 (1H, m), 7.50-7.64 (m, 2H), 12.67 (brs, 1H).

Compound IVa-4

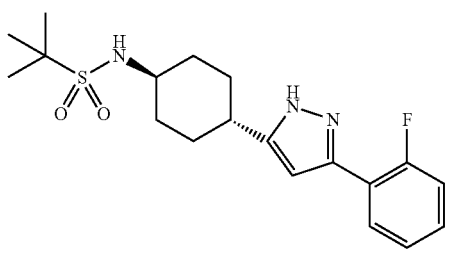

¹H-NMR (DMSO-d₆) δ: 1.30 (s, 9H), 1.34-1.64 (m, 4H), 1.99-2.02 (m, 4H), 2.57-2.68 (m, 1H), 3.08-3.22 (m, 1H), 6.42 (s, 1H), 6.87 (d, 1H, J=9.0 Hz), 7.27-7.33 (m, 3H), 7.95-7.98 (m, 1H), 12.79 (s, 1H).

Compound IVa-7

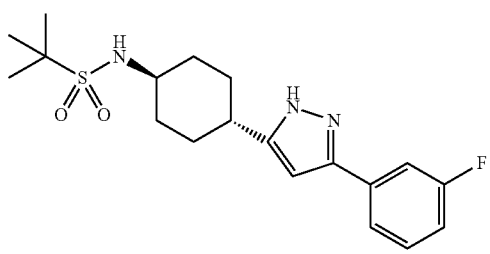

¹H-NMR (DMSO-d₆) δ: 1.30 (s, 9H), 1.37-1.52 (m, 4H), 1.99-2.03 (m, 4H), 2.52-2.60 (m, 1H), 3.07-3.19 (m, 1H), 6.55 (s, 1H), 6.88 (d, 1H, J=9.0 Hz), 7.08-7.13 (m, 1H), 7.40-7.64 (m, 3H), 12.69 (s, 1H).

Compound IVa-5

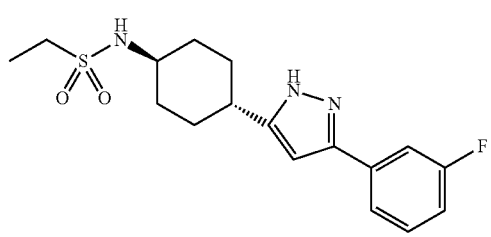

¹H-NMR (DMSO-d₆) δ: 1.23 (t, 3H, J=6.0 Hz), 1.34-1.57 (m, 4H), 1.99-2.01 (m, 4H), 2.56-2.64 (m, 1H), 3.03 (q, 2H, J=6.0 Hz), 3.10-3.16 (m, 1H), 6.54 (s, 1H), 7.09-7.12 (m, 2H), 7.40-7.64 (m, 3H), 12.70 (s, 1H).

Compound IVa-8

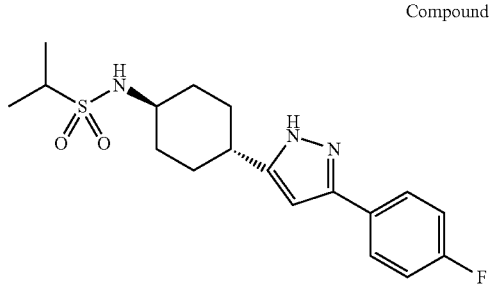

¹H-NMR (DMSO-d₆) δ: 1.26 (d, 6H, J=6.0 Hz), 1.35-1.56 (m, 4H), 1.99-2.01 (m, 4H), 2.54-2.65 (m, 1H), 3.12-3.21 (m, 2H), 6.46 (s, 1H), 7.06 (d, 1H, J=9.0 Hz), 7.19-7.26 (m, 2H), 7.79-7.80 (m, 2H), 12.60 (s, 1H).

Compound IVa-9

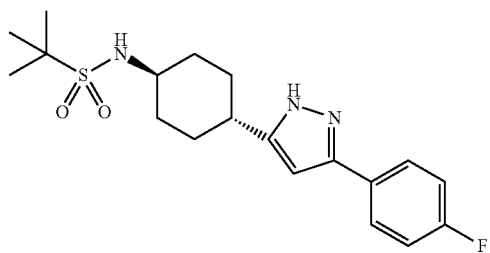

¹H-NMR (DMSO-d$_6$) δ: 1.27 (s, 9H), 1.32-1.56 (m, 4H), 1.93-2.03 (m, 4H), 2.48-2.60 (m, 1H), 3.04-3.20 (m, 1H), 6.44 (s, 1H), 6.84 (d, 1H, J=8.4 Hz), 7.15-7.25 (m, 2H), 7.72-7.80 (m, 2H), 12.58 (brs, 1H).

Compound IVa-12

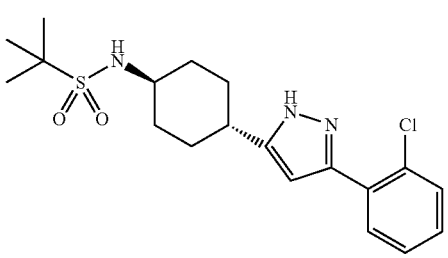

¹H-NMR (DMSO-d$_6$) δ: 1.30 (s, 9H), 1.37-1.58 (m, 4H), 2.00-2.03 (m, 4H), 2.56-2.66 (m, 1H), 3.08-3.21 (m, 1H), 6.52 (s, 1H), 6.87 (d, 1H, J=9.0 Hz), 7.34-7.81 (m, 4H), 12.78 (s, 1H).

Compound IVa-10

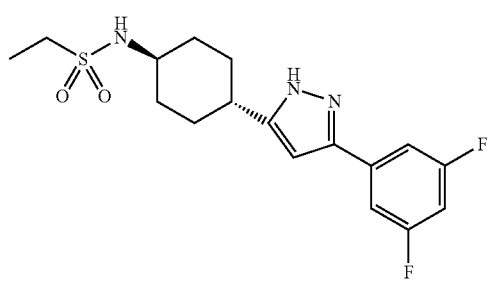

¹H-NMR (DMSO-d$_6$) δ: 1.23 (t, 3H, J=6.0 Hz), 1.34-1.56 (m, 4H), 1.99-2.02 (m, 4H), 2.56-2.64 (m, 1H), 3.03 (q, 2H, J=6.0 Hz), 3.07-3.16 (m, 1H), 6.63 (s, 1H), 7.09-7.17 (m, 2H), 7.45-7.49 (m, 2H), 12.81 (s, 1H).

Compound IVa-13

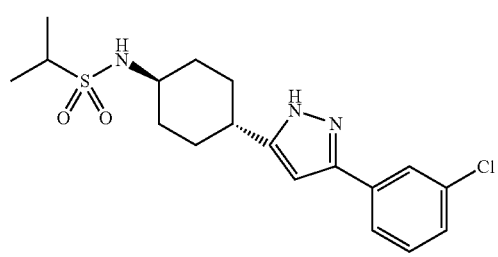

¹H-NMR (CDCl$_3$) δ: 1.39 (s, 3H), 1.41 (s, 3H), 1.51-1.64 (m, 4H), 2.11-2.30 (m, 4H), 2.55-2.61 (m, 1H), 3.14-3.18 (m, 1H), 3.32-3.36 (m, 1H), 4.32-4.47 (m, 1H), 6.33 (s, 1H), 7.29-7.35 (m, 2H), 7.58 (d, 1H, J=8.0 Hz), 7.72 (s, 1H), 10.47 (brs, 1H).

Compound IVa-11

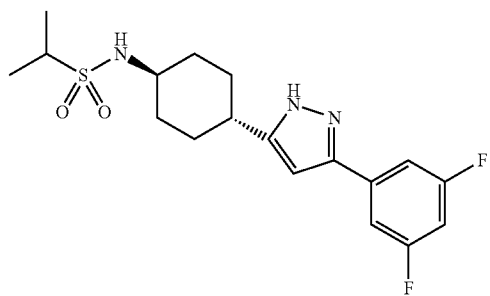

¹H-NMR (DMSO-d$_6$) δ: 1.26 (d, 6H, J=6.0 Hz), 1.35-1.56 (m, 4H), 2.00-2.01 (m, 4H), 2.54-2.64 (m, 1H), 3.12-3.21 (m, 2H), 6.63 (s, 1H), 7.06 (d, 1H, J=9.0 Hz), 7.10-7.17 (m, 1H), 7.46-7.48 (m, 2H), 12.81 (s, 1H).

Compound IVa-14

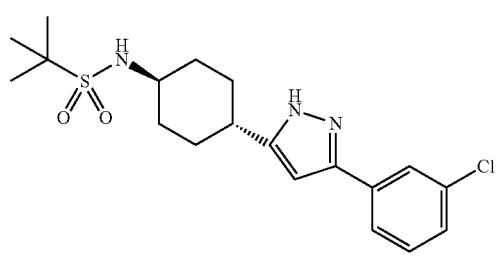

¹H-NMR (DMSO-d$_6$) δ: 1.30 (s, 9H), 1.42-1.52 (m, 4H), 2.00-2.03 (m, 4H), 2.57-2.63 (m, 1H), 3.13-3.17 (m, 1H), 6.57 (s, 1H), 6.88 (d, 1H, J=9.0 Hz), 7.32-7.81 (m, 4H), 12.71 (s, 1H).

Compound IVa-15

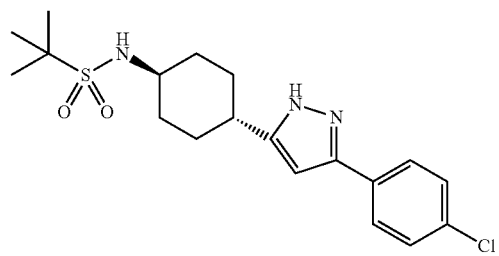

¹H-NMR (DMSO-d₆) δ: 1.30 (s, 9H), 1.37-1.52 (m, 4H), 1.99-2.02 (m, 4H), 2.53-2.65 (m, 1H), 3.09-3.20 (m, 1H), 6.51 (s, 1H), 6.87 (d, 1H, J=9.0 Hz), 7.44-7.81 (m, 4H), 12.66 (s, 1H).

Compound IVa-18

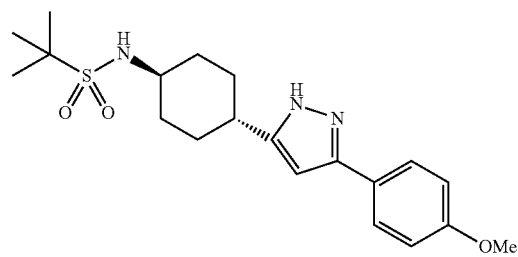

¹H-NMR (DMSO-d₆) δ: 1.30 (s, 9H), 1.42-1.51 (m, 4H), 1.98-2.02 (m, 4H), 2.52-2.61 (m, 1H), 3.06-3.19 (m, 1H), 3.79 (s, 3H), 6.38 (s, 1H), 6.86 (d, 1H, J=9.0 Hz), 6.96-6.98 (m, 2H), 7.67-7.69 (m, 2H), 12.44 (s, 1H).

Compound IVa-16

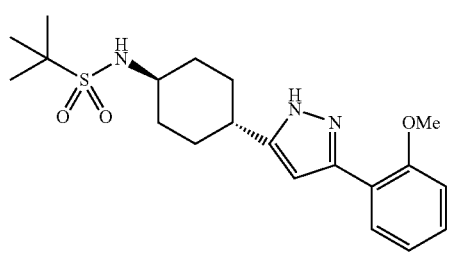

¹H-NMR (DMSO-d₆) δ: 1.28 (s, 9H), 1.32-1.58 (m, 4H), 1.93-2.04 (m, 4H), 2.48-2.60 (m, 1H), 3.04-3.20 (m, 1H), 3.85 (s, 3H), 6.48 (s, 1H), 6.83 (d, 1H, J=8.4 Hz), 6.90-7.14 (m, 2H), 7.20-7.34 (m, 1H), 7.60-7.90 (m, 1H), 12.49 (s, 1H).

Compound IVa-19

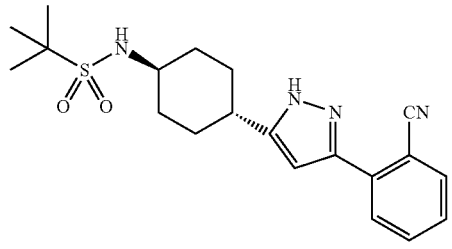

¹H-NMR (DMSO-d₆) δ: 1.28 (s, 9H), 1.34-1.60 (m, 4H), 1.90-2.06 (m, 4H), 2.55-2.68 (m, 1H), 3.04-3.20 (m, 1H), 6.62 (s, 1H), 6.86 (d, 1H, J=9.0 Hz), 7.48 (t, 1H, J=7.8 Hz), 7.72 (t, 1H, J=7.8 Hz), 7.83-7.93 (m, 2H), 12.99 (s, 1H).

Compound IVa-17

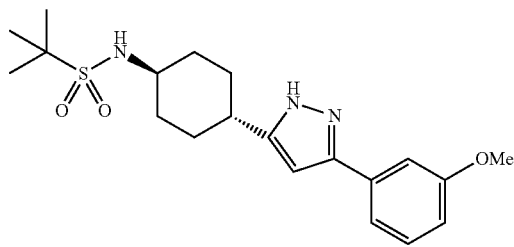

¹H-NMR (DMSO-d₆) δ: 1.28 (s, 9H), 1.32-1.55 (m, 4H), 1.93-2.02 (m, 4H), 2.48-2.62 (m, 1H), 3.04-3.20 (m, 1H), 3.78 (s, 3H), 6.47 (s, 1H), 6.80-6.88 (m, 2H), 7.24-7.34 (m, 3H), 12.53 (s, 1H×3/4), 12.83 (brs, 1H×1/4).

Compound IVa-20

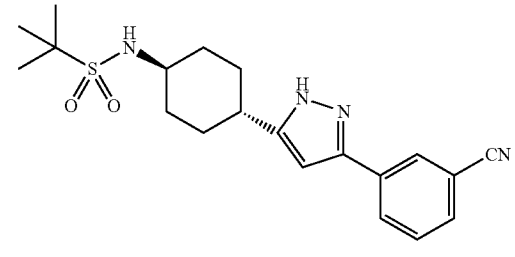

¹H-NMR (DMSO-d₆) δ: 1.28 (s, 9H), 1.34-1.58 (m, 4H), 1.90-2.06 (m, 4H), 2.50-2.64 (m, 1H), 3.06-3.20 (m, 1H), 6.62 (s, 1H), 6.86 (d, 1H, J=9.0 Hz), 7.59 (t, 1H, J=7.8 Hz), 7.72 (d, 1H, J=7.8 Hz), 8.10 (d, 1H, J=7.8 Hz), 8.16 (s, 1H), 12.77 (s, 1H).

Compound IVa-21

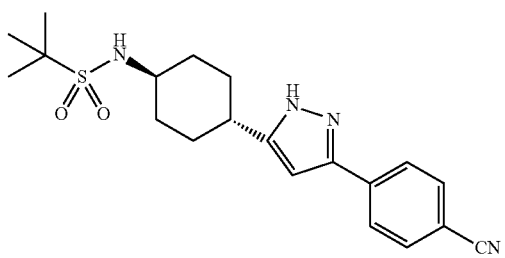

¹H-NMR (DMSO-d₆) δ: 1.28 (s, 9H), 1.34-1.58 (m, 4H), 1.90-2.06 (m, 4H), 2.53-2.66 (m, 1H), 3.06-3.20 (m, 1H), 6.63 (s, 1H), 6.86 (d, 1H, J=8.4 Hz), 7.83 (d, 2H, J=8.4 Hz), 7.95 (d, 2H, J=8.4 Hz), 12.85 (s, 1H).

Compound IVa-22

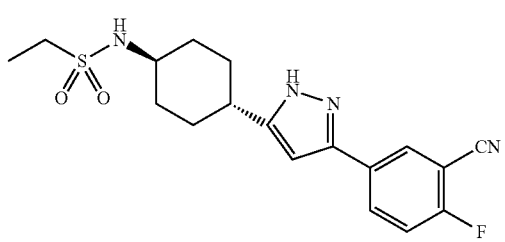

¹H-NMR (DMSO-d₆) δ: 1.21 (t, 3H, J=6.0 Hz), 1.33-1.52 (m, 4H), 1.92-2.01 (m, 4H), 2.55-2.61 (m, 1H), 3.01 (q, 2H, J=6.0 Hz), 3.07-3.15 (m, 1H), 6.60 (s, 1H), 7.07 (d, 1H, J=9.0 Hz), 7.52-7.56 (m, 1H), 8.14-8.24 (m, 2H), 12.77 (s, 1H).

Compound IVa-23

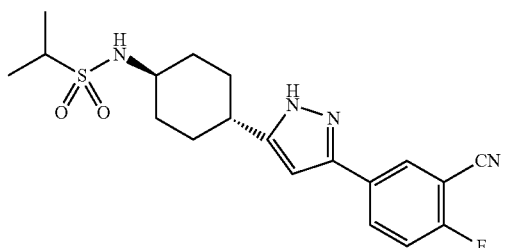

¹H-NMR (DMSO-d₆) δ: 1.24 (d, 6H, J=6.0 Hz), 1.35-1.52 (m, 4H), 1.96-2.01 (m, 4H), 2.55-2.61 (m, 1H), 3.08-3.17 (m, 2H), 6.59 (s, 1H), 7.02 (d, 1H, J=9.0 Hz), 7.51-7.56 (m, 1H), 8.14-8.23 (m, 2H), 12.76 (s, 1H).

Compound IVa-24

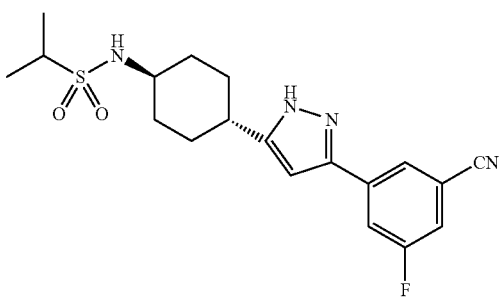

¹H-NMR (DMSO-d₆) δ: 1.28 (s, 9H), 1.33-1.55 (m, 4H), 1.96-2.04 (m, 4H), 2.52-2.63 (m, 1H), 3.04-3.18 (m, 1H), 6.59 (d, 1H, J=1.5 Hz), 6.86 (d, 1H, J=8.7 Hz), 7.53 (t, 1H, J=9.0 Hz), 8.10-8.18 (m, 1H), 8.21 (dd, 1H, J=6.3, 0.9 Hz), 12.75 (s, 1H).

Compound IVa-25

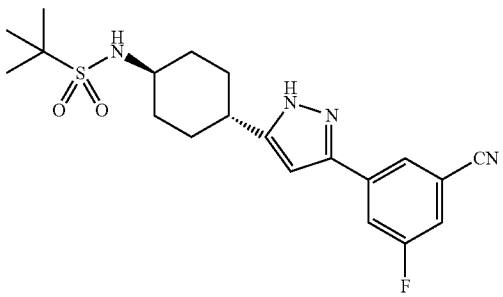

¹H-NMR (DMSO-d₆) δ: 1.26 (d, 6H, J=6.0 Hz), 1.35-1.56 (m, 4H), 1.96-2.04 (m, 4H), 2.53-2.65 (m, 1H), 3.12-3.21 (m, 2H), 6.72 (s, 1H), 7.06 (d, 1H, J=9.0 Hz), 7.74-7.76 (m, 1H), 7.93-7.96 (m, 1H), 8.08 (s, 1H), 12.90 (s, 1H).

Compound IVa-26

¹H-NMR (DMSO-d₆) δ: 1.28 (s, 9H), 1.36-1.54 (m, 4H), 1.95-2.03 (m, 4H), 2.52-2.63 (m, 1H), 3.06-3.18 (m, 1H), 6.69 (s, 1H), 6.82 (d, 1H, J=6.6 Hz), 7.71 (d, 1H, J=5.7 Hz), 7.91 (d, 1H, J=7.5 Hz), 8.05 (s, 1H), 12.86 (s, 1H).

Compound IVa-27

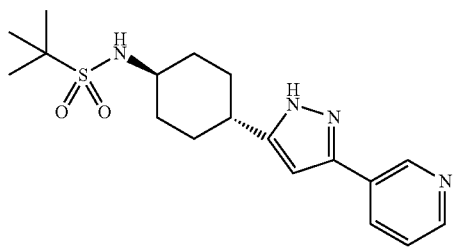

¹H-NMR (DMSO-d₆) δ: 1.30 (s, 9H), 1.38-1.57 (m, 4H), 2.00-2.03 (m, 4H), 2.56-2.65 (m, 1H), 3.09-3.19 (m, 1H), 6.60 (s, 1H), 6.87 (d, 1H, J=9.0 Hz), 7.44 (br, 1H), 8.13 (br, 1H), 8.52 (br, 1H), 9.00 (br, 1H), 12.76 (s, 1H).

Compound IVb-1

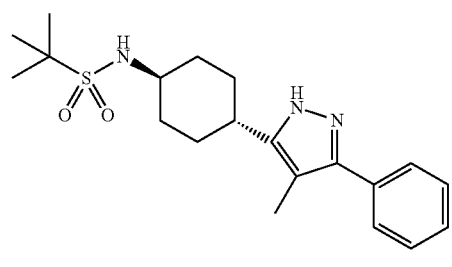

¹H-NMR (DMSO-d₆) δ: 1.29 (s, 9H), 1.38-1.50 (m, 2H), 1.52-1.67 (m, 2H), 1.89-1.97 (m, 2H), 1.95-2.03 (m, 2H), 2.09 (s, 3H), 2.58 (m, 1H), 3.12 (m, 1H), 6.86 (d, 1H, J=8.4 Hz), 7.31 (t, 1H, J=6.8 Hz), 7.42 (dd, 2H, J=7.2, 7.2 Hz), 7.57 (d, 2H, J=7.2 Hz), 12.4 (s, 1H).

Compound IVb-2

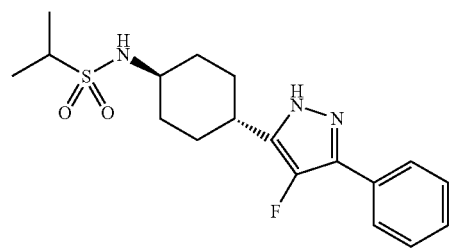

¹H-NMR (DMSO-d₆) δ: 1.23 (d, 6H, J=6.9 Hz), 1.32-1.47 (m, 2H), 1.50-1.68 (m, 2H), 1.90-2.05 (m, 4H), 2.52-2.73 (m, 1H), 3.04-3.22 (m, 2H), 7.05 (t, 1H, J=7.5 Hz), 7.28-7.53 (m, 3H), 7.65 (d, 1H, J=7.5 Hz), 7.73 (d, 1H, J=7.5 Hz), 12.66 (s, 1H×2/3), 12.93 (s, 1H×1/3).

Compound IVb-3

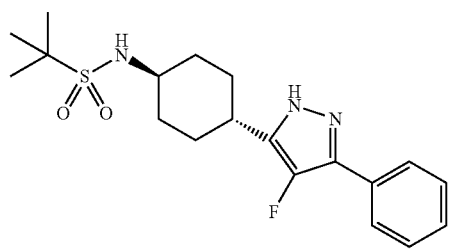

¹H-NMR (DMSO-d₆) δ: 1.28 (s, 9H), 1.32-1.68 (m, 4H), 1.90-2.05 (m, 4H), 2.55-2.75 (m, 1H), 3.04-3.20 (m, 1H), 6.87 (t, 1H, J=8.1 Hz), 7.28-7.53 (m, 3H), 7.66 (d, 1H, J=7.2 Hz), 7.74 (d, 1H, J=7.2 Hz), 12.65 (s, 1H×2/3), 12.94 (s, 1H×1/3).

Compound IVb-4

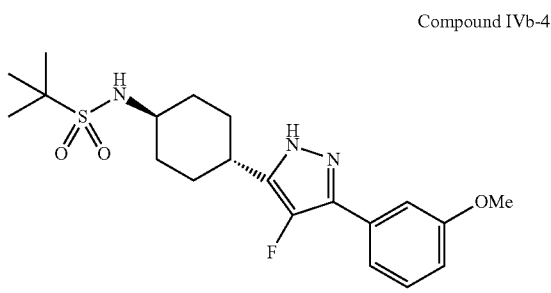

¹H-NMR (DMSO-d₆) δ: 1.31 (s, 9H), 1.39-1.68 (m, 4H), 1.96-2.04 (m, 4H), 2.60-2.72 (m, 1H), 3.08-3.20 (m, 1H), 3.82 (s, 3H), 6.88-6.91 (m, 2H), 7.28-7.40 (m, 3H), 12.67 (s, 1H×2/3), 12.96 (s, 1H×1/3).

Compound IVb-5

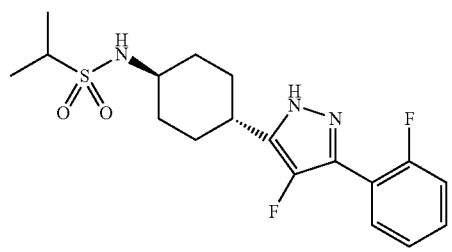

¹H-NMR (DMSO-d₆) δ: 1.23 (d, 6H, J=6.9 Hz), 1.32-1.47 (m, 2H), 1.50-1.68 (m, 2H), 1.90-2.02 (m, 4H), 2.54-2.74 (m, 1H), 3.04-3.22 (m, 2H), 7.02-7.10 (m, 1H), 7.23-7.52 (m, 3H), 7.54-7.63 (m, 1H), 12.83 (s, 1H).

Compound IVb-6

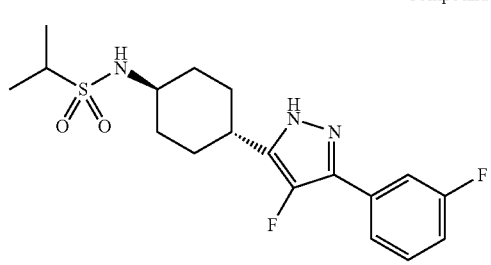

¹H-NMR (DMSO-d₆) δ: 1.23 (d, 6H, J=6.9 Hz), 1.32-1.47 (m, 2H), 1.50-1.68 (m, 2H), 1.90-2.02 (m, 4H), 2.56-2.74 (m, 1H), 3.04-3.22 (m, 2H), 7.06 (d, 1H, J=7.8 Hz), 7.10-7.24 (m, 1H), 7.43-7.61 (m, 3H), 12.80 (s, 1H×3/4), 13.03 (s, 1H×1/4).

Compound IVb-7

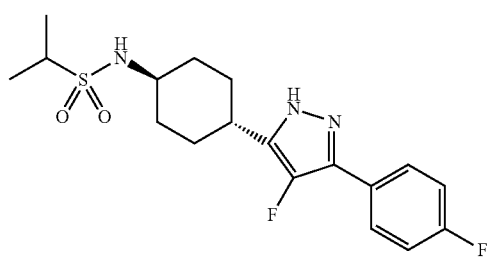

¹H-NMR (DMSO-d₆) δ: 1.23 (d, 6H, J=6.9 Hz), 1.32-1.46 (m, 2H), 1.48-1.68 (m, 2H), 1.90-2.02 (m, 4H), 2.56-2.74 (m, 1H), 3.04-3.22 (m, 2H), 7.02-7.08 (m, 1H), 7.22-7.38 (m, 2H), 7.65-7.80 (m, 2H), 12.68 (s, 1H×3/4), 12.93 (s, 1H×1/4).

Compound IVb-8

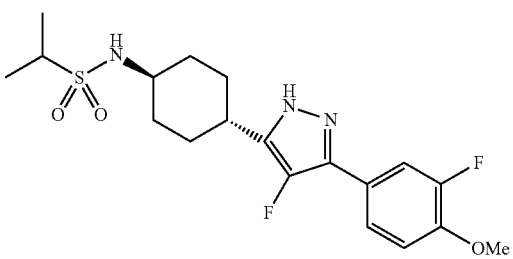

¹H-NMR (DMSO-d₆) δ: 1.23 (d, 6H, J=6.6 Hz), 1.32-1.47 (m, 2H), 1.48-1.68 (m, 2H), 1.90-2.02 (m, 4H), 2.56-2.74 (m, 1H), 3.04-3.22 (m, 2H), 3.87 (s, 3H×3/4), 3.88 (s, 3H×1/4), 7.02-7.08 (m, 1H), 7.20-7.34 (m, 1H), 7.42-7.53 (m, 2H), 12.65 (s, 1H×3/4), 12.86 (s, 1H×1/4).

Compound IVb-9

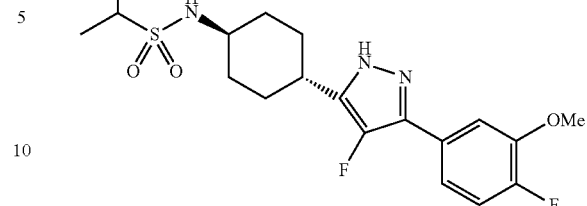

¹H-NMR (DMSO-d₆) δ: 1.23 (d, 6H, J=6.9 Hz), 1.32-1.47 (m, 2H), 1.48-1.68 (m, 2H), 1.90-2.02 (m, 4H), 2.54-2.72 (m, 1H), 3.04-3.22 (m, 2H), 3.87 (s, 3H×2/3), 3.88 (s, 3H×1/3), 7.02-7.08 (m, 1H), 7.16-7.46 (m, 3H), 12.67 (s, 1H×2/3), 12.93 (s, 1H×1/3).

Compound IVb-10

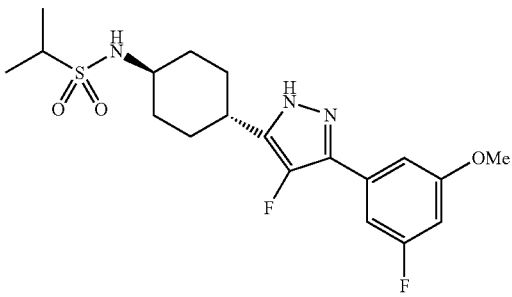

¹H-NMR (DMSO-d₆) δ: 1.23 (d, 6H, J=6.9 Hz), 1.30-1.47 (m, 2H), 1.48-1.68 (m, 2H), 1.90-2.02 (m, 4H), 2.54-2.72 (m, 1H), 3.04-3.22 (m, 2H), 3.80 (s, 3H×2/3), 3.81 (s, 3H×1/3), 6.77-6.89 (m, 1H), 7.02-7.12 (m, 3H), 12.79 (s, 1H×2/3), 13.02 (s, 1H×1/3).

Compound IVb-11

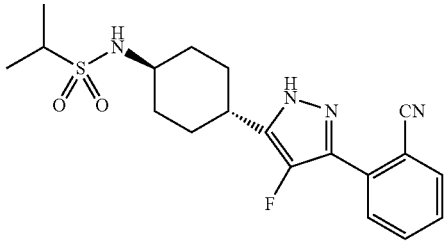

¹H-NMR (DMSO-d₆) δ: 1.23 (d, 6H, J=6.9 Hz), 1.34-1.47 (m, 2H), 1.53-1.68 (m, 2H), 1.94-2.03 (m, 4H), 2.65-2.75 (m, 1H), 3.06-3.20 (m, 2H), 7.05 (d, 1H, J=6.0 Hz), 7.57 (t, 1H, J=5.7 Hz), 7.72 (d, 1H, J=5.4 Hz), 7.78 (t, 1H, J=4.8 Hz), 7.92 (d, 1H, J=5.4 Hz), 13.07 (s, 1H).

Compound IVb-12

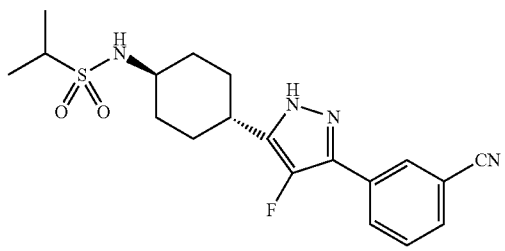

¹H-NMR (DMSO-d₆) δ: 1.23 (d, 6H, J=6.6 Hz), 1.32-1.48 (m, 2H), 1.50-1.68 (m, 2H), 1.90-2.03 (m, 4H), 2.60-2.75 (m, 1H), 3.04-3.22 (m, 2H), 7.06 (d, 1H, J=7.8 Hz), 7.62-7.75 (m, 1H), 7.76-7.86 (m, 1H), 7.93-8.07 (m, 2H), 12.91 (s, 1H×3/4), 13.10 (s, 1H×1/4).

Compound IVb-15

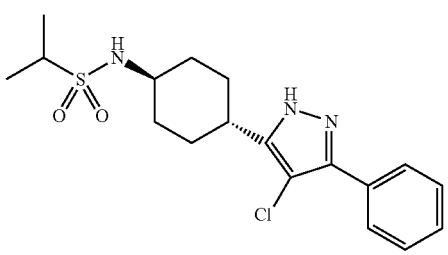

¹H-NMR (DMSO-d₆) δ: 1.23 (d, 6H, J=6.9 Hz), 1.32-1.50 (m, 2H), 1.54-1.74 (m, 2H), 1.84-2.04 (m, 4H), 2.52-2.76 (m, 1H), 3.04-3.22 (m, 2H), 7.02-7.12 (m, 1H), 7.32-7.56 (m, 3H), 7.66-7.84 (m, 2H), 13.05 (s, 1H×1/2), 13.18 (s, 1H×1/2).

Compound IVb-13

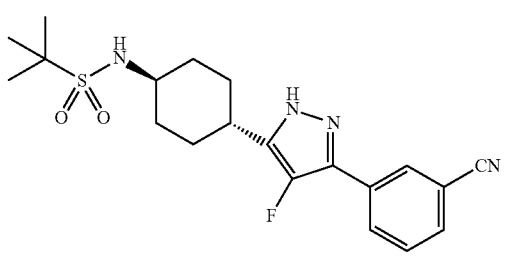

¹H-NMR (DMSO-d₆) δ: 1.31 (s, 9H), 1.37-1.67 (m, 4H), 1.96-2.04 (m, 4H), 2.65-2.73 (m, 1H), 3.13-3.16 (m, 1H), 6.91 (d, 1H, J=9.0 Hz), 7.67-7.73 (m, 1H), 7.82-7.85 (m, 1H), 8.05-8.08 (m, 2H), 12.97 (s, 1H).

Compound IVb-16

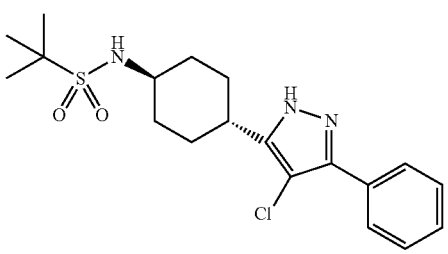

¹H-NMR (DMSO-d₆) δ: 1.29 (s, 9H), 1.35-1.54 (m, 2H), 1.56-1.74 (m, 2H), 1.84-2.06 (m, 4H), 2.56-2.76 (m, 1H), 3.04-3.20 (m, 1H), 6.83-6.92 (m, 1H), 7.32-7.56 (m, 3H), 7.68-7.84 (m, 2H), 13.02 (s, 1H×1/2), 13.18 (s, 1H×1/2).

Compound IVb-14

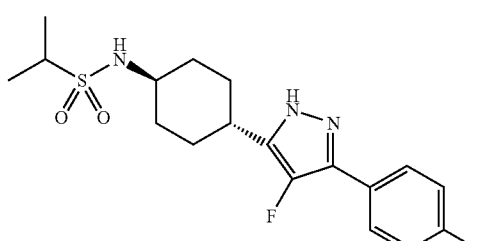

¹H-NMR (DMSO-d₆) δ: 1.23 (d, 6H, J=6.6 Hz), 1.32-1.48 (m, 2H), 1.50-1.68 (m, 2H), 1.90-2.03 (m, 4H), 2.60-2.75 (m, 1H), 3.04-3.22 (m, 2H), 7.07 (d, 1H, J=8.1 Hz), 7.78-8.00 (m, 4H), 12.98 (s, 1H×4/5), 13.23 (s, 1H×1/5).

Compound IVb-17

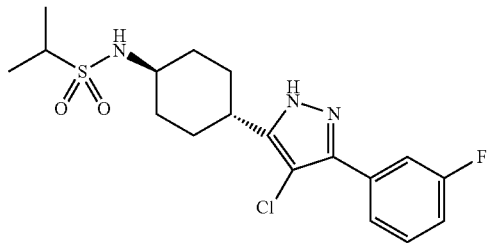

¹H-NMR (DMSO-d₆) δ: 1.24 (d, 6H, J=6.9 Hz), 1.32-1.50 (m, 2H), 1.54-1.74 (m, 2H), 1.84-2.04 (m, 4H), 2.54-2.76 (m, 1H), 3.06-3.22 (m, 2H), 7.02-7.10 (m, 1H), 7.15-7.32 (m, 1H), 7.46-7.74 (m, 3H), 13.18 (s, 1H×3/4), 13.30 (s, 1H×1/4).

Compound IVb-18

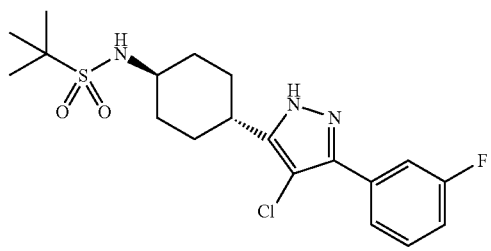

¹H-NMR (DMSO-d₆) δ: 1.29 (s, 9H), 1.32-1.52 (m, 2H), 1.54-1.74 (m, 2H), 1.84-2.06 (m, 4H), 2.54-2.76 (m, 1H), 3.06-3.22 (m, 1H), 6.85-6.92 (m, 1H), 7.18-7.30 (m, 1H), 7.46-7.74 (m, 3H), 13.15 (s, 1H×2/3), 13.31 (brs, 1H×1/3).

Compound IVb-19

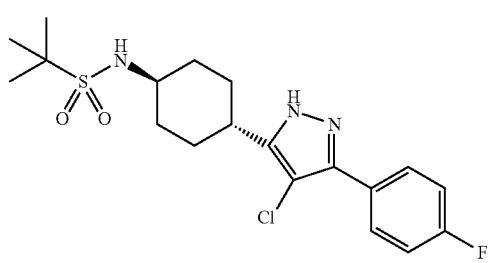

¹H-NMR (DMSO-d₆) δ: 1.27 (s, 9H), 1.32-1.50 (m, 2H), 1.52-1.70 (m, 2H), 1.82-2.04 (m, 4H), 2.54-2.76 (m, 1H), 3.06-3.22 (m, 1H), 6.85 (d, 6H, J=8.4 Hz), 7.25-7.35 (m, 2H), 7.76-7.84 (m, 2H), 13.06 (brs, 1H).

Compound IVb-20

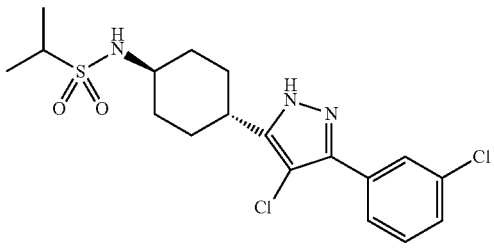

¹H-NMR (DMSO-d₆) δ: 1.24 (d, 6H, J=6.6 Hz), 1.32-1.50 (m, 2H), 1.55-1.72 (m, 2H), 1.82-2.04 (m, 4H), 2.54-2.76 (m, 1H), 3.06-3.22 (m, 2H), 7.00-7.10 (m, 1H), 7.40-7.60 (m, 2H), 7.66-7.86 (m, 2H), 13.20 (s, 1H×2/3), 13.39 (s, 1H×1/3).

Compound IVb-21

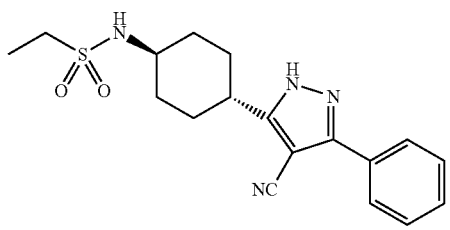

¹H-NMR (DMSO-d₆) δ: 1.12-1.24 (m, 3H), 1.32-1.48 (m, 2H), 1.58-1.76 (m, 2H), 1.86-2.05 (m, 4H), 2.65-2.88 (m, 1H), 2.97-3.07 (m, 2H), 3.08-3.20 (m, 1H), 7.07-7.15 (m, 1H), 7.35-7.60 (m, 3H), 7.68-7.90 (m, 2H), 13.59 (brs, 1H×2/3), 13.78 (s, 1H×1/3).

Compound IVb-22

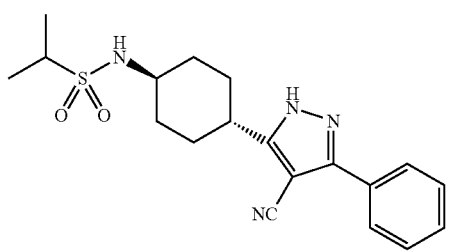

¹H-NMR (DMSO-d₆) δ: 1.24 (d, 6H, J=6.8 Hz), 1.41-1.47 (m, 2H), 1.63-1.69 (m, 2H), 1.81-1.96 (m, 4H), 2.77-2.86 (m, 1H), 3.13-3.20 (m, 2H), 7.06-7.08 (m, 2H), 7.38-7.53 (m, 2H), 7.73 (brs, 1H), 7.84 (bs, 1H), 13.14 (brs, 1H×1/3), 13.69 (brs, 1H×2/3).

Compound IVb-23

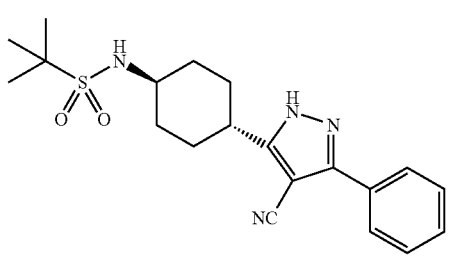

¹H-NMR (DMSO-d₆) δ: 1.29 (s, 9H), 1.41-1.49 (m, 2H), 1.65-1.68 (m, 2H), 1.98-2.04 (m, 4H), 2.78 (bs, 1H), 3.13 (bs, 1H), 6.89 (d, 1H, J=8.4 Hz), 7.52 (bs, 3H), 7.83 (brs, 2H), 13.65 (s, 1H×2/3), 13.77 (brs, 1H×1/3).

Compound IVb-24

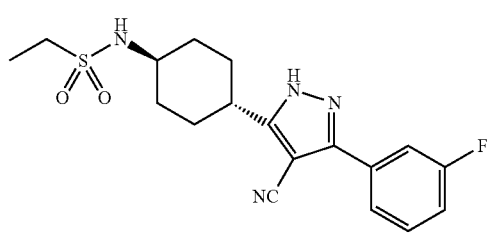

¹H-NMR (DMSO-d₆) δ: 1.14-1.26 (m, 3H), 1.35-1.48 (m, 2H), 1.60-1.77 (m, 2H), 1.95-2.06 (m, 4H), 2.65-2.90 (m, 1H), 2.98-3.08 (m, 2H), 3.08-3.20 (m, 1H), 7.04-7.16 (m, 1H), 7.16-7.75 (m, 4H), 13.72 (s, 1H×3/4), 13.89 (s, 1H×1/4).

Compound IVb-25

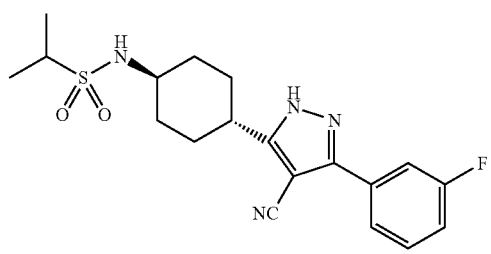

¹H-NMR (DMSO-d₆) δ: 1.23 (d, 6H, J=6.9 Hz), 1.32-1.52 (m, 2H), 1.58-1.78 (m, 2H), 1.94-2.08 (m, 4H), 2.72-2.90 (m, 1H), 3.06-3.24 (m, 2H), 7.07 (d, 1H, J=7.8 Hz), 7.26-7.38 (m, 1H), 7.46-7.74 (m, 3H), 13.72 (s, 1H).

Compound IVb-26

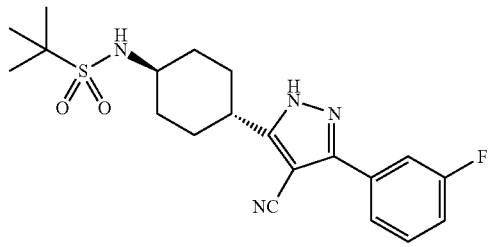

¹H-NMR (DMSO-d₆) δ: 1.28 (s, 9H), 1.36-1.52 (m, 2H), 1.58-1.76 (m, 2H), 1.94-2.08 (m, 4H), 2.72-2.90 (m, 1H), 3.06-3.20 (m, 1H), 6.99 (d, 1H, J=6.0 Hz), 7.24-7.38 (m, 1H), 7.52-7.72 (m, 3H), 13.68 (s, 1H×4/5), 13.88 (s, 1H×1/5).

Compound IVb-27

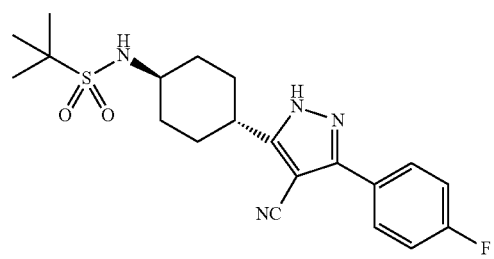

¹H-NMR (DMSO-d₆) δ: 1.28 (s, 9H), 1.35-1.52 (m, 2H), 1.58-1.75 (m, 2H), 1.94-2.08 (m, 4H), 2.72-2.88 (m, 1H), 3.06-3.20 (m, 1H), 6.88 (d, 1H, J=6.0 Hz), 7.16-7.42 (m, 2H), 7.72-7.92 (m, 2H), 13.59 (s, 1H).

Compound IVb-28

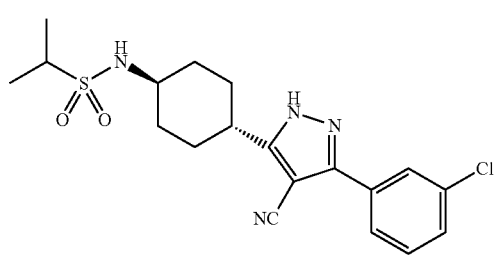

¹H-NMR (DMSO-d₆) δ: 1.24 (d, 6H, J=6.6 Hz), 1.35-1.52 (m, 2H), 1.58-1.76 (m, 2H), 1.94-2.06 (m, 4H), 2.72-2.88 (m, 1H), 3.06-3.22 (m, 2H), 7.08 (d, 1H, J=5.4 Hz), 7.46-7.66 (m, 2H), 7.75-7.87 (m, 2H), 13.73 (s, 1H×4/5), 13.92 (s, 1H×1/5).

Compound Va-1

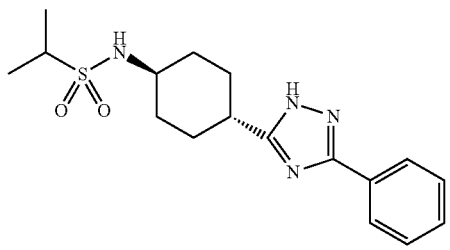

¹H-NMR (DMSO-d₆) δ: 1.23 (d, 6H, J=6.9 Hz), 1.32-1.48 (m, 2H), 1.50-1.66 (m, 2H), 1.94-2.10 (m, 4H), 2.64-2.76 (m, 1H), 3.06-3.22 (m, 2H), 7.05 (d, 1H, J=8.1 Hz), 7.36-7.50 (m, 3H), 7.96 (d, 2H, J=6.9 Hz), 13.69 (brs, 1H).

Compound Va-2

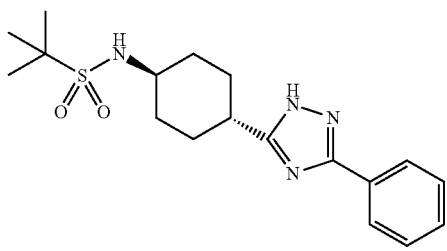

¹H-NMR (DMSO-d$_6$) δ: 1.28 (s, 9H), 1.36-1.45 (m, 2H), 1.46-1.64 (m, 2H), 1.94-2.12 (m, 4H), 2.64-2.76 (m, 1H), 3.06-3.20 (m, 1H), 6.86 (d, 1H, J=8.0 Hz), 7.35-7.50 (m, 3H), 7.96 (d, 2H, J=8.0 Hz), 13.72 (brs, 1H).

Compound Va-3

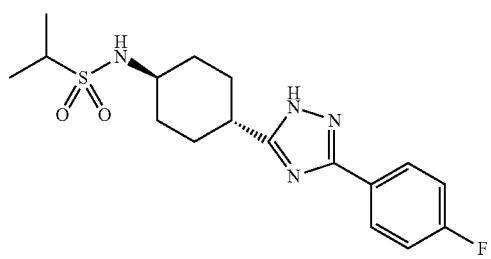

¹H-NMR (DMSO-d$_6$) δ: 1.24 (d, 6H, J=6.9 Hz), 1.32-1.49 (m, 2H), 1.50-1.66 (m, 2H), 1.94-2.10 (m, 4H), 2.70 (t, 1H, J=11.4 Hz), 3.06-3.22 (m, 2H), 7.06 (d, 1H, J=8.1 Hz), 7.24-7.34 (m, 2H), 8.00 (dd, 2H, J=9.0, 5.7 Hz), 13.71 (brs, 1H).

Compound Va-4

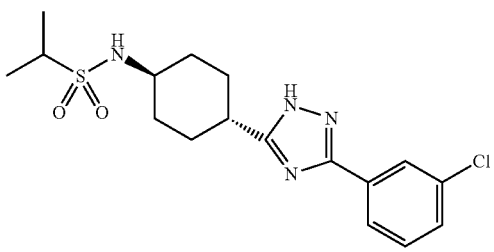

¹H-NMR (DMSO-d$_6$) δ: 1.23 (d, 6H, J=6.6 Hz), 1.32-1.49 (m, 2H), 1.51-1.66 (m, 2H), 1.94-2.10 (m, 4H), 2.72 (t, 1H, J=11.4 Hz), 3.06-3.22 (m, 2H), 7.06 (d, 1H, J=8.1 Hz), 7.44-7.53 (m, 2H), 7.90-7.96 (m, 2H), 13.83 (brs, 1H).

Compound Va-5

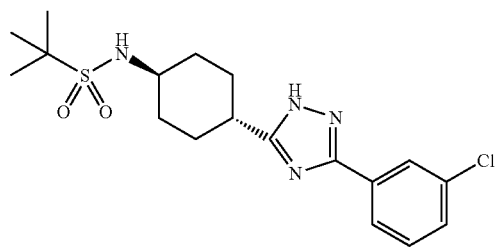

¹H-NMR (DMSO-d$_6$) δ: 1.28 (s, 9H), 1.36-1.45 (m, 2H), 1.46-1.64 (m, 2H), 1.94-2.12 (m, 4H), 2.64-2.76 (m, 1H), 3.06-3.20 (m, 1H), 6.85 (d, 1H, J=8.0 Hz), 7.34-7.53 (m, 2H), 13.83 (brs, 1H).

Compound Va-6

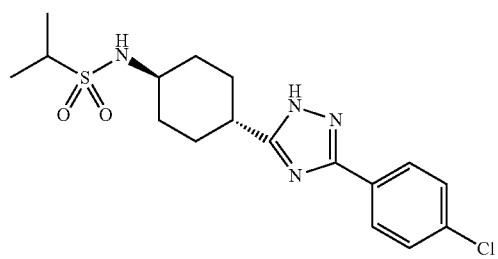

¹H-NMR (DMSO-d$_6$) δ: 1.23 (d, 6H, J=6.6 Hz), 1.32-1.49 (m, 2H), 1.50-1.66 (m, 2H), 1.94-2.10 (m, 4H), 2.70 (t, 1H, J=11.4 Hz), 3.06-3.22 (m, 2H), 7.06 (d, 1H, J=8.1 Hz), 7.52 (d, 1H, J=8.4 Hz), 7.97 (d, 1H, J=8.4 Hz), 13.78 (brs, 1H).

Compound Va-7

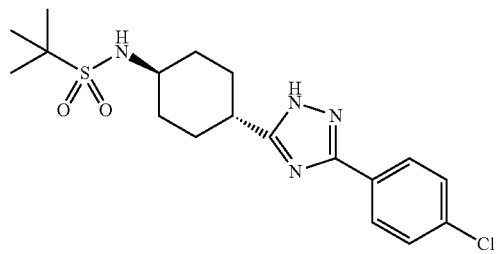

¹H-NMR (DMSO-d$_6$) δ: 1.28 (s, 9H), 1.36-1.45 (m, 2H), 1.46-1.64 (m, 2H), 1.94-2.12 (m, 4H), 2.64-2.76 (m, 1H), 3.06-3.20 (m, 1H), 6.85 (d, 1H, J=8.0 Hz), 7.51 (d, 2H, J=8.0 Hz), 7.99 (d, 2H, J=8.0 Hz), 13.75 (brs, 1H).

Compound Va-8

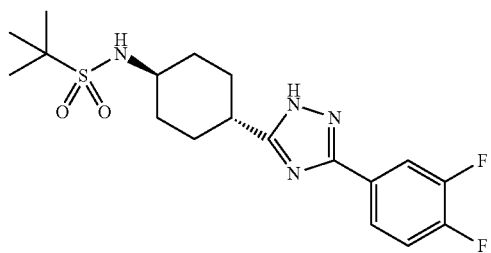

¹H-NMR (DMSO-d₆) δ: 1.28 (s, 9H), 1.36-1.45 (m, 2H), 1.46-1.64 (m, 2H), 1.94-2.12 (m, 4H), 2.64-2.76 (m, 1H), 3.06-3.20 (m, 1H), 6.85 (d, 1H, J=8.0 Hz), 7.46-7.56 (m, 1H), 7.76-7.93 (m, 2H), 13.82 (brs, 1H).

Compound Va-9

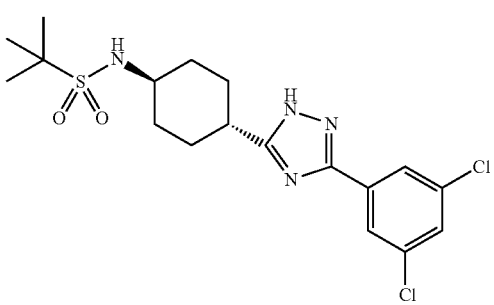

¹H-NMR (DMSO-d₆) δ: 1.28 (s, 9H), 1.34-1.66 (m, 4H), 1.96-2.12 (m, 4H), 2.72 (t, 1H, J=11.4 Hz), 3.06-3.20 (m, 1H), 6.87 (d, 1H, J=8.7 Hz), 7.66 (s, 1H), 7.91 (d, 2H, J=1.8 Hz), 13.96 (brs, 1H).

Compound VI-1

¹H-NMR (DMSO-d₆) δ: 1.28 (s, 9H), 1.31-1.45 (m, 2H), 1.56-1.70 (m, 2H), 1.82-1.91 (m, 2H), 1.94-2.02 (m, 2H), 2.42 (m, 1H), 3.14 (m, 1H), 6.35 (s, 1H), 6.40 (s, 1H), 6.83 (d, 1H, J=8.4 Hz), 7.40-7.50 (m, 3H), 7.64-7.71 (m, 2H), 11.5 (br.s, 1H).

Compound VI-2

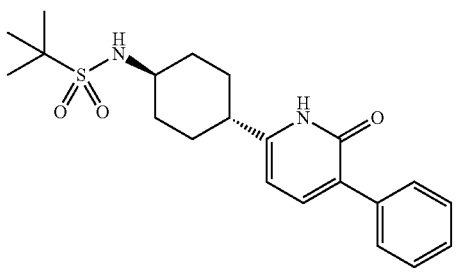

Experiment 1-1

Affinity for Mouse NPY Y5 Receptor cDNA sequence encoding a mouse NPY Y5 receptor (Biochim. Biophys. Acta 1328:83-89, 1997) was cloned in a vector (pME18S, Takebe et al. Mol. Cell. Biol. 8, 8957). The obtained expression vector was transfected into CHO cells as a host by using Lipofect AMINE Reagent (Trademark, Gico BRL Co., Ltd.) according to the instruction manual. The cells that stably express NPY Y5 receptor were obtained.

The membranes prepared from the CHO cells expressing NPY Y5 receptor, the compound of this invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was filtered from the mixture through a glass filter (GF/C) presoaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test compound against the specific peptide YY binding (IC$_{50}$ value) was calculated (Inui, A. et al. Endocrinology 131, 2090-2096 (1992)). The results are shown in Table 1.

The compounds of this invention inhibited the binding of peptide YY (NPY homologue) to NPY Y5 receptor, indicating that the compounds of this invention have an affinity for the NPY Y5 receptor.

TABLE 1

| Compound | binding affinity, IC$_{50}$(nM) |
|---|---|
| Ia-2 | 1.1 |
| Ia-7 | 0.28 |
| Ia-18 | 5.5 |
| Ib-14 | 0.29 |
| Ib-28 | 1.3 |
| Ib-32 | 0.75 |
| IIa-3 | 0.22 |
| IIIa-1 | 0.85 |
| IIIb-7 | 0.70 |
| IVa-3 | 1.4 |
| IVb-23 | 0.37 |
| Va-2 | 2.2 |

Experiment 1-2

Affinity for Human NPY Y5 Receptor cDNA sequence encoding a human NPY Y5 receptor (WO96/16542) was cloned in a vector (pME18S, Takebe et al. Mol. Cell. Biol. 8, 466-472). The obtained expression vector was transfected into CHO cells as a host by using Lipofect AMINE Reagent (Trademark, Gico BRL Co., Ltd.) according to the instruction manual. The cells that stably express human NPY Y5 receptor were obtained.

The membranes prepared from the CHO cells expressing human NPY Y5 receptor, the compound of this invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was filtered from the mixture through a glassfilter (GF/C) pre-soaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test compound against the specific peptide YY binding ($IC_{50}$ value) was calculated (Inui, A. et al. Endocrinology 131, 2090-2096 (1992)).

The compounds of this invention inhibited the binding of peptide YY (NPY homologue) to human NPY Y5 receptor, indicating that the compounds of this invention have an affinity for the human NPY Y5 receptor.

Experiment 2

Evaluation for Brain Penetration in Rats and Mice

By using the cassette dosing method (Drug. Metab. Dispos. (2001); 29, 957-966), brain penetration rate of the compounds (brain/plasma partition coefficients; Kp) were evaluated from plasma and brain concentrations at 30 minutes after intravenous administration (0.5 mg/mL/kg) in rats (Crl; CD (SD), ♂, 8 weeks) or at 3 or 5 hours after oral administration (2 mg/10 mL/kg) in mice (Jcl; C57BL/6J, ♂, 8 weeks).

As a result, pyrazole derivatives of this invention showed high brain penetration rates. For example, Kp, brain of Compound IVa-3 showed 3.69 in rats and 1.78 in mice. The other compounds of this invention also showed high brain penetration rates. Table 2 shows the Kp, brain of each compound.

TABLE 2

| Compound | Rat Kp, brain | Mouse Kp, brain |
| --- | --- | --- |
| Ia-8 | 3.55 | 2.11 |
| Ib-13 | 2.30 | 1.33 |
| Ib-35 | 1.91 | 0.89 |
| IIIa-4 | 1.37 | 0.45 |
| IVa-3 | 3.69 | 1.78 |
| IVa-9 | 2.28 | 2.41 |
| IVb-1 | 1.88 | 1.44 |
| IVb-3 | 5.84 | 3.14 |

Experiment 3

Pharmacokinetic Analysis in Rats

By using the cassette dosing method, half-life (t1/2) and total clearance (CLtot) of the compounds of this invention were estimated from change in plasma concentration of each compound in rats (Crl; CD (SD), ♂, 8 weeks) after intravenous administration (0.5 mg/mL/kg). The results are shown in Table 3.

TABLE 3

| Compound | Rat t½ (hr) | Rat CLtot (mL/min/kg) |
| --- | --- | --- |
| Ia-8 | 1.57 | 17.8 |
| IIIa-4 | 2.96 | 14.8 |
| IIIa-13 | 1.17 | 14.5 |
| IIIb-1 | 4.04 | 3.46 |
| IIIb-5 | 7.67 | 3.84 |
| IVa-3 | 3.82 | 7.43 |
| IVa-9 | 13.6 | 2.67 |
| IVb-3 | 8.14 | 4.04 |
| Va-2 | 6.4 | 2.60 |
| Va-5 | 9.1 | 3.82 |

Experiment 4

Inhibitory Effect on cAMP Production in CHO Cells

CHO cells expressing human NPY Y5 receptor were incubated in the presence of 2.5 mM isobutylmethylxanthine (SIGMA) at 37° C. for 20 min. After the incubation the compound of this invention was added, and then the mixture was incubated for 5 min. Next, 50 nM NPY and 10 μM forskolin (SIGMA) were added, and the mixture was incubated for 30 min. After termination of the reaction by adding 1N HCl, the amount of cAMP in the supernatant was determined with an EIA kit (Amersham LIFE SCIENCE). The inhibitory activity of NPY against forskolin stimulated cAMP production was expressed as 100% and the 50% inhibitory concentration ($IC_{50}$ value) of the compound of this invention against the NPY activity was calculated.

Experiment 5

Using the membranes prepared from Y1-expression cells (human neuroblastoma, SK-N-MC) and the membranes prepared from Y2-expression cells (human neuroblastoma, SMS-KAN), the experiment was carried out in a similar way as Experiment 1-2 to determine the affinity of the compounds for NPY Y1 and NPY Y2 receptor. The results showed that the compounds of this invention had no significant affinity for their receptors, indicating high selectivity for NPY Y5 receptor.

Experiment 6

Under diethylether anesthesia the skull of male C57BL/6J mice (12-14 week old, 25-30 g) was exposed by making an incision about 1-cm long from external occipital crest to nasal dorsum, and drilled in the 1-mm lateral position to the left following 1-mm posterior from bregma. After recovery from anesthesia mice were dosed with either 0.5% hydroxypropylmethyl cellulose solution (Shin-Etsu Chemical Co., Ltd) or the compounds of this invention suspended in the 0.5% hydroxypropylmethyl cellulose solution. At one hour after the treatment, each animal received a NPY Y5 receptor specific agonist, [cPP$^{1-7}$, NPY$^{19-23}$, Ala$^{31}$, Aib$^{32}$, Gln$^{34}$]-hPancreatic Polypeptide (0.1 nmol/1.5 μL/mouse) through the skull opening using a canula. Residual food was measured at 2 and 4 hours after the treatment, and the difference in food intake between the compounds-treated mice and 0.5% hydroxypropylmethyl cellulose solution-treated mice was calculated. The compound at 6 mg/kg caused a significant reduction in food intake of mice compared to the treatment with 0.5% hydroxypropylmethyl cellulose solution.

For example, mean food intakes at 2 and 4 hours after oral administration of Compound IVa-9 at 6 mg/kg in mice (Group A) were 0.24±0.05 g and 0.51±0.06 g, respectively. On the other hand, mean food intakes at 2 and 4 hours after oral administration of 0.5% hydroxypropylmethyl cellulose solution in mice (Group B) were 0.58±0.07 g and 1.26±0.10 g, respectively. Also, mean food intakes at 2 and 4 hours after oral administration of 0.5% hydroxypropylmethyl cellulose solution without ICV injection of NPY Y5 receptor specific agonist in mice (Group C) were 0.06±0.04 g and 0.14±0.05 g, respectively. After subtracting the mean value of Group C from that of Group A or B, the inhibition rates of the compound on food intake at 2 and 4 hours after administration in Group A against Group B were estimated. The rates of the compound were 65.4% and 67.0%, respectively.

Experiment 7

Test for Inhibition of CYP2C9 Enzyme

The test for inhibition of CYP2C9 enzyme was carried out with human liver microsomes and hydration activity of 4-position of tolbutamide that is a typical reaction of CYP2C9 as a parameter.

The reaction condition was as below: A substrate, 5 μM Tolbutamide ($^{14}C$ labeled compound); the reaction time, 30 minutes; the reaction temperature, 37° C.; the protein concentration, 0.25 mg/ml (human liver microsomes, 15 pol, Lot. 210296, XenoTech).

To the HEPES Buffer (pH 7.4), was added the protein (human liver microsomes), a drug solution and a substrate with the composition as the above. NADPH, which is a coenzyme of the reaction, was added thereto to start the reaction. After reacting for the fixed hours, 2N hydrochloric acid solution was added thereto and the reaction was stopped by removing protein. The remaining substrate drug and the generating metabolite were extracted with chloroform. The solvent was removed and the residue was redissolved in methanol. This solution was spotted on TLC, developed with chloroform:methanol:acetic acid=90:10:1, contacted on the imaging plate for about 14-20 hours and analyzed by BAS2000. As to the generation activity of the metabolite, Tolbutamide 4-potition hydration body, the activity in case that the solvent dissolving a drug was added to the reaction assay was used as a control (100%). The residual activity (%) in case that the test drug solution was added to the reaction was calculated to confirm the compounds of this invention had little effect on inhibition of CYP2C9 enzyme.

Experiment 8

Test for Metabolic Stability

Test for Metabolic Stability in Hepatic Microsomes: To trishydrochloric acid buffer (pH 7.4), were added NADPH (the final concentration was 1 mM in case of oxidative metabolism), Hepatic Microsomes (the final concentration was 0.5 mg protein/ml) and each compound (the final concentration was 2 μM). The mixture was reacted at 37° C. for 0 and 30 minutes. In case of conjugated glucuronic acid, UDPGA (the final concentration is 5 mM) was added instead of NADPH. The reaction was stopped by adding acetonitrile/methanol=1/1 (v/v) which is 2 parts by volume based on 1 part by volume of the reaction solution and then compounds in the centrifugal supernatant were measured by HPLC. By comparing the values between 0 and 30 minutes the disappearance volume of the compounds by the metabolic reaction was calculated to confirm metabolic stability of the compounds of this invention.

Experiment 9

Test for Solubility

The compounds of this invention and test solvents (JP-2 solution, and JP-2 solution containing 20 mM sodium taurocholate) were stirred at 37° C. for 3 hours. The mixture was filtrated with a 0.45 μm filter and the concentration of the filtrate was measured with HPLC method to confirm solubility of compounds of this invention.

FORMULATION EXAMPLE

The following Formulation Examples are only exemplified and not intended to limit the scope of this invention.

Formulation Example 1

Tablets

| | |
|---|---|
| Compound (I) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture is crushed, granulated and dried to obtain a suitable size of granules. Next, calcium stearate is added to the granules. Finally, tableting is performed under a compression force.

Formulation Example 2

Capsules

| | |
|---|---|
| Compound (I) | 10 mg |
| Magnesium stearate | 10 mg |
| Lactose | 80 mg |

The above ingredients are mixed uniformly to obtain powders or fine granules, and then the obtained mixture is filled into capsules.

Formulation Example 3

Granules

| | |
|---|---|
| Compound (I) | 30 g |
| Lactose | 265 g |
| Magnesium stearate | 5 g |

After the above ingredients are mixed uniformly, the mixture is compressed, crushed, granulated and sieved to obtain a suitable size of granules.

Industrial Applicability

As shown in the above Experiments, the compounds of this invention have NPY Y5 receptor antagonistic activity. Therefore, the compounds of this invention are very useful as a medicine for preventing or treating feeding disorder, obesity, hyperorexia, sexual disorder, impaired fertility, depression, epileptic seizure, hypertension, cerebral hemorrhage, congestive heart failure, sleep disorders or the like.

The invention claimed is:

1. A compound of formula (I):

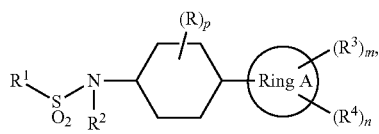

or a pharmaceutically acceptable salt thereof,
wherein:
$R^1$ is substituted or unsubstituted alkyl, substituted or unsubstituted alkenyl, or substituted or unsubstituted alkynyl;
$R^2$ is hydrogen or, substituted or unsubstituted alkyl;
Ring A is pyrrolopyridine;
$R^3$ is substituted or unsubstituted aryl, substituted or unsubstituted heteroaryl, or substituted or unsubstituted heterocyclyl;
$R^4$ is halogen, cyano, nitro, nitroso, azide, oxo, substituted or unsubstituted alkyl, substituted or unsubstituted alkenyl, substituted or unsubstituted alkynyl, substituted or unsubstituted cycloalkyl, substituted or unsubstituted cycloalkenyl, hydroxy, substituted or unsubstituted alkoxy, substituted or unsubstituted alkenyloxy, substituted or unsubstituted cycloalkyloxy, substituted or unsubstituted cycloalkenyloxy, substituted or unsubstituted aryloxy, substituted or unsubstituted heteroaryloxy, substituted or unsubstituted heterocyclyloxy, mercapto, substituted or unsubstituted alkylthio, substituted or unsubstituted alkenylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclylthio, carboxy, substituted or unsubstituted alkoxycarbonyl, substituted or unsubstituted alkenyloxycarbonyl, substituted or unsubstituted cycloalkyloxycarbonyl, substituted or unsubstituted cycloalkenyloxycarbonyl, substituted or unsubstituted aryloxycarbonyl, substituted or unsubstituted heteroaryloxycarbonyl, substituted or unsubstituted heterocyclyloxycarbonyl, substituted or unsubstituted carbamoyl, formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl, substituted or unsubstituted heterocyclylcarbonyl, sulfino, sulfo, substituted or unsubstituted alkylsulfonyl, substituted or unsubstituted alkenylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclylsulfonyl, substituted or unsubstituted sulfamoyl, or substituted or unsubstituted amino;
m is an integer between 0 and 2;
n is an integer between 0 and 3;
R is halogen, oxo, cyano, nitro, substituted or unsubstituted alkyl, substituted or unsubstituted alkenyl, or substituted or unsubstituted alkynyl; and
p is an integer between 0 and 2.

2. The compound of claim 1, wherein m is 1,
or a pharmaceutically acceptable salt thereof.

3. The compound of claim 1, wherein $R^1$ is alkyl,
or a pharmaceutically acceptable salt thereof.

4. The compound of claim 1, wherein $R^3$ is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted morpholinyl, substituted or unsubstituted morpholino, substituted or unsubstituted pyrrolidinyl, substituted or unsubstituted piperidyl, substituted or unsubstituted piperidino, substituted or unsubstituted benzodioxolyl, substituted or unsubstituted dihydrobenzoxazinyl, or substituted or unsubstituted indazolyl,
or a pharmaceutically acceptable salt thereof.

5. The compound of claim 1, wherein $R^4$ is halogen, cyano, oxo, substituted or unsubstituted alkyl, substituted or unsubstituted cycloalkyl, substituted or unsubstituted alkoxy, or substituted or unsubstituted aryloxy,
or a pharmaceutically acceptable salt thereof.

6. The compound of claim 1, wherein n is 1,
or a pharmaceutically acceptable salt thereof.

7. The compound of claim 1, wherein
$R^1$ is substituted or unsubstituted alkyl,
$R^2$ is hydrogen,
Ring A is pyrrolopyridine,
$R^3$ is substituted or unsubstituted phenyl, substituted or unsubstituted pyridyl, substituted or unsubstituted pyrimidinyl, substituted or unsubstituted pyrazinyl, substituted or unsubstituted thiazolyl, substituted or unsubstituted oxazolyl, substituted or unsubstituted morpholinyl, substituted or unsubstituted pyrrolidinyl, or substituted or unsubstituted piperidyl, and
$R^4$ is halogen, cyano, substituted or unsubstituted alkyl, substituted or unsubstituted alkoxy or, substituted or unsubstituted aryloxy,
or a pharmaceutically acceptable salt thereof.

* * * * *